US012692466B2

(12) United States Patent
Golan

(10) Patent No.: US 12,692,466 B2
(45) Date of Patent: Jul. 28, 2026

(54) CLOSED PHOTOBIOREACTORS FOR MICROORGANISM CULTIVATION

(71) Applicant: BREVEL LTD., Rehovot (IL)

(72) Inventor: Ido Golan, Rehovot (IL)

(73) Assignee: BREVEL LTD., Rehovot (IL)

( * ) Notice: Subject to any disclaimer, the term of this patent is extended or adjusted under 35 U.S.C. 154(b) by 1021 days.

(21) Appl. No.: 17/792,138

(22) PCT Filed: Jan. 19, 2021

(86) PCT No.: PCT/IL2021/050055
§ 371 (c)(1),
(2) Date: Jul. 11, 2022

(87) PCT Pub. No.: WO2021/149045
PCT Pub. Date: Jul. 29, 2021

(65) Prior Publication Data
US 2023/0051997 A1     Feb. 16, 2023

(30) Foreign Application Priority Data

Jan. 20, 2020    (IL) ......................................... 272146

(51) Int. Cl.
*C12M 1/00*        (2006.01)
*C12M 1/34*        (2006.01)
*C12N 1/12*        (2026.01)
(52) U.S. Cl.
CPC ............ *C12M 21/02* (2013.01); *C12M 23/38* (2013.01); *C12M 29/16* (2013.01); *C12M 31/10* (2013.01); *C12M 41/12* (2013.01); *C12N 1/12* (2013.01)

(58) Field of Classification Search
None
See application file for complete search history.

(56) References Cited

U.S. PATENT DOCUMENTS

| | | | |
|---|---|---|---|
| 3,986,297 | A | 10/1976 | Ichimura et al. |
| 4,676,956 | A | 6/1987 | Mori |
| 5,104,803 | A | 4/1992 | Delente |
| 5,162,051 | A | 11/1992 | Hoeksema |
| 9,506,100 | B2 | 11/2016 | Romari et al. |
| 9,605,238 | B2 | 3/2017 | Johnson et al. |
| 9,688,951 | B2 | 6/2017 | Krenbrink et al. |
| 10,287,538 | B2 | 5/2019 | Barbarin |
| 2005/0135104 | A1 | 6/2005 | Crabb et al. |

(Continued)

FOREIGN PATENT DOCUMENTS

| | | | |
|---|---|---|---|
| AU | 2010277555 | B2 | 1/2016 |
| CN | 102203233 | A | 9/2011 |

(Continued)

OTHER PUBLICATIONS

Document titled JP2002000256A Culture Apparatus for Algae, machine translation of JP2002000256A provided by Espacenet (Year: 2002).*

(Continued)

*Primary Examiner* — Holly Kipouros
(74) *Attorney, Agent, or Firm* — The Roy Gross Law Firm, LLC; Roy D. Gross

(57)     ABSTRACT
The disclosed technology, in some embodiments, relates to the field of photobioreactors and more particularly, to photobioreactors having improved internal illumination capabilities.

18 Claims, 11 Drawing Sheets

(56) References Cited

U.S. PATENT DOCUMENTS

| | | | |
|---|---|---|---|
| 2009/0047722 A1 | 2/2009 | Wilkerson et al. | |
| 2009/0148931 A1 | 6/2009 | Wilkerson et al. | |
| 2010/0028977 A1 | 2/2010 | Ng et al. | |
| 2010/0267125 A1* | 10/2010 | Erb | C12M 27/20 |
| | | | 435/292.1 |
| 2011/0097789 A1 | 4/2011 | Goodwin et al. | |
| 2011/0107664 A1 | 5/2011 | Rancis et al. | |
| 2012/0171733 A1 | 7/2012 | Im et al. | |
| 2012/0288921 A1 | 11/2012 | Yuan et al. | |
| 2013/0102076 A1 | 4/2013 | Licamele et al. | |
| 2015/0210970 A1* | 7/2015 | Hellingwerf | C12M 41/06 |
| | | | 435/257.1 |
| 2016/0113224 A1 | 4/2016 | Chiang et al. | |
| 2016/0168522 A1 | 6/2016 | Krenbrink et al. | |
| 2017/0145378 A1 | 5/2017 | Ganuza et al. | |

FOREIGN PATENT DOCUMENTS

| | | | | |
|---|---|---|---|---|
| CN | 102382754 | A | 3/2012 | |
| DE | 29819259 | U1 | 11/1999 | |
| DE | 10315750 | A1 | 10/2004 | |
| DE | 202007013406 | U1 | 11/2007 | |
| DE | 202008005412 | U1 | 7/2008 | |
| GB | 2425702 | A | 11/2006 | |
| JP | S5911174 | A | 1/1984 | |
| JP | 2001178443 | A | 7/2001 | |
| JP | 2002000256 | A * | 1/2002 | C12M 23/38 |
| KR | 20120029576 | A | 3/2012 | |
| KR | 101222145 | B1 | 1/2013 | |
| KR | 20130029586 | A | 3/2013 | |
| WO | 7900282 | A1 | 5/1979 | |
| WO | 9015953 | A1 | 12/1990 | |
| WO | 9711154 | A1 | 3/1997 | |
| WO | 9824879 | A1 | 6/1998 | |
| WO | 2005068605 | A1 | 7/2005 | |
| WO | 2010013998 | A1 | 2/2010 | |
| WO | 2010014010 | A2 | 2/2010 | |
| WO | 2010115996 | A1 | 10/2010 | |
| WO | 2010116946 | A1 | 10/2010 | |
| WO | 2011012714 | A2 | 2/2011 | |
| WO | 2012109375 | A2 | 8/2012 | |
| WO | WO-2019034792 | A1 * | 2/2019 | C12M 31/10 |
| WO | 2019064291 | A1 | 4/2019 | |

OTHER PUBLICATIONS

Machine translation of WO 2019034792 A1 provided by Clarivate, original document published Aug. 17, 2018. (Year: 2018).*

Patent Landscape Report: Microalgae-Related Technologies; 2016. Prepared for the World Intellectual Property Organization (WIPO) by Questel Consulting (Chilton V, Mantrand N, Morel B). In cooperation with Moroccan Office of Industrial and Commercial Property (OMPIC) and the Moroccan Foundation for Advanced Science, Innovation and Research (MASCIR). 74 pages.

* cited by examiner

CLOSED PHOTOBIOREACTORS FOR MICROORGANISM CULTIVATION

This application is a National Phase of PCT Patent Application No. PCT/IL2021/050055 having International filing date of Jan. 19, 2021, which claims the benefit of priority of Israeli Patent Application No. 272146, filed Jan. 20, 2020, the contents of which are all incorporated herein by reference in their entirety.

FIELD OF THE INVENTION

The disclosed technology, in some embodiments, relates to the field of photobioreactors and more particularly, to photobioreactors having improved internal illumination capabilities.

BACKGROUND OF THE INVENTION

Artificially cultivating bio-organisms such as bacteria and/or algae can be utilized for various purposes, such as the production of food for mammals, the production of biofuels, the treatment of sewage and waste waters, the production of enzymes having diverse applications, and more. In order to successfully artificially cultivate phototrophic bio-organisms such as phototrophic bacteria and/or algae, the bio-organisms are required to be exposed to a relatively constant and uniform source of light Such cultivation of can be performed utilizing photobioreactors having various illumination systems, such as internal illumination systems. Since these illumination systems can emit considerable amounts of heat which can affect or even harm the heat sensitive bio-organism's cultures, the photobioreactors often include various cooling means for the illumination systems.

Photobioreactors having cooling means for illumination systems have been previously reported. For example, U.S. Pat. No. 5,104,803 discloses a photobioreactor for the cultivation of photosynthetic microorganisms having at least one light bank substantially totally immersible in the liquid microbial culture contained in the photobioreactor so that substantially all of the emitted light is absorbed in the culture.

US Pub. No. 2009/0148931 discloses a bioreactor system for growing photosynthetic organisms, wherein the bioreactor system includes a bioreactor and an illumination system, the illumination system includes one more optical wave guides configured to light at least some of a plurality of photosynthetic organisms retained in the bioreactor.

US Pub. No. 2016/0168522 discloses a bioreactor system for growing a photosynthetic culture, having a vessel containing an aqueous liquid and a lighting system to irradiate the photosynthetic culture.

U.S. Pat. No. 9,605,238 discloses a photo-bioreactor having a reactor vessel arranged to contain a fluid medium within which bio-material is grown, and at least one light-emitting rod extending into the reactor vessel.

There remains an unmet need for large scale, cost-efficient, and effective photobioreactors and systems having improved inner illumination capabilities and efficient cooling means.

SUMMARY OF THE INVENTION

The following aspects and embodiments thereof are described and illustrated in conjunction with systems, devices and methods which are meant to be exemplary and illustrative, not limiting in scope. In various embodiments, one or more of the above-described problems have been reduced or eliminated, while other embodiments are directed to other advantages or improvements.

According to some embodiments, there is provided a closed photobioreactor for growing a microorganism culture in an aqueous medium, the photobioreactor comprising: a vessel comprising a vessel floor, a vessel cover positioned substantially parallel thereto, and at least one vessel wall positioned perpendicular to the vessel floor and vessel cover, defining an internal cavity for containing the microorganism culture in the aqueous medium, wherein the vessel cover comprises a plurality of openings; and a plurality of transparent pipes attached to the vessel cover configured to accommodate a plurality of light sources within lumens thereof, wherein each of the transparent pipes extends through one of the openings, wherein each transparent pipe has a first open end located out of the internal cavity of the vessel, and a second end, wherein a first portion of each transparent pipe is connected to the vessel cover or the vessel floor, and a second portion of each transparent pipe is located within the internal cavity, wherein each of the transparent pipes is substantially sealed to one of the openings, so that the internal cavity is isolated from the surrounding environment of the vessel.

According to some embodiments, the first portion of each transparent pipe is connected to the vessel cover.

Thus, according to some embodiments, the present invention provides a closed photobioreactor for growing a microorganism culture in an aqueous medium, the photobioreactor comprising: a vessel comprising a vessel floor, a vessel cover positioned substantially parallel thereto, and at least one vessel wall positioned perpendicular to the vessel floor and vessel cover, defining an internal cavity for containing the microorganism culture in the aqueous medium, wherein the vessel cover comprises a plurality of openings; and a plurality of transparent pipes attached to the vessel cover configured to accommodate a plurality of light sources within lumens thereof, wherein each of the transparent pipes extends through one of the openings, wherein each transparent pipe has a first open end located out of the internal cavity of the vessel, and a second end, wherein a first portion of each transparent pipe is connected to the vessel cover, and a second portion of each transparent pipe is located within the internal cavity, wherein each of the transparent pipes is substantially sealed to one of the openings, so that the internal cavity is isolated from the surrounding environment of the vessel.

According to some embodiments, each transparent pipe is connected to the vessel cover and to the vessel floor.

According to some embodiments, the vessel cover comprises a plurality of hollow cover extensions, wherein each hollow cover extension extends from one of the openings upward, and has a first open end offset upward from the vessel cover and a second open end at the level of the vessel cover, wherein the first portion of each transparent pipe extends through one of the hollow cover extensions and is retained thereby.

According to some embodiments, the closed photobioreactor further comprises a plurality of retention units, wherein each of the retention units comprises at least one retention member, each retention member is configured to fix one of the transparent pipes to one of the hollow cover extensions, wherein each of the retention units comprises at least one retention member disposed circumferentially between the first portion of one of the transparent pipes and one of the hollow cover extensions, and longitudinally between the second end of one of the hollow cover extensions and the first end of one of the transparent pipes, and configured to limit spontaneous movement of the transparent pipe in the lateral and longitudinal directions.

According to some embodiments, each of the retention units comprises a plurality of lower retention members and a plurality of upper retention members, each of which is disposed circumferentially between one of the transparent pipes and one of the hollow cover extensions, and longitudinally between the second end of one of the hollow cover extensions and the first end of one of the transparent pipes, and configured to limit spontaneous movement of the transparent pipe in the lateral and longitudinal directions.

According to some embodiments, each of the lower retention members comprises a lower squeezable gasket, and each of the upper retention members comprises an upper squeezable gasket.

According to some embodiments, each hollow cover extension comprises an internal recess, located between the first end and the second end thereof, wherein each lower squeezable gasket is housed within one of the internal recesses and pressing the transparent pipe inward, wherein each hollow cover extension comprises a slanted portion at the first end thereof tapering upwards, wherein each upper squeezable gasket is housed within one of the slanted portions and is pressed against the transparent pipe inward.

According to some embodiments, each of the transparent pipes is externally tubular and each of the hollow cover extensions is internally tubular, wherein each of the lower squeezable gaskets comprises a lower rubber O-ring, and each of the upper squeezable gaskets comprises a upper rubber O-ring, wherein each of the lower rubber O-rings and the upper rubber O-rings, when expanded, has an internal diameter larger than the external diameter of the first portion of each corresponding transparent pipe.

According to some embodiments, the closed photobioreactor further comprises a plurality of double-open caps reversibly attachable to the first end of each hollow cover extension, wherein each double-open cap has a plane having a diameter smaller than the external diameter of the upper O-ring, wherein upon capping the double-open cap to the hollow cover extension, the plane presses against the upper O-ring and the slanted portion of the hollow cover extension, to press fit the upper O-ring inward against the transparent pipe, and prevents the transparent pipe from longitudinally moving upwards.

According to some embodiments, each double-open cap comprises an threaded internal tubular portion and each hollow cover extension comprises a threaded external portion, wherein the double-open cap is screwable to the hollow cover extension, wherein upon screwing the cap presses the hollow cover extension inwards, further press fitting the hollow cover extension and upper O-ring inward against the transparent pipe.

According to some embodiments, the lumen of each transparent pipe is in fluid communication with the surrounding environment of the vessel and isolated from the internal cavity of the vessel.

According to some embodiments, each of the vessel cover and hollow cover extensions is made of metal, wherein each of the hollow cover extensions is welded to the vessel cover.

According to some embodiments, the first open end of each transparent pipe is offset upward from the first open end of the hollow extension, which retains it.

According to some embodiments, the at least one vessel wall is a double walled cooling jacket comprising at least one internal wall, at least one external wall and a cooling liquid there between, wherein the internal wall is bounding the internal cavity of the vessel.

According to some embodiments, the closed photobioreactor further comprises an impeller comprising at least one blade and configured to stir the microorganism culture in the aqueous medium when inside the internal cavity of the vessel, wherein the impeller is connected to at least one of the vessel floor and the vessel cover, and positioned perpendicular to the vessel floor and the vessel cover and parallel to each of the transparent pipes.

According to some embodiments, the closed photobioreactor further comprises a closed cap configured to plug the first open end of each of the transparent pipes.

According to some embodiments, the plurality of transparent pipes are accommodating a plurality of light sources within the lumens thereof, wherein upon the accommodation, a positive gap between the internal diameter of the transparent pipe and the external dimensions of the light source exists, wherein each of the light sources is drawable from the transparent pipe, which accommodates it.

According to some embodiments, each transparent pipe is accommodating one or more of the light sources and a cooling liquid, wherein each light source comprises at least one illuminating plane and at least one heat emitting plane, wherein the cooling liquid is in contact with at least the heat emitting plane. According to some embodiments, each of the plurality of light sources is an LED lamp.

According to some embodiments, the closed photobioreactor comprises a plurality of hollow illuminating LED pipes, each hollow illuminating LED pipe comprising: a first open end facing the vessel cover; a second end facing the vessel floor; an internal surface connected to the heat emitting plane of one or more of the LED lamps; an external surface connected to the illuminating plane of one or more of the LED lamps; and a lumen within the internal surface of the hollow illuminating LED pipe, wherein the cooling liquid is in contact with at least the heat emitting plane, enabling heat transfer between the cooling liquid and the heat emitting plane of one or more of the LED lamps.

According to some embodiments, the closed photobioreactor comprises a plurality of hollow illuminating LED pipes, and a plurality of heat pipes wherein each hollow illuminating LED pipe comprising: a plurality of LED lamps, each comprising a heat emitting plane and an illuminating plane; a first open end facing the vessel cover; a second end facing the vessel floor; an internal surface connected to the heat emitting plane of each one of the plurality of LED lamps; an external surface connected to the illuminating plane of each one of the plurality of LED lamps; and a lumen within the internal surface of the hollow illuminating LED pipe; wherein each heat pipe is made from a heat conducting material, and is containing a LED cooling fluid, wherein each heat pipe comprises an internal surface and an external surface, wherein each of the plurality of hollow illuminating LED pipes in accommodated within the lumen of one of the plurality of transparent pipes, wherein each of the heat pipes is accommodated within the lumen of one of the hollow illuminating LED pipes, so that the external surface of the heat pipe is in contact with the internal surface of the hollow illuminating LED pipe, wherein the LED cooling fluid is in contact with the internal surface of the heat pipe, enabling heat transfer between the cooling fluid and the heat emitting plane of the plurality of LED lamps.

According to some embodiments, a positive gap between the external surface of the hollow illuminating LED pipe and the internal diameter of the transparent pipe, which accommodate it, exists, wherein each of the hollow illuminating LED pipes is drawable from said transparent pipe.

According to some embodiments, each heat pipe comprises: a first closed end extending through transparent pipe first open end, which accommodates it; a second closed end facing the vessel floor; and a heat transferring portion between the first end and the second end, wherein the heat transferring portion is in contact with the internal surface of the hollow illuminating LED pipe.

According to some embodiments, each hollow illuminating LED pipe is formed from the plurality of LED lamps and the external surface of the heat pipe, wherein the internal surface hollow illuminating LED pipe is the heat pipe heat transferring portion.

According to some embodiments, each hollow illuminating LED pipe is formed from the plurality of LED strips, each comprising a plurality of LED lamps mounted to a circuit board; wherein the heat pipe heat transferring portion is attached to the circuit board.

According to some embodiments, the closed photobioreactor further comprises at least one cooling unit, wherein each heat pipe is in contact with one of the at least one cooling unit, wherein the at least one cooling unit is configured to reduce the temperature of the LED cooling fluid.

According to some embodiments, the first end of the heat pipe is in contact with one of the at least one cooling unit, thereby enabling condensation of vapors of the LED cooling fluid in the vicinity of said first end.

According to some embodiments, there is provided a process for growing a microorganism culture in an aqueous medium, wherein the process comprises growing at least one cell population in the closed photobioreactor disclosed herein.

According to some embodiments, there is provided process for growing a microorganism culture in an aqueous medium, the process comprising (a) providing the closed photobioreactor disclosed herein, wherein the plurality of transparent pipes are accommodating a plurality of light sources within the lumens thereof; (b) placing an aqueous biological medium comprising at least one cell population within the internal cavity; (c) operating the plurality of light sources to irradiate light into the internal cavity through said at least some of the plurality of transparent pipes, thereby growing the at least one cell population.

According to some embodiments, the process further comprises a step of removing the plurality of light sources from the transparent pipes.

According to some embodiments, the process further comprises a step of removing the proliferated cell population from the closed photobioreactor.

The term "growing" and "proliferating" as used herein are interchangeable and refer to inducing reproduction of the cell population.

According to some embodiments, step (c) is performed at a temperature in the range of 10° C. to 37° C.

According to some embodiments, step (c) comprises operating the plurality of light sources to irradiate light into the internal cavity at a wavelength in a range of 400-700 nanometers.

According to some embodiments, the process further comprises a step of inserting a cleansing composition into the internal cavity and heating the composition to a predetermined temperature.

According to some embodiments, the predetermined temperature is in the range of 120° C. to 140° C.

According to some embodiments, the step of inserting the cleansing composition into the internal cavity entails contacting the cleansing composition with an internal portion of the vessel wall and with portions of the plurality of transparent pipes.

According to some embodiments, the process further comprises a step of removing the cleansing composition from the internal cavity, thereby cleaning the closed photobioreactor.

According to some embodiments, step (b) further comprises placing nutrients for the growing of the cell population within the internal cavity.

According to some embodiments, the cell population comprises a phototrophic bio-organism species. According to some embodiments, the cell population comprises a heterotrophic bio-organism species. According to some embodiments, the cell population comprises a mixotrophic bio-organism species.

According to some embodiments, the cell population is selected from the group consisting of bacteria and algae.

According to some embodiments, the cell population comprises a phototrophic algae.

According to some embodiments, the process further comprises a step of extracting at least one material from the proliferated cell population of step (c).

According to some embodiments, there is provided a composition comprising the microorganism culture grown by the process disclosed herein, the at least one material extracted by the process disclosed herein, or a combination thereof.

Certain embodiments of the present invention may include some, all, or none of the above advantages. Further advantages may be readily apparent to those skilled in the art from the figures, descriptions, and claims included herein. Aspects and embodiments of the invention are further described in the specification herein below and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

The following embodiments and aspects thereof are described and illustrated in conjunction with systems, tools and methods which are meant to be exemplary and illustrative, but not limiting in scope. In various embodiments, one or more of the above-described problems have been reduced or eliminated, while other embodiments are directed to other advantages or improvements.

BRIEF DESCRIPTION OF THE FIGURES

Some embodiments of the disclosed technology are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures.

DETAILED DESCRIPTION OF SOME EMBODIMENTS

Figure 1A:
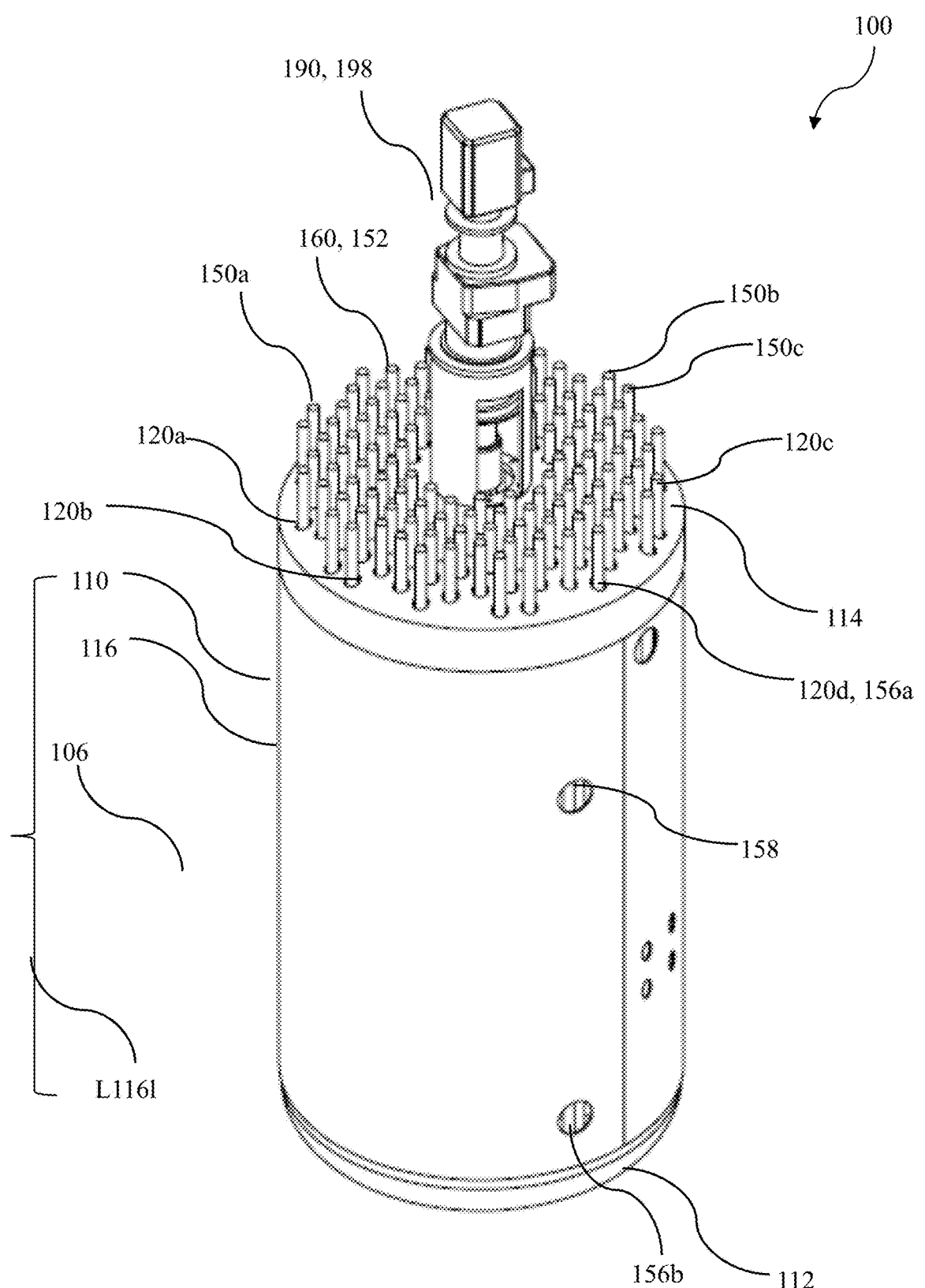
FIG. 1A constitutes a prospective view of a closed photobioreactor 100, according to some embodiments.

In the following description, various embodiments of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention. In order to avoid undue clutter from having too many reference numbers and lead lines on a particular drawing, some components will be introduced via one or more drawings and not explicitly identified in every subsequent drawing that contains that component.

Throughout the figures of the drawings, different superscripts for the same reference numerals are used to denote different embodiments of the same elements. Embodiments of the disclosed devices and systems may include any combination of different embodiments of the same elements. Specifically, any reference to an element without a superscript may refer to any alternative embodiment of the same element denoted with a superscript. Components having the same reference number followed by different lowercase letters may be collectively referred to by the reference number alone. If a particular set of components is being discussed, a reference number without a following lowercase letter may be used to refer to the corresponding component in the set being discussed. In order to avoid undue clutter from having too many reference numbers and lead lines on a particular drawing, some components will be introduced via one or more drawings and not explicitly identified in every subsequent drawing that contains that component.

Throughout the figures of the drawings, when referring to relative dimension, such as diameters, the reference numbering conventions include the uppercase D, standing for diameter or dimension, then the reference number of the relevant element and then lowercase e (if relating to an external dimension) or i (if referring to an internal dimension). For example, D999e refers to the external diameter of an element having reference number 999. The dimensions are also numbered within the figures using distant curly brackets bracketing a similar distance.

Throughout the figures of the drawings, when referring to the length of an elongated element, the reference numbering conventions include the uppercase L, standing for length, then the reference number of the relevant element and then lowercase l (if relating to a length in the longitudinal direction) or h (if relating to a length in the lateral direction). For example, L777l refers to the longitudinal length of an element having reference number 777. The lengths are also numbered within the figures using distant curly brackets bracketing a similar distance.

As used herein, the term "about" means approximately, in the region of, roughly, or around. A parameter or quantity is said to be "about", or equal to "about", a numerical value (e.g. a temperature equals about 50° C.) when it is within a range, thereby extending the boundaries above and below the numerical value. According to some embodiments, "about" is used herein to modify a numerical value above and below the stated value by a variance of 20%. According to some embodiments, "about" is used herein to modify a numerical value above and below the stated value by a variance of 10%. According to some embodiments, "about" is used herein to modify a numerical value above and below the stated value by a variance of 5%.

Figure 1B:
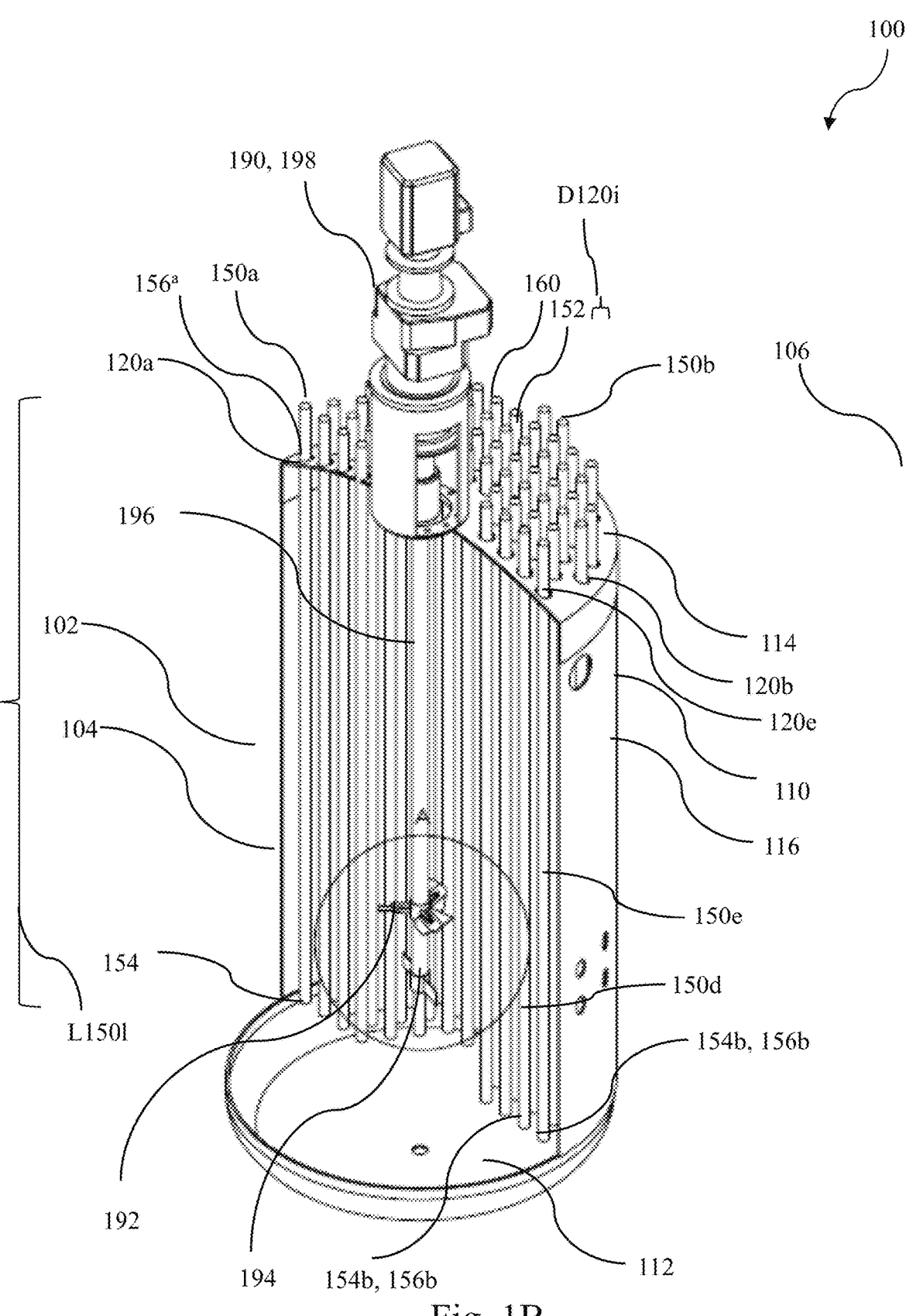
FIG. 1B constitutes a cross section view of closed photobioreactor 100 as shown in FIG. 1A, according to some embodiments.
Figure 2:
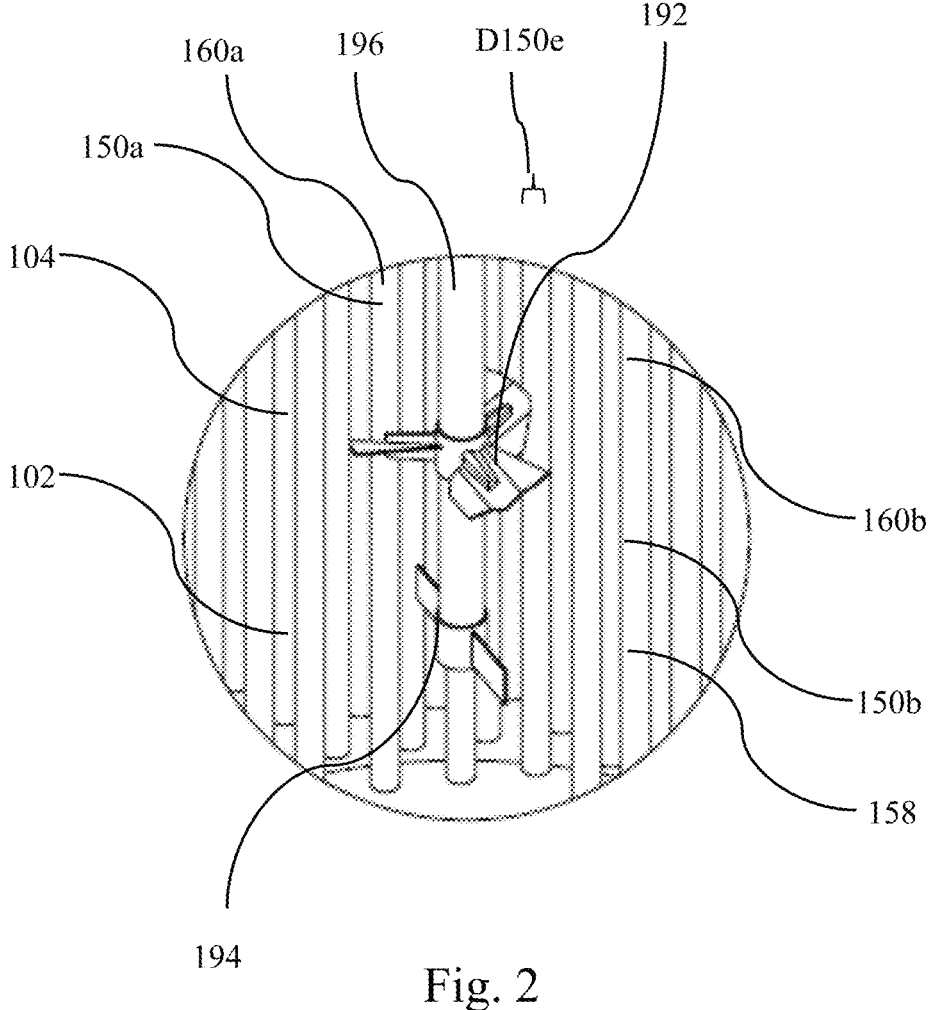
FIG. 2 constitutes close-up view of a central section of FIG. 1B, according to some embodiments.

Reference is made to FIGS. 1A, 1B and 2. FIG. 1A constitutes a prospective view of a closed photobioreactor 100. FIG. 1B constitutes a cross section view of closed photobioreactor 100 as shown in FIG. 1A. FIG. 2 constitutes close-up view of a central section of FIG. 1B.

As used herein, the term "bioreactor" refers to any system, device, apparatus or structure capable of supporting a biologically active environment and for growing organisms such as bacteria and/or algae under controlled conditions for production of products.

As used herein, the term "photobioreactor", as used herein, means a device or system used to support a biologically active environment for the cultivation of phototrophic microorganisms, including photosynthetic microorganisms. A photobioreactor may include translucent materials that permit penetration of light therethrough, and/or may incorporate a light source to provide photonic energy input for an aqueous culture of photosynthetic microorganisms contained therein.

As detailed herein, the photobioreactor of the current disclosure is configured for growing a microorganism culture in an aqueous medium. The microorganism culture may be of any microorganism species, which requires light for its cultivation, according to some embodiments. According to some embodiments, the microorganism culture is a phototroph culture. According to some embodiments, the microorganism culture is a heterotroph culture. According to some embodiments, the microorganism culture is a mixotroph culture. According to some embodiments, the microorganism culture is of a single cell species. According to some embodiments, the microorganism culture is of an algae or a bacteria. According to some embodiments, the microorganism culture is of an algae or a cyanobacteria. According to some embodiments, the microorganism culture is of a single cell algae or a single cell bacteria. According to some embodiments, the microorganism culture is of a single cell algae or a single cell cyanobacteria. According to some embodiments, the microorganism culture is an algae culture.

As used herein, the term "closed photobioreactor" refers to a closed system which at least temporarily isolates culture media contained therein from the surrounding environment. It is to be understood that closed photobioreactors may include opening(s) and/or a cover, for gaining access to the medium grown therein, and are not limited to permanently sealed or closed structures. Elements, such as a cover or a port may provide reversible access to the interior of the photobioreactor, such that its closed feature may be limited to the operation period thereof (e.g. the culture period).

Specifically, closed photobioreactor 100 disclosed herein is configured for growing a microorganism culture in an aqueous medium, according to some embodiments. According to some embodiments, closed photobioreactor 100 is configured for growing a microorganism culture in an aqueous medium.

According to some embodiments, closed photobioreactor 100 comprises a vessel 110 comprising a vessel floor 112, a vessel cover 114 and at least one vessel wall 116, and a plurality of transparent pipes 150.

Within the context of this specification, the term "longitudinal" refer to the direction from vessel floor 112 and vessel cover 114. The term "longitudinal axis" refers to the linear axis along the longitudinal direction. Similarly, the term "lateral axis" refers to the linear axis perpendicular to the longitudinal axis and the term "lateral" refer to the direction of the lateral axis.

Within the context of this specification the term "upwards" generally refers, longitudinally, to the direction from vessel floor 112 to vessel cover 114. Similarly, the term "downwards" generally refers, longitudinally, to the direction from vessel cover 114 to vessel floor 112.

Within the context of this specification the terms "top", "above", "up" and "upper" generally refer, longitudinally, to the side or end of any device or a component of a device, which is located upwards with respect to another side or end. When referring to different elements having similar name, structure or function, the terms "top", "above", "up" and "upper" generally refer, longitudinally, to the element which is located upwards with respect to the similar element.

Within the context of this specification the terms "bottom", "below", "down", "under" and "lower" generally refer, longitudinally, to the side or end of any device or a component of a device, which is located downwards with respect to another side or end. When referring to different elements having similar name, structure or function, the terms "bottom", "below", "down", "under" and "lower" generally refer, longitudinally, to the element which is located downwards with respect to the similar element.

According to some embodiments, vessel 110 is a closed vessel. According to some embodiments, vessel 110 is a reversibly closed vessel. According to some embodiments, vessel 110 is configured to be reversibly closed by vessel cover 114.

According to some embodiments, vessel 110 is made of a rigid material. According to some embodiments, vessel 110 is made of a polymer, a metal alloy or a metal. According to some embodiments, vessel 110 is made of a metal alloy. According to some embodiments, vessel 110 is made of a metal. According to some embodiments, vessel 110 is made of stainless steel.

According to some embodiments, vessel floor 112 is positioned substantially parallel to vessel cover 114. According to some embodiments, vessel floor 112 is made of a rigid material. According to some embodiments, vessel floor 112 is made of a polymer, a metal alloy or a metal. According to some embodiments, vessel floor 112 is made of a metal alloy. According to some embodiments, vessel floor 112 is made of a metal. According to some embodiments, vessel floor 112 is made of stainless steel.

According to some embodiments, vessel floor 112 has a curvilinear shape. According to some embodiments, vessel floor 112 has an ellipsoid shape. According to some embodiments, vessel floor 112 is circular.

According to some embodiments, at least one vessel wall 116 is positioned substantially perpendicular to vessel cover 114. According to some embodiments, at least one vessel wall 116 is positioned substantially perpendicular to vessel floor 112. According to some embodiments, at least one vessel wall 116 is positioned substantially perpendicular to each one of vessel cover 114 and vessel floor 112.

According to some embodiments, at least one vessel wall 116 has a closed curvilinear shape, such as a tube or a cylindroid, or rectilinear shape, such as a cuboid, including closed combinations of curvilinear and rectilinear shapes. According to some embodiments, at least one vessel wall 116 has a closed curvilinear shape. According to some embodiments, at least one vessel wall 116 is a cylindrical wall. According to some embodiments, cylindrical vessel wall 116, vessel floor 112 and vessel cover 114 of vessel 110 together form a cylindrical three dimensional structure. According to some embodiments, cylindrical vessel wall 116, vessel floor 112 and vessel cover 114 of vessel 110 together form a closed cylindrical three dimensional structure.

According to some embodiments, at least one vessel wall 116 is made of a rigid material. According to some embodiments, at least one vessel wall 116 is made of a polymer, a metal alloy or a metal. According to some embodiments, at least one vessel wall 116 is made of a metal alloy. According to some embodiments, at least one vessel wall 116 is made of a metal. According to some embodiments, at least one vessel wall 116 is made of stainless steel.

According to some embodiments, vessel floor 112, vessel cover 114 and at least one vessel wall 116 together from an internal cavity 104. According to some embodiments, vessel floor 112, vessel cover 114 and at least one vessel wall 116 together form a closed volume there within, which defines an internal cavity 104. According to some embodiments, vessel floor 112, vessel cover 114 and at least one vessel wall 116 together separate between internal cavity 104 and the surrounding environment 106 of vessel 110. According to some embodiments, vessel floor 112, vessel cover 114 and at least one vessel wall 116 together separate between internal cavity 104 and the surrounding environment 106 of closed photobioreactor 100.

It is to be understood that internal cavity 104 of vessel 110 formed between vessel floor 112, vessel cover 114 and at least one vessel wall 116 is configured for containing a microorganism culture in an aqueous medium.

FIG. 1A constitutes a perspective view of closed photobioreactor 100, in which internal cavity 104 is hidden by vessel cover 114 and at least one vessel wall 116. FIG. 1B constitutes a cross section view of closed photobioreactor 100, in which a part of at least one vessel wall 116 is not shown, such that internal cavity 104 is apparent.

According to some embodiments, vessel cover 114 has a curvilinear shape. According to some embodiments, vessel cover 114 has a an ellipsoid shape. According to some embodiments, vessel cover 114 is circular.

According to some embodiments, vessel cover 114 is configured to be positioned substantially in parallel to vessel floor 112. According to some embodiments, vessel cover 114 is positioned substantially in parallel to vessel floor 112. According to some embodiments, vessel cover 114 is configured to be positioned substantially perpendicular to at least one vessel wall 116. According to some embodiments, vessel cover 114 is positioned substantially perpendicular to at least one vessel wall 116.

According to some embodiments, vessel cover 114 is attachable to at least one vessel wall 116. According to some embodiments, vessel cover 114 is reversibly attachable to at least one vessel wall 116. According to some embodiments, vessel cover 114 is reversibly attachable to at least one vessel wall 116, such that vessel 110 is a reversibly closed chamber.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, vessel cover 114 comprises a plurality of openings 120. FIGS. 1A and 1B illustrate closed photobioreactor 100 having vessel cover 114 with about 100 openings (some of which are numbered—opening 120a, opening 120b, opening 120c, opening 120d), however closed photobioreactor 100 is not limited to this order of magnitude number of openings 120 of vessel cover 114. Specifically, according to some embodiments, vessel cover 114 comprises at least two openings. According to some embodiments, vessel cover 114 comprises at least three openings. According to some embodiments, vessel cover 114 comprises at least four openings. According to some embodiments, vessel cover 114 comprises at least five openings. According to some embodiments, vessel cover 114 comprises at least ten openings 120. According to some embodiments, vessel cover 114 comprises at least 15 openings 120. According to some embodiments, vessel cover 114 comprises at least 20 openings 120. According to some embodiments, vessel cover 114 comprises at least 25 openings 120. According to some embodiments, vessel cover 114 comprises at least 40 openings 120. According to some embodiments, vessel cover 114 comprises at least 50 openings 120. According to some embodiments, vessel cover 114 comprises at least 75 openings. According to some embodiments, vessel cover 114 comprises at least 100 openings 120.

FIGS. 1A and 1B illustrate closed photobioreactor 100 having vessel cover 114 with a plurality of openings (e.g. opening 120a, opening 120b, opening 120c, opening 120d) having a circular shape. However closed photobioreactor 100 is not limited to circular shaped openings 120 of vessel cover 114. Specifically, according to some embodiments, each one of openings 120 may have any curvilinear shape or rectilinear shape, such as a circle, an ellipsoid, a square, a rectangle, a hexagon, an octagon, etc. According to some embodiments, at least one of openings 120 is circular. According to some embodiments, each one of openings 120 is circular.

According to some embodiments, each one of transparent pipes 150 is substantially clear, such it is capable of transmitting light, such as visible light, to internal cavity 104 of vessel 110 when not disturbed by intervening objects. The term "transparent" as used herein is not limited to complete transmittance of light, as some light may scatter. Thus transparent pipe 150 may be translucent, as long as it enables a sufficient transmittance of light therethrough to internal cavity 104. According to some embodiments, transparent pipe 150 visible light has a transmittance of at least 30%, 50%, 70%, 80% or 90% through transparent pipe 150.

According to some embodiments, transparent pipe 150 is made of a transparent polymer or glass. Transparent polymers (plastics) include, but not limited to, Poly(methyl methacrylate), polycarbonates, ethylene-vinyl acetate polymer, polystyrene sulfonate, polystyrene, polypropylene and polyethylene. According to some embodiments, transparent pipe 150 is made of glass.

According to some embodiments, at least one vessel wall 116 has a longitudinal length L116$l$. According to some embodiments, longitudinal length of at least one vessel wall L116$l$ is defined between vessel floor 112 and vessel cover 114, when closed photobioreactor 100 is assembled. According to some embodiments, transparent pipe 150 has a longitudinal length L150$l$.

According to some embodiments, longitudinal length of transparent pipe L150$l$ is at least 25% compared to longitudinal length of at least one vessel wall L116$l$. According to some embodiments, longitudinal length of transparent pipe L150$l$ is at least 25% compared to longitudinal length of at least one vessel wall L116$l$. According to some embodiments, longitudinal length of transparent pipe L150$l$ is at least 33% compared to longitudinal length of at least one vessel wall L116$l$. According to some embodiments, longitudinal length of transparent pipe L150$l$ is at least 40% compared to longitudinal length of at least one vessel wall L116$l$. According to some embodiments, longitudinal length of transparent pipe L150$l$ is at least 50% compared to longitudinal length of at least one vessel wall L116$l$. According to some embodiments, longitudinal length of transparent pipe L150$l$ is at least 60% compared to longitudinal length of at least one vessel wall L116$l$. According to some embodiments, longitudinal length of transparent pipe L150$l$ is at least 70% compared to longitudinal length of at least one vessel wall L116$l$. According to some embodiments, longitudinal length of transparent pipe L150$l$ is at least 75% compared to longitudinal length of at least one vessel wall L116$l$.

According to some embodiments, longitudinal length of transparent pipe L150$l$ is not more than 300% compared to longitudinal length of at least one vessel wall L116$l$. According to some embodiments, longitudinal length of transparent pipe L150$l$ is not more than 250% compared to longitudinal length of at least one vessel wall L116$l$. According to some embodiments, longitudinal length of transparent pipe L150$l$ is not more than 200% compared to longitudinal length of at least one vessel wall L116$l$. According to some embodiments, longitudinal length of transparent pipe L150$l$ is not more than 175% compared to longitudinal length of at least one vessel wall L116$l$. According to some embodiments, longitudinal length of transparent pipe L150$l$ is not more than 150% compared to longitudinal length of at least one vessel wall L116$l$. According to some embodiments, longitudinal length of transparent pipe L150$l$ is not more than 125% compared to longitudinal length of at least one vessel wall L116$l$.

According to some embodiments, longitudinal length of transparent pipe L150$l$ is in the range of 25% to 250% compared to longitudinal length of at least one vessel wall L116$l$. According to some embodiments, longitudinal length of transparent pipe L150$l$ is in the range of 50% to 200% compared to longitudinal length of at least one vessel wall L116$l$. According to some embodiments, longitudinal length of transparent pipe L150$l$ is in the range of 75% to 150% compared to longitudinal length of at least one vessel wall L116$l$.

According to some embodiments, each one of transparent pipes 150 extends through one of openings 120.

FIGS. 1A and 1B depict closed photobioreactor 100 having about 100 transparent pipes 150 (some of which are numbered—transparent pipe 150$a$, transparent pipe 150$b$), however closed photobioreactor 100 is not limited to this order of magnitude number of transparent pipes 150. Specifically, according to some embodiments, closed photobioreactor 100 comprises at least two transparent pipes 150. Specifically, according to some embodiments, closed photobioreactor 100 comprises at least two transparent pipes 150. According to some embodiments, closed photobioreactor 100 comprises at least three transparent pipes 150. According to some embodiments, closed photobioreactor 100 comprises at least four transparent pipes 150. According to some embodiments, closed photobioreactor 100 comprises at least five transparent pipes 150. According to some embodiments, closed photobioreactor 100 comprises at least ten transparent pipes 150. According to some embodiments, closed photobioreactor 100 comprises at least 15 transparent pipes 150. According to some embodiments, closed photobioreactor 100 comprises at least 25 transparent pipes 150. According to some embodiments, closed photobioreactor 100 comprises at least 40 transparent pipes 150. According to some embodiments, closed photobioreactor 100 comprises at least 50 transparent pipes 150. According to some embodiments, closed photobioreactor 100 comprises at least 75 transparent pipes 150. According to some embodiments, closed photobioreactor 100 comprises at least 100 transparent pipes 150.

According to some embodiments, the number of transparent pipes 150 is equal to the number of openings 120 in vessel cover 114. According to some embodiments, a transparent pipes 150 extends through each one of openings 120 of vessel cover 114.

FIGS. 1A and 1B illustrate closed photobioreactor 100 having a plurality of transparent pipes 150 (e.g. transparent pipe 150$a$ and transparent pipe 150$b$) having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

According to some embodiments, transparent pipe 150 has an external diameter D150$e$ (See FIG. 2) and opening 120 has an internal diameter internal diameter of opening D120$i$. According to some embodiments, external diameter of transparent pipe D150$e$ is lower or equal to internal diameter of opening D120$i$.

According to some embodiments, each one of transparent pipes 150 is connected to vessel cover 114. According to some embodiments, each one of transparent pipes 150 is attached to vessel cover 114. According to some embodiments, each one of transparent pipes 150 is connected to one of openings 120.

According to some embodiments, each one of plurality of transparent pipes 150 has a transparent pipe first open end 152 and a transparent pipe second end 154. According to some embodiments, each one of plurality of transparent pipes 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 has a transparent pipe first open end 152 at the longitudinal top edge thereof. It is to be understood that by defining that transparent pipe first open end 152 is located out of internal cavity 104, it is not limited to a configuration in which transparent pipe first open end 152 is necessarily above vessel cover 114, according to some embodiments. Specifically, while transparent pipe first open end 152 may be offset upward from vessel cover 114, transparent pipe first open end 152 and vessel cover 114 may be substantially at the same level, such that transparent pipe first open end 152 is located out of internal cavity 104, according to some embodiments. Transparent pipe first open end 152 is located out of internal cavity 104 when transparent pipe first open end 152 is at the level of vessel cover 114, since vessel cover 114 defines the top boundary of internal cavity 104.

Figure 3A:
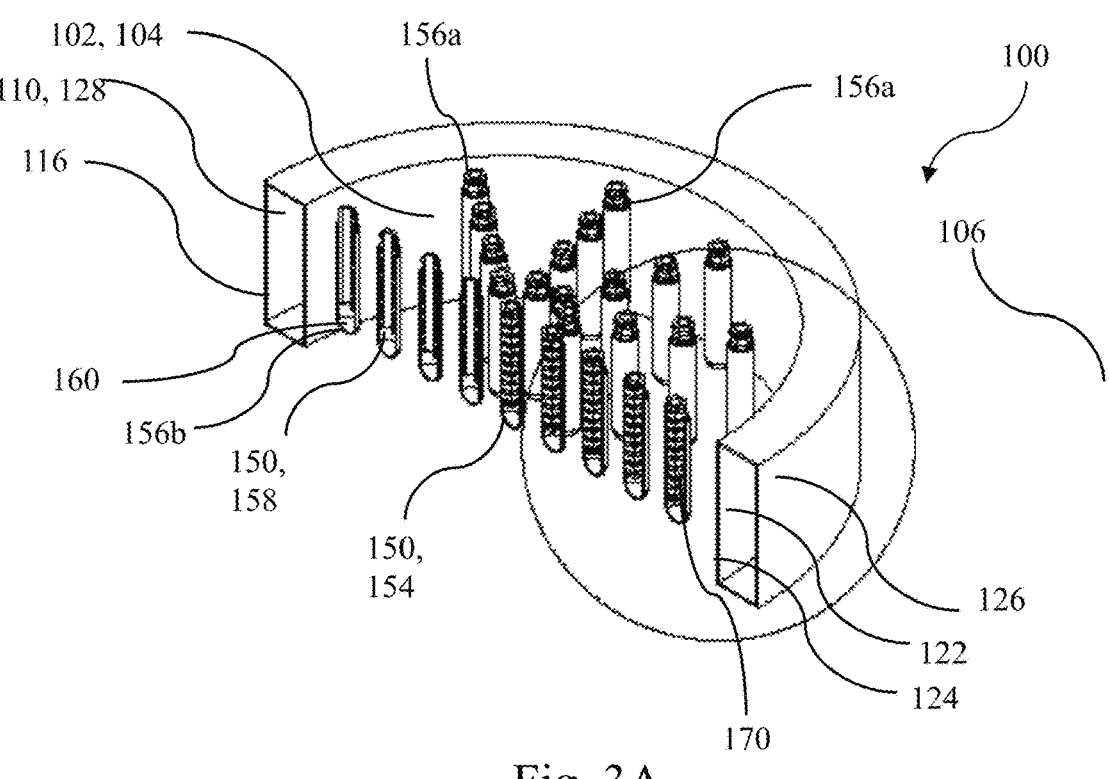
FIG. 3A constitutes a cross section view of closed photobioreactor 100, according to some embodiments.
Figure 3B:
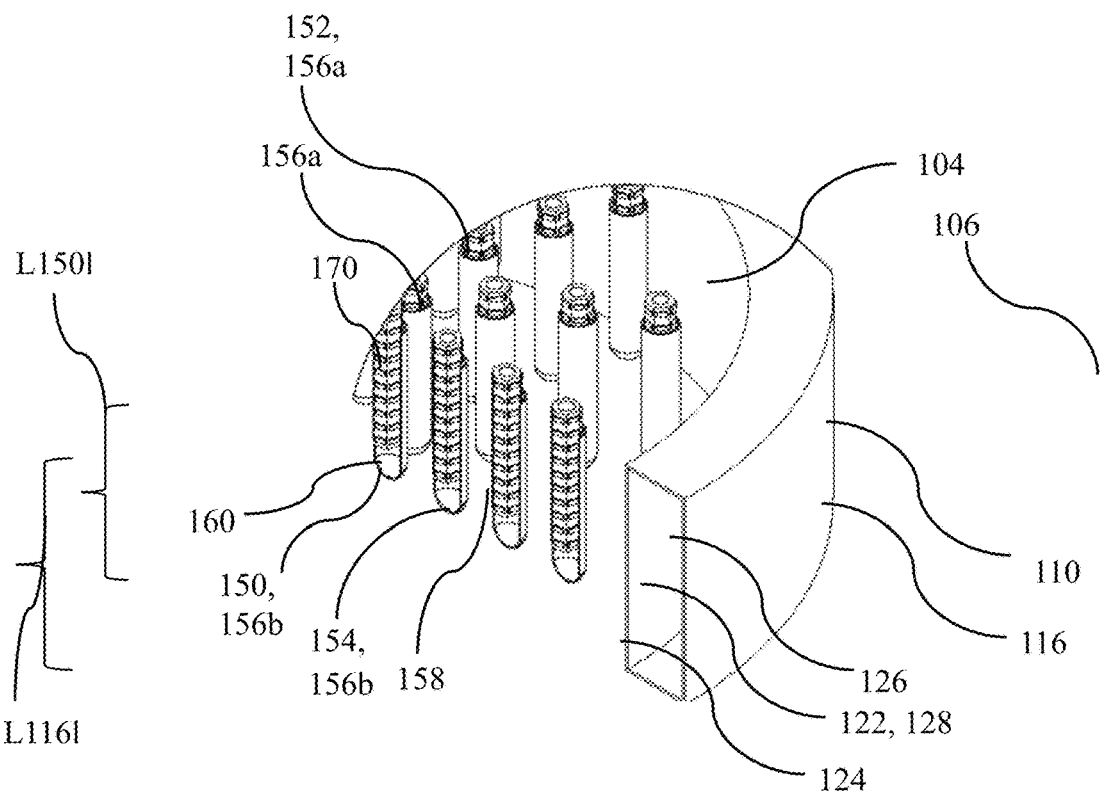
FIG. 3B constitutes close-up view of a side section of FIG. 3A, according to some embodiments.

According to some embodiments, transparent pipe first open end 152 is flush with vessel cover 114 or is offset upward from vessel cover 114. According to some embodiments, transparent pipe first open end 152 is at the level of vessel cover 114. According to some embodiments, transparent pipe first open end 152 is offset upward from vessel cover 114. Specifically, FIG. 1A and FIG. 1B represent embodiments of closed photobioreactor 100 in which transparent pipe first open end 152 is offset upward from vessel cover 114. However, closed photobioreactor 100 is not limited to transparent pipe first open ends 152, of this configuration, and FIGS. 3A, 3B represent embodiments of closed photobioreactor 100 in which transparent pipe first open end 152 is at the level of vessel cover 114. In order to exhibit this configuration clearly, vessels 110 in FIG. 3A and FIG. 3B are presented with vessel cover 114 removed or hidden from view.

According to some embodiments, each one of plurality of transparent pipes 150 defines a transparent pipe lumen 160 there inside. Specifically, it is to be understood that by the term "pipe" as used herein, it is meant to refer to the solid enclosure, rather than to elements, materials or spaces defined by its interior.

According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, transparent pipe 150 is connected to at least one of vessel cover 114 and vessel floor 112. According to some embodiments, each one of plurality of transparent pipes 150 is connected to at least one of vessel cover 114 and vessel floor 112. According to some embodiments, transparent pipe 150 is connected to one of vessel cover 114 and vessel floor 112. According to some embodiments, each one of plurality of transparent pipes 150 is connected to one of vessel cover 114 and vessel floor 112. According to some embodiments, transparent pipe 150 is connected to vessel cover 114. According to some embodiments, each one of plurality of transparent pipes 150 is connected to vessel cover 114. According to some embodiments, transparent pipe 150 is connected to vessel floor 112. According to some embodiments, each one of plurality of transparent pipes 150 is connected to vessel floor 112. For example, FIG. 1B shows transparent pipes 150a, 150b and 150c, which are connected to vessel cover 114 through respective openings 120. FIG. 1B also shows transparent pipe 150d, which is connected to vessel floor 112 and transparent pipe 150e, which is connected to both vessel floor 112 and vessel cover 114.

According to some embodiments, transparent pipe 150 has a transparent pipe first portion 156. According to some embodiments, each one of plurality of transparent pipes 150 has a transparent pipe first portion 156. According to some embodiments, transparent pipe first portion 156 is connected, directly or indirectly, to at least one of vessel cover 114 and vessel floor 112. According to some embodiments, transparent pipe first portion 156 is connected, directly or indirectly, to one of vessel cover 114 and vessel floor 112. According to some embodiments, transparent pipe first portion $156^a$ is connected, directly or indirectly, to vessel cover 114. According to some embodiments, transparent pipe first portion $156^b$ is connected, directly or indirectly, to vessel floor 112. For example, FIG. 1B shows transparent pipe 150a having transparent pipe first portion $156^a$ which is connected, directly or indirectly, to vessel cover 114 through respective opening 120a. FIG. 1B also shows transparent pipe 150d, which has transparent pipe first portion $156^b$ located at transparent pipe second end 154b thereof, which is connected, directly or indirectly, to vessel floor 112. FIG. 1B also shows transparent pipe 150e, which has transparent pipe first portion $156^b$ located at transparent pipe second end 154b thereof, which is connected, directly or indirectly, to vessel floor 112, and transparent pipe first portion $156^a$ connected, directly or indirectly, to vessel cover 114 through respective opening 120e. According to some embodiments, the connection is a direct connection. According to some embodiments, the connection is an indirect connection, though a mediating element.

According to some embodiments, transparent pipe 150 has a transparent pipe second portion 158 located within internal cavity 104 of vessel 110. According to some embodiments, each one of plurality of transparent pipes 150 has a transparent pipe second portion 158 located within internal cavity 104 of vessel 110.

Generally, vessel 110 through its surrounding components (vessel cover 114, vessel floor 112 and at least one vessel wall 116) is configured to create separation between internal cavity 104 and surrounding environment 106 of closed photobioreactor 100, according to some embodiments. Specifically, as closed photobioreactor 100 is designated for the growth of phototrophic life forms, such as algae, it is often desirable to separate their growth medium from surrounding environment 106 of closed photobioreactor 100 in order to achieve control of the environment in which the growth takes place (i.e. within internal cavity 104).

According to some embodiments, internal cavity 104 of vessel 110 contains a medium suitable for the growth of algae. According to some embodiments, According to some embodiments, internal cavity 104 of vessel 110 contains an aqueous medium 102 suitable for the growth of algae. According to some embodiments, aqueous medium 102 contains nutrients required for the growth of algae. According to some embodiments, aqueous medium 102 further contains at least one algae species.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodiments, transparent pipe 150 is substantially sealed to opening 120, such that aqueous medium 102, when inserted to vessel 110, is substantially isolated from surrounding environment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100. According to some embodiments, each one of plurality of transparent pipes 150 is substantially sealed to one of openings 120. According to some embodiments, each one of plurality of transparent pipes 150 is substantially sealed to one of openings 120, such that internal cavity 104 of vessel 110 is substantially isolated from surrounding environment 106 of closed photobioreactor 100. According to some embodiments, each one of plurality of transparent pipes 150 is substantially sealed to one of openings 120, such that aqueous medium 102, when inserted to vessel 110, is substantially isolated from surrounding environment 106 of closed photobioreactor 100. According to some embodiments, each one of plurality of transparent pipes 150 is substantially sealed to one of openings 120, such that aqueous medium 102, within vessel 110, is substantially isolated from surrounding environment 106 of closed photobioreactor 100.

The term "substantially sealed" as used herein refers to a barrier structure having a sufficiently low unintended leakage rate and/or volume under given pressure conditions. A substantially sealed device may include one or more inlet ports and/or outlet ports. A substantially sealed is relatively air- or water-tight.

Another option, encompassed by the present disclosure, according to some embodiments, to prevent contact between surrounding environment 106 and aqueous medium 102 in internal cavity 104 is to provide positive gas pressure within internal cavity 104. Specifically, such positive gas pressure may be positive inert gas pressure, such that gas leakage through plurality of openings 120 is kept in the direction out of closed photobioreactor 100, rather than inside. According to some embodiments, closed photobioreactor 100 further comprises a device configured to maintain positive pressure within vessel 110 (not shown). According to some embodiments, the device configured to maintain positive pressure within vessel 110 is a gas cylinder or a gas pump.

It is to be understood that in contrast with internal cavity 104, which is to be substantially separated from surrounding environment 106 of closed photobioreactor 100, transparent pipe lumens 160 are exposable to surrounding environment 106 of closed photobioreactor 100, according to some embodiments. Specifically, each one of plurality of transparent pipes 150 has a transparent pipe first open end 152, said open end enables exposure of the respective transparent pipe lumen 160 to surrounding environment 106 when uncapped, according to some embodiments.

According to some embodiments, transparent pipe 150 has a transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

Specifically, it is an intention of the present disclosure to provide a closed photobioreactor 100, which (a) has an internal cavity 104 substantially separated from surrounding environment 106 of closed photobioreactor 100; (b) is capable of providing sufficient illumination to aqueous medium 102 inside vessel 110; and (c) enables uncomplicated and efficient withdrawal and insertion of light sources 170 required to illuminate internal cavity 104 in different stages of operation, according to some embodiments.

According to some embodiments, transparent pipe lumen 160 is in fluid communication with surrounding environment 106 of closed photobioreactor 100, when not plugged. According to some embodiments, transparent pipe lumen 160 of each one of plurality of transparent pipes 150 is in fluid communication with surrounding environment 106 of closed photobioreactor 100, when not plugged. According to some embodiments, transparent pipe lumen 160 is in fluid communication with surrounding environment 106 of closed photobioreactor 100. According to some embodiments, transparent pipe lumen 160 of each one of plurality of transparent pipes 150 is in fluid communication with surrounding environment 106 of closed photobioreactor 100.

According to some embodiments, closed photobioreactor 100 further comprises a closed cap (not shown) configured to plug transparent pipe first open end 152. According to some embodiments, closed photobioreactor 100 further comprises a plurality of closed caps, each configured to plug transparent pipe first open end 152 of one of plurality of transparent pipes 150. Specifically, such closed caps are known in the art, and may include, but not limited to rubber plugs, plastic caps, glass caps, metal caps and wooden corks.

It is to be understood that since transparent pipe lumen 160 may come in contact with surrounding environment 106, and since aqueous medium 102 and internal cavity 104 are to be separated from surrounding environment 106, transparent pipe lumen 160 should also be separated from aqueous medium 102 and internal cavity 104 of vessel 110.

According to some embodiments, transparent pipe lumen 160 is isolated from internal cavity 104 of vessel 110. According to some embodiments, transparent pipe lumen 160 of each one of plurality of transparent pipes 150 is isolated from internal cavity 104 of vessel 110.

According to some embodiments, closed photobioreactor 100 further comprises an impeller 190 configured to stir a microorganism culture in aqueous medium 102, when aqueous medium 102 and a microorganism culture are inserted inside internal cavity 104. According to some embodiments, closed photobioreactor 100 further comprises an impeller 190 configured to stir a microorganism culture in aqueous medium 102, when aqueous medium 102 and a microorganism culture are inserted inside internal cavity 104.

According to some embodiments, impeller 190 comprises an impeller motor 198, an impeller rod 196 and at least one impeller blade. According to some embodiments, impeller 190 comprises an impeller motor 198, an impeller rod 196, a first impeller blade 192 and a second impeller blade 194.

FIGS. 1A and 1B represent an embodiment in which impeller 190 is connected to vessel cover 114 and FIG. 2 represents an enlarged central section of closed photobioreactor 100 of FIG. 1B, concentrating in the location of first impeller blade 192 and second impeller blade 194. Although these figures represent an optional embodiment, in which impeller 190 is connected to vessel cover 114, impeller 190 may be connected to another portion of vessel 110, such as vessel floor 112 or at least one vessel wall 116.

According to some embodiments, impeller 190 is connected to at least one of vessel floor 112, vessel cover 114 and at least one vessel wall 116. According to some embodiments, impeller 190 is connected to at least one of vessel floor 112 and vessel cover 114. According to some embodiments, impeller 190 is connected to vessel cover 114.

According to some embodiments, impeller motor 198 is located out of vessel 110. According to some embodiments, impeller motor 198 is configured to transform electric power to rotational movement.

According to some embodiments, at least a portion of impeller rod 196 is located within internal cavity 104 of vessel 110. According to some embodiments, impeller rod 196 extends between impeller rod 196 and internal cavity 104 of vessel 110. According to some embodiments, impeller rod 196 extends between impeller rod 196 and internal cavity 104 of vessel 110 along the longitudinal axis. According to some embodiments, impeller rod 196 is substantially parallel to at least one vessel wall 116. According to some embodiments, impeller rod 196 is substantially perpendicular to each one of vessel floor 112 and vessel cover 114.

According to some embodiments, impeller rod 196 is connected to impeller motor 198. According to some embodiments, impeller rod 196 is connected to impeller motor 198, such that impeller motor 198 is configured to impart the rotational movement to impeller rod 196.

According to some embodiments, impeller rod 196 is connected to the at least one impeller blade. According to some embodiments, impeller rod 196 is connected to first impeller blade 192. According to some embodiments, impeller rod 196 is connected to second impeller blade 194.

According to some embodiments, impeller rod 196 is connected to both first impeller blade 192 and second impeller blade 194.

According to some embodiments, the at least one impeller blade is located within internal cavity 104 of vessel 110. According to some embodiments, first impeller blade 192 is located within internal cavity 104 of vessel 110. According to some embodiments, second impeller blade 194 is located within internal cavity 104 of vessel 110. According to some embodiments, each one of first impeller blade 192 and second impeller blade 194 is located within internal cavity 104 of vessel 110.

According to some embodiments, impeller motor 198 is configured to impart the rotational movement to impeller rod 196, thereby rotating the at least one impeller blade. According to some embodiments, impeller motor 198 is configured to impart the rotational movement to impeller rod 196, thereby rotating first impeller blade 192. According to some embodiments, impeller motor 198 is configured to impart the rotational movement to impeller rod 196, thereby rotating second impeller blade 194. According to some embodiments, impeller motor 198 is configured to impart the rotational movement to impeller rod 196, thereby rotating first impeller blade 192 and second impeller blade 194.

According to some embodiments, the rotation of the at least one impeller blade creates turbulence within internal cavity 104 of vessel 110, when aqueous medium 102 is present inside vessel 110.

Reference is made to FIGS. 3A and 3B. FIG. 3A constitutes a cross section view of closed photobioreactor 100. FIG. 3B constitutes close-up view of a side section of FIG. 3A.

Closed photobioreactor 100 disclosed herein is configured for growing a microorganism culture in an aqueous medium, according to some embodiments. According to some embodiments, closed photobioreactor 100 is configured for growing a microorganism culture in an aqueous medium.

According to some embodiments, closed photobioreactor 100 comprises a vessel 110 comprising a vessel floor 112, a vessel cover 114 and at least one vessel wall 116, and a plurality of transparent pipes 150. While vessel floor 112 and vessel cover 114 are hidden from view in FIGS. 3A and 3B for presentation purposes of other elements, it will be appreciated that vessel floor 112 and vessel cover 114 are present in closed photobioreactor 100 of FIGS. 3A and 3B, and have similar relations with vessel 110, at least one vessel wall 116, aqueous medium 102, internal cavity 104 and surrounding environment 106 as described when referring to FIGS. 1A, 1B and 2.

According to some embodiments, vessel 110 is a closed vessel. According to some embodiments, vessel 110 is a reversibly closed vessel. According to some embodiments, vessel 110 is configured to be reversibly closed by vessel cover 114.

According to some embodiments, vessel 110 is made of a rigid material. According to some embodiments, vessel 110 is made of a polymer, a metal alloy or a metal. According to some embodiments, vessel 110 is made of a metal alloy. According to some embodiments, vessel 110 is made of a metal. According to some embodiments, vessel 110 is made of stainless steel.

According to some embodiments, vessel floor 112 is positioned substantially parallel to vessel cover 114. According to some embodiments, vessel floor 112 is made of a rigid material. According to some embodiments, vessel floor 112 is made of a polymer, a metal alloy or a metal. According to some embodiments, vessel floor 112 is made of a metal alloy. According to some embodiments, vessel floor 112 is made of a metal. According to some embodiments, vessel floor 112 is made of stainless steel.

According to some embodiments, vessel floor 112 has a curvilinear shape.

According to some embodiments, vessel floor 112 has a an ellipsoid shape. According to some embodiments, vessel floor 112 is circular.

According to some embodiments, at least one vessel wall 116 is positioned substantially perpendicular to vessel cover 114. According to some embodiments, at least one vessel wall 116 is positioned substantially perpendicular to vessel floor 112. According to some embodiments, at least one vessel wall 116 is positioned substantially perpendicular to each one of vessel cover 114 and vessel floor 112.

According to some embodiments, at least one vessel wall 116 has a closed curvilinear shape, such as a tube or a cylindroid, or rectilinear shape, such as a cuboid, including closed combinations of curvilinear and rectilinear shapes. According to some embodiments, at least one vessel wall 116 has a closed curvilinear shape. According to some embodiments, at least one vessel wall 116 is a cylindrical wall. According to some embodiments, cylindrical vessel wall 116, vessel floor 112 and vessel cover 114 of vessel 110 together form a cylindrical three dimensional structure. According to some embodiments, cylindrical vessel wall 116, vessel floor 112 and vessel cover 114 of vessel 110 together form a closed cylindrical three dimensional structure.

According to some embodiments, at least one vessel wall 116 is a double walled cooling jacket 122. According to some embodiments, at least one vessel wall 116 is a cylindrical double walled cooling jacket 122.

According to some embodiments, double walled cooling jacket 122 comprises at least one cooling jacket internal wall 124 and at least one cooling jacket external wall 126. According to some embodiments, at least one cooling jacket internal wall 124 is bounding internal cavity 104 of vessel 110. According to some embodiments, at least one cooling jacket internal wall 124 and at least one cooling jacket external wall 126 are spaced apart. According to some embodiments, at least one cooling jacket internal wall 124 and at least one cooling jacket external wall 126 are spaced apart to form a lumen there between.

According to some embodiments, double walled cooling jacket 122 further comprises a vessel cooling liquid 128. According to some embodiments, vessel cooling liquid 128 is located between at least one cooling jacket internal wall 124 and at least one cooling jacket external wall 126.

According to some embodiments, vessel cooling liquid 128 comprises water.

According to some embodiments, closed photobioreactor 100 further comprises a device configured to circulate vessel cooling liquid 128 inside double walled cooling jacket 122 and through a liquid cooling mechanism (not shown). According to some embodiments, the liquid cooling mechanism is external to closed photobioreactor 100. According to some embodiments, the device configured to circulate vessel cooling liquid 128 is a liquid pump (not shown)

According to some embodiments, at least one vessel wall 116 is made of a rigid material. According to some embodiments, at least one vessel wall 116 is made of a polymer, a metal alloy or a metal. According to some embodiments, at least one vessel wall 116 is made of a metal alloy. According to some embodiments, at least one vessel wall 116 is made of a metal. According to some embodiments, at least one vessel wall 116 is made of stainless steel.

According to some embodiments, vessel floor 112, vessel cover 114 and at least one vessel wall 116 together from an internal cavity 104. According to some embodiments, vessel floor 112, vessel cover 114 and at least one vessel wall 116 together form a closed volume there within, which defines an internal cavity 104. According to some embodiments, vessel floor 112, vessel cover 114 and at least one vessel wall 116 together separate between internal cavity 104 and the surrounding environment 106 of vessel 110. According to some embodiments, vessel floor 112, vessel cover 114 and at least one vessel wall 116 together separate between internal cavity 104 and the surrounding environment 106 of closed photobioreactor 100.

It is to be understood that internal cavity 104 of vessel 110 formed between vessel floor 112, vessel cover 114 and at least one vessel wall 116 is configured for containing a microorganism culture in an aqueous medium.

FIG. 3A constitutes a cross section view of closed photobioreactor 100, in which vessel cover 114, vessel floor 112 and a part of at least one vessel wall 116 is not shown, such that internal cavity 104 is apparent.

According to some embodiments, vessel cover 114 has a curvilinear shape. According to some embodiments, vessel cover 114 has an ellipsoid shape. According to some embodiments, vessel cover 114 is circular.

According to some embodiments, vessel cover 114 is configured to be positioned substantially in parallel to vessel floor 112. According to some embodiments, vessel cover 114 is positioned substantially in parallel to vessel floor 112. According to some embodiments, vessel cover 114 is configured to be positioned substantially perpendicular to at least one vessel wall 116. According to some embodiments, vessel cover 114 is positioned substantially perpendicular to at least one vessel wall 116.

According to some embodiments, vessel cover 114 is attachable to at least one vessel wall 116. According to some embodiments, vessel cover 114 is reversibly attachable to at least one vessel wall 116. According to some embodiments, vessel cover 114 is reversibly attachable to at least one vessel wall 116, such that vessel 110 is a reversibly closed chamber.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, vessel cover 114 comprises a plurality of openings 120. Since vessel cover 114 is not shown in FIGS. 3A and 3B for presentation reasons as detailed above, openings 120 of vessel cover 114 are not apparent in FIGS. 3A and 3B. However, reference to vessel cover 114 of closed photobioreactor 100 of FIGS. 3A and 3B is already made when describing FIGS. 1A and 1B. Thus, embodiments referring to vessel cover 114 and openings 120 of FIGS. 3A and 3B are as presented in the description to FIGS. 1A and 1B.

Specifically, according to some embodiments, vessel cover 114 comprises at least two openings. According to some embodiments, vessel cover 114 comprises at least three openings. According to some embodiments, vessel cover 114 comprises at least four openings. According to some embodiments, vessel cover 114 comprises at least five openings. According to some embodiments, vessel cover 114 comprises at least ten openings 120. According to some embodiments, vessel cover 114 comprises at least 15 openings 120. According to some embodiments, vessel cover 114 comprises at least 20 openings 120. According to some embodiments, vessel cover 114 comprises at least 25 openings 120. According to some embodiments, vessel cover 114 comprises at least 40 openings 120. According to some embodiments, vessel cover 114 comprises at least 50 openings 120. According to some embodiments, vessel cover 114 comprises at least 75 openings. According to some embodiments, vessel cover 114 comprises at least 100 openings 120.

In addition, according to some embodiments, each one of openings 120 may have any curvilinear shape or rectilinear shape, such as a circle, an ellipsoid, a square, a rectangle, a hexagon, an octagon, etc. According to some embodiments, at least one of openings 120 is circular. According to some embodiments, each one of openings 120 is circular.

According to some embodiments, each one of transparent pipes 150 is substantially clear, such it is capable of transmitting light, such as visible light, to internal cavity 104 of vessel 110 when not disturbed by intervening objects. According to some embodiments, transparent pipe 150 may be translucent, as long as it enables a sufficient transmittance of light therethrough to internal cavity 104. According to some embodiments, transparent pipe 150 visible light has a transmittance of at least 30%, 50%, 70%, 80% or 90% through transparent pipe 150.

According to some embodiments, transparent pipe 150 is made of a transparent polymer or glass. Transparent polymers (plastics) include, but not limited to, Poly(methyl methacrylate), polycarbonates, ethylene-vinyl acetate polymer, polystyrene sulfonate, polystyrene, polypropylene and polyethylene. According to some embodiments, transparent pipe 150 is made of glass.

According to some embodiments, at least one vessel wall 116 has a longitudinal length L116$l$. According to some embodiments, longitudinal length of at least one vessel wall L116$l$ is defined between vessel floor 112 and vessel cover 114, when closed photobioreactor 100 is assembled. According to some embodiments, transparent pipe 150 has a longitudinal length L150$l$.

According to some embodiments, longitudinal length of transparent pipe L150$l$ is at least 25% compared to longitudinal length of at least one vessel wall L116$l$. According to some embodiments, longitudinal length of transparent pipe L150$l$ is at least 25% compared to longitudinal length of at least one vessel wall L116$l$. According to some embodiments, longitudinal length of transparent pipe L150$l$ is at least 33% compared to longitudinal length of at least one vessel wall L116$l$. According to some embodiments, longitudinal length of transparent pipe L150$l$ is at least 40% compared to longitudinal length of at least one vessel wall L116$l$. According to some embodiments, longitudinal length of transparent pipe L150$l$ is at least 50% compared to longitudinal length of at least one vessel wall L116$l$. According to some embodiments, longitudinal length of transparent pipe L150$l$ is at least 60% compared to longitudinal length of at least one vessel wall L116$l$. According to some embodiments, longitudinal length of transparent pipe L150$l$ is at least 70% compared to longitudinal length of at least one vessel wall L116$l$. According to some embodiments, longitudinal length of transparent pipe L150$l$ is at least 75% compared to longitudinal length of at least one vessel wall L116$l$.

According to some embodiments, longitudinal length of transparent pipe L150$l$ is not more than 300% compared to longitudinal length of at least one vessel wall L116$l$. According to some embodiments, longitudinal length of transparent pipe L150*l* is not more than 250% compared to longitudinal length of at least one vessel wall L116*l*. According to some embodiments, longitudinal length of transparent pipe L150*l* is not more than 200% compared to longitudinal length of at least one vessel wall L116*l*. According to some embodiments, longitudinal length of transparent pipe L150*l* is not more than 175% compared to longitudinal length of at least one vessel wall L116*l*. According to some embodiments, longitudinal length of transparent pipe L150*l* is not more than 150% compared to longitudinal length of at least one vessel wall L116*l*. According to some embodiments, longitudinal length of transparent pipe L150*l* is not more than 125% compared to longitudinal length of at least one vessel wall L116*l*. According to some embodiments, longitudinal length of transparent pipe L150*l* is not more than longitudinal length of at least one vessel wall L116*l*. According to some embodiments, longitudinal length of transparent pipe L150*l* is shorter than longitudinal length of at least one vessel wall L116*l*. Specifically, in FIGS. 3A and 3B longitudinal length of transparent pipe L150*l* is shorter than longitudinal length of at least one vessel wall L116*l*, however, closed photobioreactor 100 is not limited to such configuration.

According to some embodiments, longitudinal length of transparent pipe L150*l* is in the range of 25% to 250% compared to longitudinal length of at least one vessel wall L116*l*. According to some embodiments, longitudinal length of transparent pipe L150*l* is in the range of 50% to 200% compared to longitudinal length of at least one vessel wall L116*l*. According to some embodiments, longitudinal length of transparent pipe L150*l* is in the range of 75% to 110% compared to longitudinal length of at least one vessel wall L116*l*.

According to some embodiments, each one of transparent pipes 150 pipes extends through one of openings 120.

FIGS. 3A and 3B depict closed photobioreactor 100 having about 25 transparent pipes 150, however closed photobioreactor 100 is not limited to this order of magnitude number of transparent pipes 150. Specifically, according to some embodiments, closed photobioreactor 100 comprises at least two transparent pipes 150. Specifically, according to some embodiments, closed photobioreactor 100 comprises at least two transparent pipes 150. According to some embodiments, closed photobioreactor 100 comprises at least three transparent pipes 150. According to some embodiments, closed photobioreactor 100 comprises at least four transparent pipes 150. According to some embodiments, closed photobioreactor 100 comprises at least five transparent pipes 150. According to some embodiments, closed photobioreactor 100 comprises at least ten transparent pipes 150. According to some embodiments, closed photobioreactor 100 comprises at least 15 transparent pipes 150. According to some embodiments, closed photobioreactor 100 comprises at least 25 transparent pipes 150. According to some embodiments, closed photobioreactor 100 comprises at least 40 transparent pipes 150. According to some embodiments, closed photobioreactor 100 comprises at least 50 transparent pipes 150. According to some embodiments, closed photobioreactor 100 comprises at least 75 transparent pipes 150. According to some embodiments, closed photobioreactor 100 comprises at least 100 transparent pipes 150.

According to some embodiments, the number of transparent pipes 150 is equal to the number of openings 120 in vessel cover 114. According to some embodiments, a transparent pipes 150 extends through each one of openings 120 of vessel cover 114.

FIGS. 3A and 3B illustrate closed photobioreactor 100 having a plurality of transparent pipes 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

According to some embodiments, each one of transparent pipes 150 is connected to vessel cover 114. According to some embodiments, each one of transparent pipes 150 is attached to vessel cover 114. According to some embodiments, each one of transparent pipes 150 is connected to one of openings 120.

According to some embodiments, each one of plurality of transparent pipes 150 has a transparent pipe first open end 152 and a transparent pipe second end 154. According to some embodiments, each one of plurality of transparent pipes 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 has a transparent pipe first open end 152 at the longitudinal top edge thereof. It is to be understood that by defining that transparent pipe first open end 152 is located out of internal cavity 104, it is not limited to a configuration in which transparent pipe first open end 152 is necessarily above vessel cover 114, according to some embodiments. Specifically, while transparent pipe first open end 152 may be offset upward from vessel cover 114, transparent pipe first open end 152 and vessel cover 114 may be substantially at the same level, such that transparent pipe first open end 152 is located out of internal cavity 104, according to some embodiments. Transparent pipe first open end 152 is located out of internal cavity 104 when transparent pipe first open end 152 is at the level of vessel cover 114, since vessel cover 114 defines the top boundary of internal cavity 104.

According to some embodiments, transparent pipe first open end 152 is flush with vessel cover 114 or is offset upward from vessel cover 114. According to some embodiments, transparent pipe first open end 152 is at the level of vessel cover 114. According to some embodiments, transparent pipe first open end 152 is offset upward from vessel cover 114. Specifically, FIG. 3A and FIG. 3B represent embodiments of closed photobioreactor 100 in which transparent pipe first open end 152 is at the level of vessel cover 114. However, closed photobioreactor 100 is not limited to transparent pipe first open ends 152, of this configuration, as shown in FIGS. 1A and 1B. In order to exhibit this configuration clearly, vessel 110 in FIG. 3A and FIG. 3B is presented with vessel cover 114 hidden from view.

According to some embodiments, each one of plurality of transparent pipes 150 defines a transparent pipe lumen 160 there inside.

According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, transparent pipe 150 is accommodating a light source 170 within transparent pipe lumen 160 thereof. Specifically, light source 170 and its interaction with transparent pipe 150 is described with greater detail when referring to FIGS. 5A-E and 8A-B. According to some embodiments, plurality of transparent pipes 150 are accommodating plurality of light sources 170 source within transparent pipe lumens 160 thereof. According to some embodiments, upon the accommodation, a positive gap (see positive gap 172 in FIGS. 5A-E) between the internal diameter of the transparent pipe and the external dimensions of the light source exists. According to some embodiments, each of plurality of light sources 170 is drawable from transparent pipe 150, which accommodates it.

According to some embodiments, transparent pipe 150 is connected to at least one of vessel cover 114 and vessel floor 112. According to some embodiments, each one of plurality of transparent pipes 150 is connected to at least one of vessel cover 114 and vessel floor 112. According to some embodiments, transparent pipe 150 is connected to one of vessel cover 114 and vessel floor 112. According to some embodiments, each one of plurality of transparent pipes 150 is connected to one of vessel cover 114 and vessel floor 112. According to some embodiments, transparent pipe 150 is connected to vessel cover 114. According to some embodiments, each one of plurality of transparent pipes 150 is connected to vessel cover 114. According to some embodiments, transparent pipe 150 is connected to vessel floor 112. According to some embodiments, each one of plurality of transparent pipes 150 is connected to vessel floor 112. Although FIGS. 3A and 3B are depicted with vessel floor 112 and vessel cover 114 hidden, it is to be understood that their structure, configurations and interaction with transparent pipe 150 are similar to those described when referring to FIGS. 1A and 1B.

According to some embodiments, transparent pipe 150 has a transparent pipe first portion 156. According to some embodiments, each one of plurality of transparent pipes 150 has a transparent pipe first portion 156. According to some embodiments, transparent pipe first portion 156 is connected, directly or indirectly, to at least one of vessel cover 114 and vessel floor 112. According to some embodiments, transparent pipe first portion 156 is connected to one of vessel cover 114 and vessel floor 112. According to some embodiments, transparent pipe first portion 156$^a$ is connected to vessel cover 114. According to some embodiments, transparent pipe first portion 156$^b$ is connected to vessel floor 112. Although FIGS. 3A and 3B are depicted with vessel floor 112 and vessel cover 114 hidden, it is to be understood that their structure, configurations and interaction with transparent pipe first portion 156$^a$ and transparent pipe first portion 156$^b$ are similar to those described when referring to FIGS. 1A and 1B.

According to some embodiments, transparent pipe 150 has a transparent pipe second portion 158 located within internal cavity 104 of vessel 110. According to some embodiments, each one of plurality of transparent pipes 150 has a transparent pipe second portion 158 located within internal cavity 104 of vessel 110.

As detailed with respect to closed photobioreactor 100 of FIGS. 1A and 1B, vessel 110 is configured to create separation between internal cavity 104 and surrounding environment 106 of closed photobioreactor 100, according to some embodiments.

According to some embodiments, internal cavity 104 of vessel 110 contains a medium suitable for the growth of algae. According to some embodiments, internal cavity 104 of vessel 110 contains an aqueous medium 102 suitable for the growth of algae. According to some embodiments, aqueous medium 102 contains nutrients required for the growth of algae. According to some embodiments, aqueous medium 102 further contains at least one algae species.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodiments, transparent pipe 150 is substantially sealed to opening 120, such that aqueous medium 102, when inserted to vessel 110, is substantially isolated from surrounding environment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100. According to some embodiments, each one of plurality of transparent pipes 150 is substantially sealed to one of openings 120. According to some embodiments, each one of plurality of transparent pipes 150 is substantially sealed to one of openings 120, such that internal cavity 104 of vessel 110 is substantially isolated from surrounding environment 106 of closed photobioreactor 100. According to some embodiments, each one of plurality of transparent pipes 150 is substantially sealed to one of openings 120, such that aqueous medium 102, when inserted to vessel 110, is substantially isolated from surrounding environment 106 of closed photobioreactor 100. According to some embodiments, each one of plurality of transparent pipes 150 is substantially sealed to one of openings 120, such that aqueous medium 102, within vessel 110, is substantially isolated from surrounding environment 106 of closed photobioreactor 100.

According to some embodiments, closed photobioreactor 100 further comprises a device configured to maintain positive pressure within vessel 110 (not shown). According to some embodiments, the device configured to maintain positive pressure within vessel 110 is a gas cylinder or a gas pump.

It is to be understood that in contrast with internal cavity 104, which is to be substantially separated from surrounding environment 106 of closed photobioreactor 100, transparent pipe lumens 160 are exposable to surrounding environment 106 of closed photobioreactor 100, according to some embodiments. Specifically, each one of plurality of transparent pipes 150 has a transparent pipe first open end 152, said open end enables exposure of the respective transparent pipe lumen 160 to surrounding environment 106 when uncapped, according to some embodiments.

According to some embodiments, transparent pipe 150 has a transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

Specifically, it is an intention of the present disclosure to provide a closed photobioreactor 100, which (a) has an internal cavity 104 substantially separated from surrounding environment 106 of closed photobioreactor 100; (b) is capable of providing sufficient illumination to aqueous medium 102 inside vessel 110; and (c) enables uncomplicated and efficient withdrawal and insertion of light sources 170 required to illuminate internal cavity 104 in different stages of operation.

According to some embodiments, transparent pipe lumen 160 is in fluid communication with surrounding environment 106 of closed photobioreactor 100, when not plugged. According to some embodiments, transparent pipe lumen 160 of each one of plurality of transparent pipes 150 is in fluid communication with surrounding environment 106 of closed photobioreactor 100, when not plugged. According to some embodiments, transparent pipe lumen 160 is in fluid communication with surrounding environment 106 of closed photobioreactor 100. According to some embodiments, transparent pipe lumen 160 of each one of plurality of transparent pipes 150 is in fluid communication with surrounding environment 106 of closed photobioreactor 100.

According to some embodiments, closed photobioreactor 100 further comprises a closed cap (not shown) configured to plug transparent pipe first open end 152. According to some embodiments, closed photobioreactor 100 further comprises a plurality of closed caps, each configured to plug transparent pipe first open end 152 of one of plurality of transparent pipes 150. Specifically, such closed caps are known in the art, and may include, but not limited to rubber plugs, plastic caps, glass caps, metal caps and wooden corks.

It is to be understood that since transparent pipe lumen 160 may come in contact with surrounding environment 106, and since aqueous medium 102 and internal cavity 104 are to be separated from surrounding environment 106, transparent pipe lumen 160 should also be separated from aqueous medium 102 and internal cavity 104 of vessel 110.

According to some embodiments, transparent pipe lumen 160 is isolated from internal cavity 104 of vessel 110. According to some embodiments, transparent pipe lumen 160 of each one of plurality of transparent pipes 150 is isolated from internal cavity 104 of vessel 110.

According to some embodiments, closed photobioreactor 100 further comprises an impeller 190 configured to stir a microorganism culture in aqueous medium 102, when aqueous medium 102 and a microorganism culture are inserted inside internal cavity 104. Impeller 190 is not shown in FIGS. 3A and 3B, however, it is to be understood that a similar impeller 190 to the one disclosed when referring to closed photobioreactor 100 of FIGS. 1A-B may be used for closed photobioreactor 100 of FIGS. 3A-B.

Figures 4A, 4B:
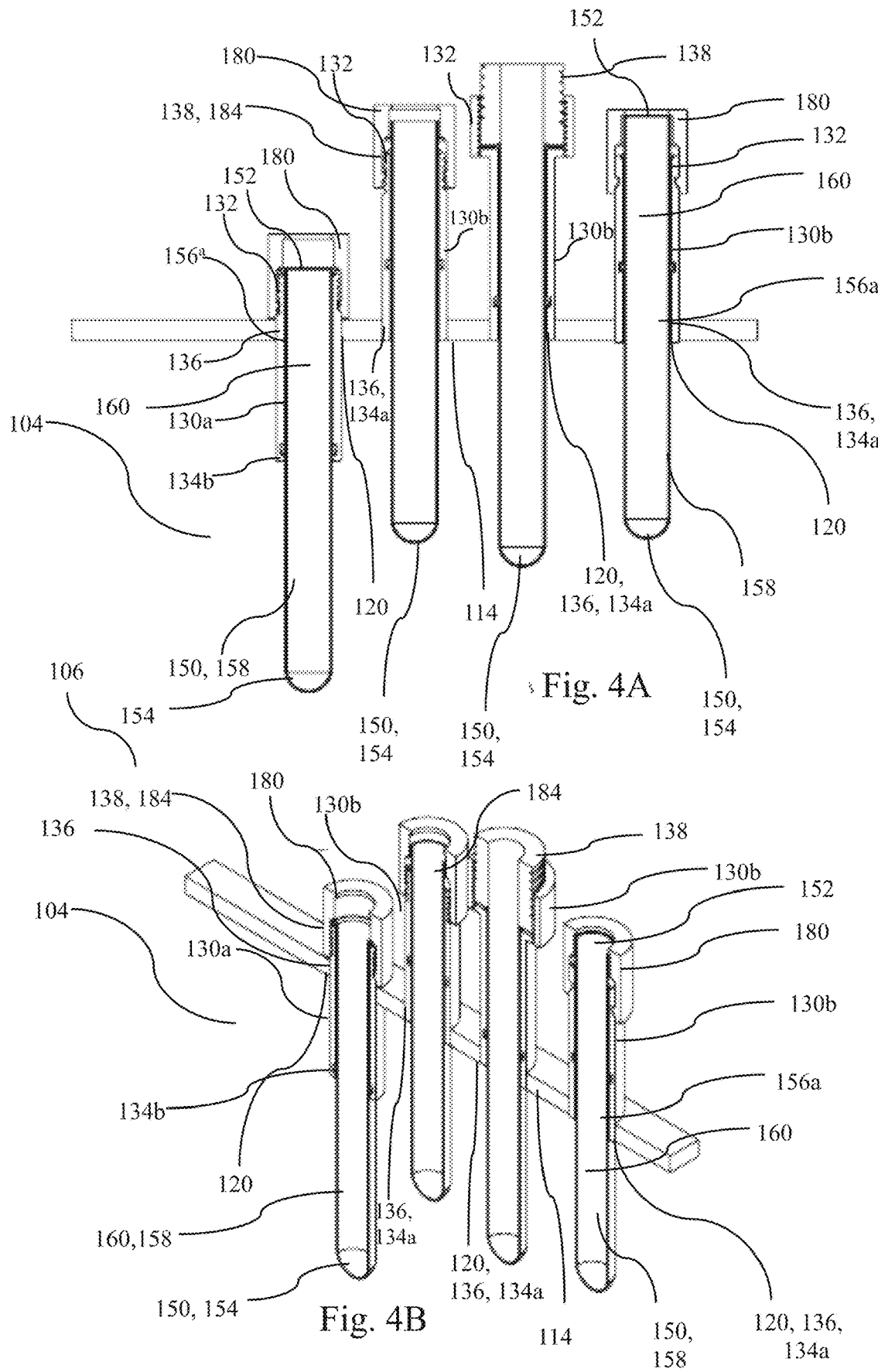
FIG. 4A constitutes a front cross section view of vessel cover 114 of closed photobioreactor 100, according to some embodiments.
FIG. 4B constitutes a diagonal sectional view in perspective of vessel cover 114 of closed photobioreactor 100, according to some embodiments.

Reference is made to FIGS. 4A and 4B. FIG. 4A constitutes a front cross section view of vessel cover 114 of closed photobioreactor 100, according to some embodiments. FIG. 4B constitutes a diagonal sectional view in perspective of vessel cover 114 of closed photobioreactor 100, according to some embodiments.

Vessel cover 114 as shown in FIG. 4A and FIG. 4B may be used as vessel cover 114 of closed photobioreactor 100 of FIGS. 1A-B and/or as vessel cover 114 of closed photobioreactor 100 of FIGS. 3A-B. Specifically, the embodiments depicted in FIGS. 4A-B relate to an optional means of connecting between transparent pipe 150 and vessel cover 114, a connection which is introduced when describing FIGS. 1A, 1B, 3A and 3B hereinabove.

According to some embodiments, vessel cover 114 comprises a plurality of hollow cover extensions 130.

According to some embodiments, at least one of plurality of hollow cover extensions 130 is extending from one of openings 120 upward. According to some embodiments, each one of plurality of hollow cover extensions 130 is extending from one of openings 120 upward.

According to some embodiments, at least one of plurality of hollow cover extensions 130 is extending from one of openings 120 upward towards surrounding environment 106 of closed photobioreactor 100. According to some embodiments, each one of plurality of hollow cover extensions 130 is extending from one of openings 120 upward towards surrounding environment 106 of closed photobioreactor 100.

For example, three of plurality of hollow cover extensions 130 shown in FIGS. 4A and 4B are portrayed as extending from opening 120 upward, and are numbered 130[b].

According to some embodiments, at least one of plurality of hollow cover extensions 130 is extending from internal cavity 104, through one of openings 120 upward. According to some embodiments, each one of plurality of hollow cover extensions 130 is extending from internal cavity 104, through one of openings 120 upward.

According to some embodiments, at least one of plurality of hollow cover extensions 130 is extending from internal cavity 104, through one of openings 120 upward towards surrounding environment 106 of closed photobioreactor 100. According to some embodiments, each one of plurality of hollow cover extensions 130 is extending from internal cavity 104, through one of openings 120 upward towards surrounding environment 106 of closed photobioreactor 100.

For example, one of plurality of hollow cover extensions 130 shown in FIGS. 4A and 4B is portrayed as extending from internal cavity 104 upward towards surrounding environment 106 of closed photobioreactor 100, and is numbered 130[b].

According to some embodiments, at least one of plurality of hollow cover extensions 130 is extending downward from one of openings 120 towards internal cavity 104. According to some embodiments, each one of plurality of hollow cover extensions 130 is extending downward from one of openings 120 towards internal cavity 104.

As detailed herein above, the up or upward direction is the direction from vessel floor 112 toward vessel cover 114. Thus, extending upwards from vessel cover 114 leads to surrounding environment 106 of closed photobioreactor 100.

According to some embodiments, transparent pipe 150 is extending through hollow cover extension 130. According to some embodiments, each one of plurality of transparent pipes 150 is extending through one of plurality of hollow cover extensions 130.

According to some embodiments, transparent pipe 150 is retained by hollow cover extension 130. According to some embodiments, each one of plurality of transparent pipes 150 is retained by one of plurality of hollow cover extensions 130. According to some embodiments, transparent pipe 150 is connected to hollow cover extension 130. According to some embodiments, each one of plurality of transparent pipes 150 is connected to one of plurality of hollow cover extensions 130. According to some embodiments, transparent pipe 150 is sealed to hollow cover extension 130. According to some embodiments, each one of plurality of transparent pipes 150 is sealed to one of plurality of hollow cover extensions 130.

According to some embodiments, hollow cover extension 130 comprises a hollow cover extension first open end 132. According to some embodiments, each hollow cover extension 130 comprises a hollow cover extension first open end 132. According to some embodiments, hollow cover extension first open end 132 is offset upward from vessel cover 114. According to some embodiments, hollow cover extension first open end 132 is at the level of vessel cover 114. According to some embodiments, hollow cover extension first open end 132 is at the level of openings 120.

As detailed herein, it is an intention of the present disclosure to provide a closed photobioreactor 100, which (a) has an internal cavity 104 substantially separated from surrounding environment 106 of closed photobioreactor 100; (b) is capable of providing sufficient illumination to aqueous medium 102 inside vessel 110; and (c) enables uncomplicated and efficient withdrawal and insertion of light sources 170 required to illuminate internal cavity 104 in different stages of operation, according to some embodiments. In order to fulfill requirement (c), transparent pipe 150 is provided with transparent pipe first open end 152, and hollow cover extension 130 is provided with hollow cover extension first open end 132, according to some embodiments. Through these open ends uncomplicated and efficient withdrawal and insertion of light sources 170 into or from transparent pipe 150 is enabled.

According to some embodiments, transparent pipe first open end 152 is offset upward from hollow cover extension first open end 132, which retains it. According to some embodiments, transparent pipe first open end 152 of each one of plurality of transparent pipes 150 is offset upward from hollow cover extension first open end 132, which retains it. According to some embodiments, transparent pipe first open end 152 is offset upward from hollow cover extension first open end 132, which is attached thereto. According to some embodiments, transparent pipe first open end 152 of each one of plurality of transparent pipes 150 is offset upward from hollow cover extension first open end 132, which is attached thereto.

According to some embodiments, hollow cover extension 130 comprises a hollow cover extension second end 134. According to some embodiments, each hollow cover extension 130 comprises a hollow cover extension second end 134. According to some embodiments, hollow cover extension second end $134^a$ is at the at the level of vessel cover 114. According to some embodiments, hollow cover extension second end $134^a$ is at the level of openings 120. According to some embodiments, hollow cover extension second end $134^b$ is offset downwards from vessel cover 114. According to some embodiments, hollow cover extension second end $134^b$ is located longitudinally between vessel cover 114 and vessel floor 112.

Specifically, FIG. 4A and FIG. 4B provide two alternative configurations of hollow cover extension second end 134—hollow cover extension second end $134^a$, which is located at the level of vessel cover 114, and refers to embodiments in which hollow cover extension 130 is extending upwards from vessel cover 114; and hollow cover extension second end $134^b$, which is located inside internal cavity 104 of vessel 110, and refers to embodiments in which hollow cover extension 130 is extending downwards towards internal cavity 104 from vessel cover 114 or through vessel cover 114.

According to some embodiments, one of hollow cover extension first open end 132 and hollow cover extension second end 134 is connected to vessel cover 114. According to some embodiments, one of hollow cover extension first open end 132 and hollow cover extension second end 134 is retained by one of openings 120 of vessel cover 114. According to some embodiments, one of hollow cover extension first open end 132 and hollow cover extension second end 134 is sealed to opening 120.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodiments, transparent pipe 150 is substantially sealed to opening 120, such that aqueous medium 102, when inserted to vessel 110, is substantially isolated from surrounding environment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100. According to some embodiments, each one of plurality of transparent pipes 150 is substantially sealed to one of openings 120. According to some embodiments, each one of plurality of transparent pipes 150 is substantially sealed to one of openings 120, such that internal cavity 104 of vessel 110 is substantially isolated from surrounding environment 106 of closed photobioreactor 100. According to some embodiments, each one of plurality of transparent pipes 150 is substantially sealed to one of openings 120, such that aqueous medium 102, when inserted to vessel 110, is substantially isolated from surrounding environment 106 of closed photobioreactor 100. According to some embodiments, each one of plurality of transparent pipes 150 is substantially sealed to one of openings 120, such that aqueous medium 102, within vessel 110, is substantially isolated from surrounding environment 106 of closed photobioreactor 100.

According to some embodiments, transparent pipe 150 is substantially sealed to hollow cover extension 130. According to some embodiments, transparent pipe 150 is substantially sealed to hollow cover extension 130, such that internal cavity 104 of vessel 110 is substantially isolated from surrounding environment 106 of closed photobioreactor 100. According to some embodiments, transparent pipe 150 is substantially sealed to hollow cover extension 130, such that aqueous medium 102, when inserted to vessel 110, is substantially isolated from surrounding environment 106 of closed photobioreactor 100. According to some embodiments, transparent pipe 150 is substantially sealed to hollow cover extension 130, such that aqueous medium 102, within vessel 110, is substantially isolated from surrounding environment 106 of closed photobioreactor 100. According to some embodiments, each one of plurality of transparent pipes 150 is substantially sealed to one of one of plurality of hollow cover extensions 130. According to some embodiments, each one of plurality of transparent pipes 150 is substantially sealed to one of plurality of hollow cover extensions 130, such that internal cavity 104 of vessel 110 is substantially isolated from surrounding environment 106 of closed photobioreactor 100. According to some embodiments, each one of plurality of transparent pipes 150 is substantially sealed to one of plurality of hollow cover extensions 130, such that aqueous medium 102, when inserted to vessel 110, is substantially isolated from surrounding environment 106 of closed photobioreactor 100. According to some embodiments, each one of plurality of transparent pipes 150 is substantially sealed to one of plurality of hollow cover extensions 130, such that aqueous medium 102, within vessel 110, is substantially isolated from surrounding environment 106 of closed photobioreactor 100.

According to some embodiments, hollow cover extension 130 comprises a hollow cover extension first portion 136. According to some embodiments, each hollow cover extension 130 comprises a hollow cover extension first portion 136. According to some embodiments, hollow cover extension first portion 136 is retaining transparent pipe 150. According to some embodiments, hollow cover extension first portion 136 is retaining one of plurality of transparent pipes 150. According to some embodiments, hollow cover extension first portion 136 is attached to transparent pipe 150. According to some embodiments, hollow cover extension first portion 136 is attached to one of plurality of transparent pipes 150. According to some embodiments, hollow cover extension first portion 136 is sealed to transparent pipe 150. According to some embodiments, hollow cover extension first portion 136 is sealed to one of plurality of transparent pipes 150.

According to some embodiments, hollow cover extension first portion 136 is retaining transparent pipe first portion $156^a$ of transparent pipe 150. According to some embodiments, hollow cover extension first portion 136 is retaining transparent pipe first portion $156^a$ of one of plurality of transparent pipes 150. According to some embodiments, hollow cover extension first portion 136 is attached to transparent pipe first portion $156^a$ of transparent pipe 150. According to some embodiments, hollow cover extension first portion 136 is attached to transparent pipe first portion $156^a$ of one of plurality of transparent pipes 150. According to some embodiments, hollow cover extension first portion 136 is sealed to transparent pipe first portion $156^a$ of transparent pipe 150. According to some embodiments, hollow cover extension first portion 136 is sealed to transparent pipe first portion $156^a$ of one of plurality of transparent pipes 150.

According to some embodiments, hollow cover extension first portion 136 is attached to opening 120. According to some embodiments, hollow cover extension first portion 136 is attached to one of plurality of openings 120. According to some embodiments, hollow cover extension first portion 136 is sealed to opening 120. According to some embodiments, hollow cover extension first portion 136 is sealed to one of plurality of opening 120.

According to some embodiments, hollow cover extension first portion 136 is attached to vessel cover 114. According to some embodiments, hollow cover extension first portion 136 is sealed to vessel cover 114.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, at least one of plurality of hollow cover extensions 130 is made of a rigid material. According to some embodiments, at least one of plurality of hollow cover extensions 130 is made of a polymer, a metal alloy or a metal. According to some embodiments, at least one of plurality of hollow cover extensions 130 is made of a metal alloy. According to some embodiments, at least one of plurality of hollow cover extensions 130 is made of a metal. According to some embodiments, at least one of plurality of hollow cover extensions 130 is made of stainless steel. According to some embodiments, hollow cover extension 130 is made of a rigid material. According to some embodiments, hollow cover extension 130 made of a polymer, a metal alloy or a metal. According to some embodiments, hollow cover extension 130 is made of a metal alloy. According to some embodiments, hollow cover extension 130 is made of a metal. According to some embodiments, hollow cover extension 130 is made of stainless steel. According to some embodiments, each one of plurality of hollow cover extensions 130 is made of a rigid material. According to some embodiments, each one of plurality of hollow cover extensions 130 is made of a polymer, a metal alloy or a metal. According to some embodiments, each one of plurality of hollow cover extensions 130 is made of a metal alloy. According to some embodiments, each one of plurality of hollow cover extensions 130 is made of a metal. According to some embodiments, each one of plurality of hollow cover extensions 130 is made of stainless steel.

It is to be understood that hollow cover extension first portion 136 is made of the same material of hollow cover extension 130, according to some embodiments. Specifically, according to some embodiments, hollow cover extension first portion 136 is made of a rigid material. According to some embodiments, hollow cover extension first portion 136 is made of a polymer, a metal alloy or a metal. According to some embodiments, hollow cover extension first portion 136 is made of a metal alloy. According to some embodiments, hollow cover extension first portion 136 is made of a metal. According to some embodiments, hollow cover extension first portion 136 is made of stainless steel.

According to some embodiments, hollow cover extension 130 is welded to vessel cover 114. According to some embodiments, each one of plurality of hollow cover extensions 130 is welded to vessel cover 114. According to some embodiments, hollow cover extension first portion 136 is welded to vessel cover 114. According to some embodiments, hollow cover extension first portion 136 of each one of plurality of hollow cover extensions 130 is welded to vessel cover 114.

According to some embodiments, hollow cover extension first portion 136 is located between hollow cover extension second end 134 and hollow cover extension first open end 132. According to some embodiments, hollow cover extension first portion 136 is located at hollow cover extension first open end 132. According to some embodiments, hollow cover extension first portion 136 is located in proximity to hollow cover extension first open end 132. According to some embodiments, hollow cover extension first portion 136 is located in proximity to hollow cover extension second end $134^a$.

According to some embodiments, hollow cover extension 130 comprises a hollow cover extension threaded external portion 138. According to some embodiments, each hollow cover extension 130 comprises hollow cover extension threaded external portion 138. According to some embodiments, hollow cover extension threaded external portion 138 is located at hollow cover extension first open end 132.

According to some embodiments, hollow cover extension threaded external portion 138 is located in proximity to hollow cover extension first open end 132. According to some embodiments, hollow cover extension threaded external portion 138 is offset upward from vessel cover 114.

According to some embodiments, closed photobioreactor 100 further comprises a plurality of double-open caps 180. According to some embodiments, plurality of double-open caps 180 is at an amount equal to the number of plurality of hollow cover extensions 130. According to some embodiments, plurality of double-open caps 180 is at an amount equal to the number of plurality of transparent pipes 150.

According to some embodiments, double-open cap 180 has two open ends. According to some embodiments, each one of double-open caps 180 has two open ends. According to some embodiments, double-open cap 180 is attachable to hollow cover extension first open end 132 of hollow cover extension 130. According to some embodiments, each one of plurality of double-open caps 180 is attachable to one of hollow cover extension first open end 132 of plurality of hollow cover extensions 130. According to some embodiments, double-open cap 180 is reversibly attachable to hollow cover extension first open end 132 of hollow cover extension 130. According to some embodiments, each one of plurality of double-open caps 180 is reversibly attachable to one of hollow cover extension first open end 132 of plurality of hollow cover extensions 130.

According to some embodiments, double-open cap 180 is configured to enhance to retention of hollow cover extension 130 to transparent pipe 150. According to some embodiments, double-open cap 180 is configured to enhance to the sealing of hollow cover extension 130 to transparent pipe 150, which retains it.

According to some embodiments, double-open cap 180 has a double-open cap threaded internal portion 184. According to some embodiments, each one of plurality of double-open caps 180 has a double-open cap threaded internal portion 184. According to some embodiments, double-open cap 180 has double-open cap threaded internal portion 184, wherein double-open cap 180 is screwable to hollow cover extension threaded external portion 138 through double-open cap threaded internal portion 184. According to some embodiments, each one of plurality of double-open caps 180 has double-open cap threaded internal portion 184, wherein each one of plurality of double-open caps 180 is screwable hollow cover extension threaded external portion 138 of one of plurality of hollow cover extensions 130 through its double-open cap threaded internal portion 184.

According to some embodiments, double-open cap threaded internal portion 184 is tubular. According to some embodiments, hollow cover extension threaded external portion 138 is tubular.

FIG. 4A and FIG. 4B depict different optional configurations of hollow cover extension 130. Specifically, it is apparent that three of four hollow cover extensions 130 of FIG. 4A and FIG. 4B depict hollow cover extension 130 capped with double-open cap 180, whereas one (the second from the right) of four hollow cover extensions 130 of FIG. 4A and FIG. 4B depict hollow cover extension 130 without double-open cap 180.

According to some embodiments, each one of transparent pipes 150 is substantially clear, such it is capable of transmitting light, such as visible light, to internal cavity 104 of vessel 110 when not disturbed by intervening objects. According to some embodiments, transparent pipe 150 is made of a transparent polymer or glass. According to some embodiments, transparent pipe 150 is made of glass.

According to some embodiments, each one of transparent pipes 150 pipes extends through one of openings 120.

FIGS. 4A and 4B depict a portion of vessel cover 114 connected through four hollow cover extensions 130 to four transparent pipes 150, however vessel cover 114 of closed photobioreactor 100 is not limited to this order of magnitude number of transparent pipes 150. Specifically, according to some embodiments, vessel cover 114 is retaining to at least two transparent pipes 150. Specifically, according to some embodiments, vessel cover 114 is retaining at least two transparent pipes 150. According to some embodiments, vessel cover 114 is retaining at least three transparent pipes 150. According to some embodiments, vessel cover 114 is retaining at least four transparent pipes 150. According to some embodiments, vessel cover 114 is retaining at least five transparent pipes 150. According to some embodiments, vessel cover 114 is retaining at least ten transparent pipes 150. According to some embodiments, vessel cover 114 is retaining at least 15 transparent pipes 150. According to some embodiments, vessel cover 114 is retaining at least 25 transparent pipes 150. According to some embodiments, vessel cover 114 is retaining at least 40 transparent pipes 150. According to some embodiments, vessel cover 114 is retaining at least 50 transparent pipes 150. According to some embodiments, vessel cover 114 is retaining at least 75 transparent pipes 150. According to some embodiments, vessel cover 114 is retaining at least 100 transparent pipes 150.

According to some embodiments, the number of transparent pipes 150 is equal to the number of openings 120 in vessel cover 114. According to some embodiments, a transparent pipe 150 extends through each one of openings 120 of vessel cover 114.

According to some embodiments, the number of transparent pipes 150 is equal to the number of hollow cover extensions 130 in vessel cover 114. According to some embodiments, a transparent pipe 150 extends through each one of hollow cover extension 130s of vessel cover 114.

FIGS. 4A and 4B show vessel cover 114 retaining a plurality of transparent pipes 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

It is to be understood that the shape of transparent pipe 150 is matching to the shape of hollow cover extension 130, according to some embodiments. It is to further be understood that the shape of transparent pipe 150 is matching to the shape of openings 120, according to some embodiments.

Specifically, FIGS. 4A and 4B show vessel cover 114 connected or welded to plurality of hollow cover extensions 130 having a cylindrical shape. However, closed photobioreactor 100 is not limited to circular shaped hollow cover extensions 130. According to some embodiments, each one of plurality of hollow cover extensions 130 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of plurality of hollow cover extensions 130 is cylindrical. According to some embodiments, each one of plurality of hollow cover extensions 130 is cylindrical.

According to some embodiments, each one of plurality of transparent pipes 150 has transparent pipe first open end 152 and transparent pipe second end 154. According to some embodiments, each one of plurality of transparent pipes 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 has a transparent pipe first open end 152 at the longitudinal top edge thereof. It is to be understood that by defining that transparent pipe first open end 152 is located out of internal cavity 104, it is not limited to a configuration in which transparent pipe first open end 152 is necessarily above vessel cover 114, according to some embodiments. Specifically, while transparent pipe first open end 152 may be offset upward from vessel cover 114, transparent pipe first open end 152 and vessel cover 114 may be substantially at the same level, such that transparent pipe first open end 152 is located out of internal cavity 104, according to some embodiments. Transparent pipe first open end 152 is located out of internal cavity 104 when transparent pipe first open end 152 is at the level of vessel cover 114, since vessel cover 114 defines the top boundary of internal cavity 104.

According to some embodiments, transparent pipe first open end 152 is flush with vessel cover 114 or is offset upward from vessel cover 114. According to some embodiments, transparent pipe first open end 152 is at the level of vessel cover 114. According to some embodiments, transparent pipe first open end 152 is offset upward from vessel cover 114. Specifically, FIG. 4A and FIG. 4B represent embodiments of closed photobioreactor 100 in which transparent pipe first open end 152 is offset upward from vessel cover 114. However, closed photobioreactor 100 is not limited to transparent pipe first open ends 152, of this configuration.

According to some embodiments, each one of plurality of transparent pipes 150 defines a transparent pipe lumen 160 there inside. According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, transparent pipe 150 has a transparent pipe second portion 158 located within internal cavity 104 of vessel 110. According to some embodiments, each one of plurality of transparent pipes 150 has a transparent pipe second portion 158 located within internal cavity 104 of vessel 110.

As detailed herein, according to some embodiments, transparent pipe 150 has a transparent pipe first open end

152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

According to some embodiments, transparent pipe lumen 160 is in fluid communication with surrounding environment 106 of closed photobioreactor 100, when not plugged. According to some embodiments, transparent pipe lumen 160 of each one of plurality of transparent pipes 150 is in fluid communication with surrounding environment 106 of closed photobioreactor 100, when not plugged. According to some embodiments, transparent pipe lumen 160 is in fluid communication with surrounding environment 106 of closed photobioreactor 100. According to some embodiments, transparent pipe lumen 160 of each one of plurality of transparent pipes 150 is in fluid communication with surrounding environment 106 of closed photobioreactor 100.

According to some embodiments, closed photobioreactor 100 further comprises a closed cap (not shown) configured to plug transparent pipe first open end 152. According to some embodiments, closed photobioreactor 100 further comprises a plurality of closed caps, each configured to plug transparent pipe first open end 152 of one of plurality of transparent pipes 150. Specifically, such closed caps are known in the art, and may include, but not limited to rubber plugs, plastic caps, glass caps, metal caps and wooden corks.

According to some embodiments, transparent pipe lumen 160 is isolated from internal cavity 104 of vessel 110. According to some embodiments, transparent pipe lumen 160 of each one of plurality of transparent pipes 150 is isolated from internal cavity 104 of vessel 110.

Figures 5A, 5B, 5C, 5D, 5E:
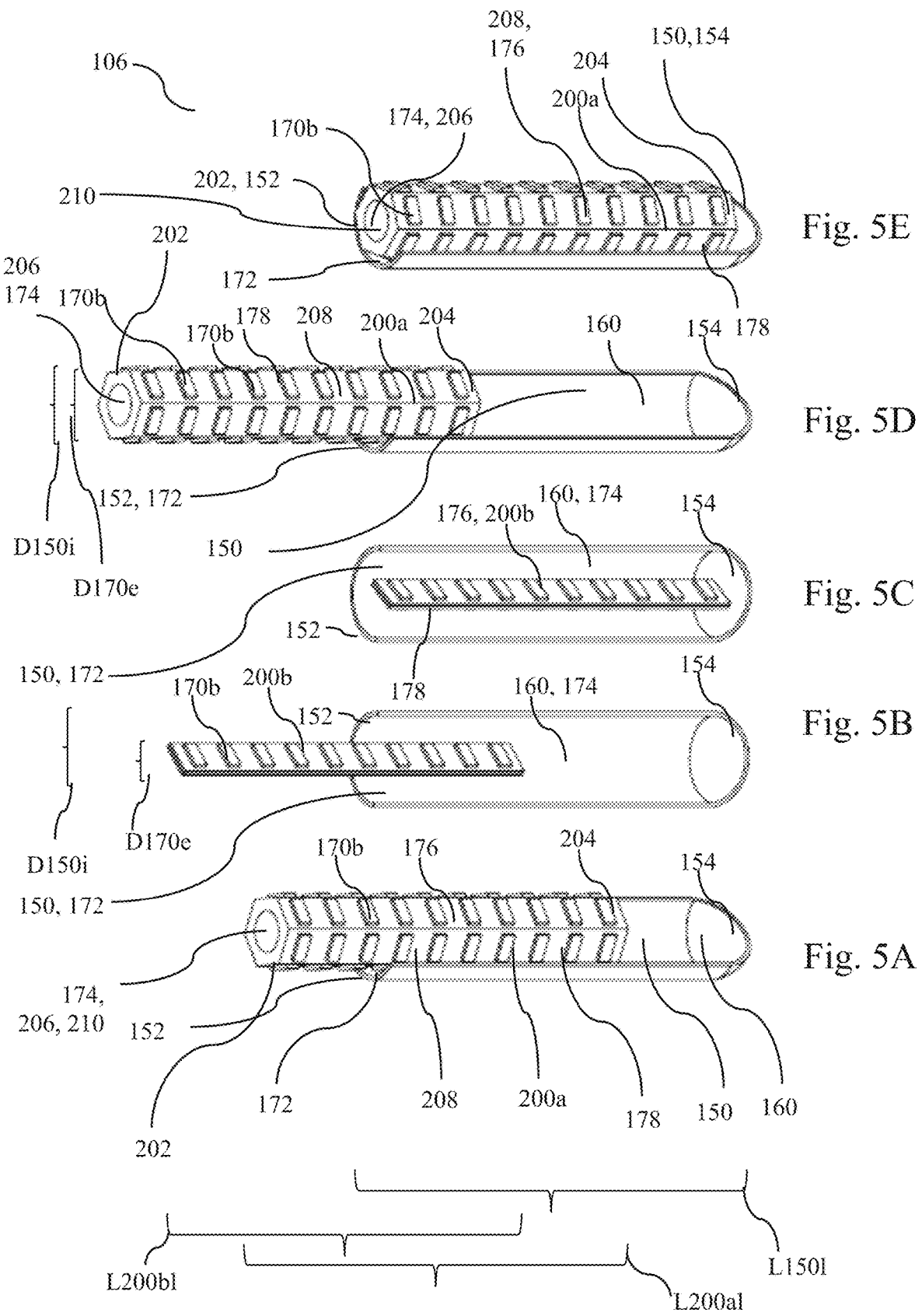
FIG. 5A constitutes a partial cross section view of a hollow illuminating LED pipe 200$^a$, partially inserted into transparent pipe 150, according to some embodiments.
FIG. 5B constitutes a partial cross section view of a LED strip 200$^b$, partially inserted into transparent pipe 150, according to some embodiments.
FIG. 5C constitutes a partial cross section view of a LED strip 200$^b$, inserted into transparent pipe 150, according to some embodiments.
FIG. 5D constitutes a partial cross section view of a hollow illuminating LED pipe 200$^a$, partially inserted into transparent pipe 150, according to some embodiments.
FIG. 5E constitutes a partial cross section view of a hollow illuminating LED pipe 200$^a$, inserted into transparent pipe 150, according to some embodiments.

Reference is made to FIGS. 5A-5E. FIG. 5A constitutes a partial cross section view of a hollow illuminating LED pipe 200$^a$, partially inserted into transparent pipe 150. FIG. 5B constitutes a partial cross section view of a LED strip 200$^b$, partially inserted into transparent pipe 150. FIG. 5C constitutes a partial cross section view of a LED strip 200$^b$, inserted into transparent pipe 150. FIG. 5D constitutes a partial cross section view of a hollow illuminating LED pipe 200$^a$, partially inserted into transparent pipe 150. FIG. 5E constitutes a partial cross section view of a hollow illuminating LED pipe 200$^a$, inserted into transparent pipe 150.

Any one or more of transparent pipes 150 as shown in FIG. 5A-E may be used as transparent pipe 150 of closed photobioreactor 100 of FIGS. 1A-B and/or as transparent pipe 150 of closed photobioreactor 100 of FIGS. 3A-B. Any one or more of transparent pipes 150 as shown in FIG. 5A-E may be used as transparent pipe 150 of FIGS. 4A-B.

According to some embodiments, as seen in FIGS. 5A-E each one of hollow illuminating LED pipe 200$^a$ and LED strip 200$^b$ includes a plurality of LED lamps 170$^b$. According to some embodiments, plurality of LED lamps 170$^b$ of each one of hollow illuminating LED pipe 200$^a$ and LED strip 200$^b$ may be used as light source(s) 170 of closed photobioreactor 100 of FIGS. 1A-B and/or as light source(s) 170 of closed photobioreactor 100 of FIGS. 3A-B.

Specifically, the embodiments depicted in FIGS. 5A-E relate to several optional configurations of an illumination apparatus (hollow illuminating LED pipe $200^a$ or LED strip $200^b$), which comprises light source 170, wherein light source 170 is introduced when referring to closed photo-bioreactor 100 of FIGS. 1A-B and closed photobioreactor 100 of FIGS. 3A-B.

According to some embodiments, each one of transparent pipes 150 is substantially clear, such it is capable of trans-mitting light, such as visible light, to internal cavity 104 of vessel 110 when not disturbed by intervening objects.

According to some embodiments, transparent pipe 150 is made of a transparent polymer or glass. Transparent poly-mers (plastics) include, but not limited to, Poly(methyl methacrylate), polycarbonates, ethylene-vinyl acetate poly-mer, polystyrene sulfonate, polystyrene, polypropylene and polyethylene. According to some embodiments, transparent pipe 150 is made of glass.

According to some embodiments, each one of transparent pipes 150 pipes extends through one of openings 120 of vessel cover 114 of closed photobioreactor 100.

FIGS. 5A-E illustrate 5 transparent pipes 150 having a cylindrical shape. However, closed photobioreactor 100 is not limited to circular shaped transparent pipe 150. Specifi-cally, according to some embodiments, each one of trans-parent pipes 150 may have any curvilinear shape or recti-linear shape, such as a circle, an ellipsoid, a square, a rectangle, a hexagon, an octagon, including three dimen-sional shapes thereof, such as cuboid and cylinder. Accord-ing to some embodiments, at least one of transparent pipes 150 is cylindrical. According to some embodiments, each one of transparent pipes 150 is cylindrical.

According to some embodiments, each one of transparent pipes 150 is connected to vessel cover 114. According to some embodiments, each one of transparent pipes 150 is attached to vessel cover 114. According to some embodi-ments, each one of transparent pipes 150 is connected to one of openings 120.

According to some embodiments, each one of plurality of transparent pipes 150 has a transparent pipe first open end 152 and a transparent pipe second end 154. According to some embodiments, each one of plurality of transparent pipes 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 has a transparent pipe first open end 152 at the longitudinal top edge thereof.

According to some embodiments, transparent pipe first open end 152 is flush with vessel cover 114 or is offset upward from vessel cover 114. According to some embodi-ments, transparent pipe first open end 152 is at the level of vessel cover 114. According to some embodiments, trans-parent pipe first open end 152 is offset upward from vessel cover 114.

According to some embodiments, each one of plurality of transparent pipes 150 defines a transparent pipe lumen 160 there inside.

According to some embodiments, transparent pipe 150 is connected to at least one of vessel cover 114 and vessel floor 112.

According to some embodiments, transparent pipe 150 has a transparent pipe first portion 156 connected, directly or indirectly, to at least one of vessel cover 114 and vessel floor 112. According to some embodiments, transparent pipe first portion 156 is connected to one of vessel cover 114 and vessel floor 112. According to some embodiments, transpar-ent pipe first portion $156^a$ is connected to vessel cover 114.

According to some embodiments, transparent pipe 150 has a transparent pipe second portion 158 located within internal cavity 104 of vessel 110.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodi-ments, transparent pipe 150 is substantially sealed to open-ing 120, such that aqueous medium 102, when inserted to vessel 110, is substantially isolated from surrounding envi-ronment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100. According to some embodiments, each one of plurality of transparent pipes 150 is substantially sealed to one of openings 120. According to some embodiments, each one of plurality of transparent pipes 150 is substantially sealed to one of openings 120, such that internal cavity 104 of vessel 110 is substantially isolated from surrounding environment 106 of closed photobioreactor 100. According to some embodi-ments, each one of plurality of transparent pipes 150 is substantially sealed to one of openings 120, such that aqueous medium 102, when inserted to vessel 110, is substantially isolated from surrounding environment 106 of closed photobioreactor 100. According to some embodi-ments, each one of plurality of transparent pipes 150 is substantially sealed to one of openings 120, such that aqueous medium 102, within vessel 110, is substantially isolated from surrounding environment 106 of closed pho-tobioreactor 100.

As detailed herein, transparent pipe lumens 160 are exposable to surrounding environment 106 of closed pho-tobioreactor 100, according to some embodiments. Specifi-cally, each one of plurality of transparent pipes 150 has a transparent pipe first open end 152, said open end enables exposure of the respective transparent pipe lumen 160 to surrounding environment 106 when uncapped, according to some embodiments.

As can be seen in FIGS. 5A-E, transparent pipe lumen 160 is exposed to surrounding environment 106 through trans-parent pipe first open end 152, according to some embodi-ments. It is an improvement of the currently presented closed photobioreactors 100 compared to known closed photobioreactors that uncomplicated insertion and with-drawal of light source 170, and assemblies comprising the same (e.g. hollow illuminating LED pipe $200^a$ or LED strip $200^b$) into or from transparent pipe 150 is possible. Specifi-cally, as can be seen in FIGS. 5A-E any one of hollow illuminating LED pipe $200^a$ or LED strip $200^b$ is easily withdrawable from transparent pipe 150. It is noted that operation and maintenance of closed photobioreactors typi-cally include (a) growing a microorganism culture which requires illumination (e.g. algae) inside the closed photobioreactor, with exposure to light (b) removing the microorganism culture from the closed photobioreactor; and (c) cleaning and sterilization of the closed photobioreactor interior. Typically, step (c) requires employment of high temperatures, whereas step (a) requires illumination. Illumination of step (a) is achieved by using a light source (such as LED lamps) located inside the closed photobioreactor. Such light sources are sensitive to high temperatures and may malfunction upon exposure to the heating conditions of step (c). The current closed photobioreactor 100 is a photobioreactor, which provides easy access and uncomplicated withdrawal of the light source from its interior. Thus, it is an improvement provided by the current disclosure that a transparent pipe 150 has a transparent pipe first open end 152, which is open and allows insertion or withdrawal of light source 170 from transparent pipe lumen 160 thereof.

According to some embodiments, transparent pipe 150 has a transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. The importance of this type of fluid communication is elaborated herein.

As detailed herein, it is an intention of the present disclosure to provide a closed photobioreactor 100, which (a) has an internal cavity 104 substantially separated from surrounding environment 106 of closed photobioreactor 100; (b) is capable of providing sufficient illumination to aqueous medium 102 inside vessel 110; and (c) enables uncomplicated and efficient withdrawal and insertion of light sources 170, such as LED lamp 170$^b$ of any one of hollow illuminating LED pipe 200$^a$ or LED strip 200$^b$, according to some embodiments. In order to fulfill requirement (c), transparent pipe 150 is provided with transparent pipe first open end 152, and hollow cover extension 130 is provided with hollow cover extension first open end 132, according to some embodiments. Through these open ends uncomplicated and efficient withdrawal and insertion of light sources 170 into or from transparent pipe 150 is enabled.

According to some embodiments, transparent pipe lumen 160 is in fluid communication with surrounding environment 106 of closed photobioreactor 100, when not plugged.

According to some embodiments, closed photobioreactor 100 further comprises a closed cap (not shown) configured to plug transparent pipe first open end 152.

It is to be understood that since transparent pipe lumen 160 may come in contact with surrounding environment 106, and since aqueous medium 102 and internal cavity 104 are to be separated from surrounding environment 106, transparent pipe lumen 160 should also be separated from aqueous medium 102 and internal cavity 104 of vessel 110.

According to some embodiments, transparent pipe 150 has a longitudinal length L150$l$. FIGS. 5A-E show five transparent pipes 150 having the same longitudinal length L150$l$, however it is to be understood that closed photobioreactor 100 may include plurality of transparent pipes

150 having varied longitudinal lengths. Longitudinal length of transparent pipe L150$l$ of transparent pipe 150 of FIG. 5A is shown in curly brackets.

According to some embodiments, hollow illuminating LED pipe 200$^a$ has a longitudinal length L200$^a$1. FIGS. 5A, 5D and 5E show three hollow illuminating LED pipe 200$^a$ having the same longitudinal length L200$^a$1, however it is to be understood that closed photobioreactor 100 may include plurality of hollow illuminating LED pipes 200$^a$ having varied longitudinal lengths. Longitudinal length of hollow illuminating LED pipe L200$^a$1 of hollow illuminating LED pipe 200$^a$ of FIG. 5A is shown in curly brackets.

According to some embodiments, LED strip 200$^b$ has a longitudinal length L200$^b$1. FIGS. 5B and 5C show two LED strip 200$^b$ having the same longitudinal length L200$^b$1, however it is to be understood that closed photobioreactor 100 may include plurality of LED strips 200$^b$ having varied longitudinal lengths. Longitudinal length of LED strip L200$^b$1 of LED strip 200$^b$ of FIG. 5B is shown in curly brackets.

According to some embodiments, longitudinal length of transparent pipe L150$l$ is equal or longer than longitudinal length of hollow illuminating LED pipe L200$^a$1. According to some embodiments, longitudinal length of transparent pipe L150$l$ is longer than longitudinal length of hollow illuminating LED pipe L200$^a$1.

According to some embodiments, longitudinal length of hollow illuminating LED pipe L200$^a$1 is in the range of 10% to 100% compared to longitudinal length of transparent pipe L150$l$. According to some embodiments, longitudinal length of hollow illuminating LED pipe L200$^a$1 is in the range of 20% to 98% compared to longitudinal length of transparent pipe L150$l$. According to some embodiments, longitudinal length of hollow illuminating LED pipe L200$^a$1 is in the range of 25% to 97% compared to longitudinal length of transparent pipe L150$l$. According to some embodiments, longitudinal length of hollow illuminating LED pipe L200$^a$1 is in the range of 30% to 95% compared to longitudinal length of transparent pipe L150$l$.

According to some embodiments, longitudinal length of transparent pipe L150$l$ is equal or longer than longitudinal length of LED strip L200$^b$1. According to some embodiments, longitudinal length of transparent pipe L150$l$ is longer than longitudinal length of LED strip L200$^b$$l$.

According to some embodiments, longitudinal length longitudinal length of LED strip L200$^b$1 is in the range of 10% to 100% compared to longitudinal length of transparent pipe L150$l$. According to some embodiments, longitudinal length of LED strip L200$^b$1 is in the range of 20% to 98% compared to longitudinal length of transparent pipe L150$l$. According to some embodiments, longitudinal length of LED strip L200$^b$1 is in the range of 25% to 97% compared to longitudinal length of transparent pipe L150$l$. According to some embodiments longitudinal length of LED strip L200$^b$1 is in the range of 30% to 95% compared to longitudinal length of transparent pipe L150$l$.

According to some embodiments, transparent pipe 150 has an internal diameter D150$i$. FIGS. 5A-E show five transparent pipes 150 having the same internal diameter D150$i$, however it is to be understood that closed photobioreactor 100 may include plurality of transparent pipes 150 having varied internal diameters. Transparent pipe internal diameter D150$i$ of transparent pipe 150 of FIG. 5D is shown in curly brackets.

According to some embodiments, hollow illuminating LED pipe 200$^a$ has an external diameter D200$^a$e. FIGS. 5A, 5D and 5E show three hollow illuminating LED pipe 200$^a$ having the same external diameter D200$^a$e, however it is to be understood that closed photobioreactor 100 may include plurality of hollow illuminating LED pipes 200$^a$ having varied external diameters. External diameter of hollow illuminating LED pipe D200$^a$e of hollow illuminating LED pipe 200$^a$ of FIG. 5D is shown in curly brackets.

According to some embodiments, LED strip 200$^b$ has an external diameter D200$^b$e. FIGS. 5B and 5C show two LED strips 200$^b$ having the same external diameter D200$^b$e, however it is to be understood that closed photobioreactor 100 may include plurality of LED strips 200$^b$ having varied external diameters. External diameter of LED strip D200$^b$e of LED strip 200$^b$ of FIG. 5C is shown in curly brackets.

According to some embodiments, transparent pipe internal diameter D150$i$ is equal or larger than external diameter of hollow illuminating LED pipe D200$^a$e. According to some embodiments, transparent pipe internal diameter D150$i$ is larger than external diameter of hollow illuminating LED pipe D200$^a$e.

According to some embodiments, external diameter of hollow illuminating LED pipe D200$^a$e is in the range of 10% to 99% compared to transparent pipe internal diameter D150$i$. According to some embodiments, external diameter of hollow illuminating LED pipe D200$^a$e is in the range of 20% to 97% compared to transparent pipe internal diameter D150$i$. According to some embodiments, external diameter of hollow illuminating LED pipe D200$^a$e is in the range of 30% to 95% compared to transparent pipe internal diameter D150$i$. According to some embodiments, external diameter of hollow illuminating LED pipe D200$^a$e is in the range of 50% to 90% compared to transparent pipe internal diameter D150$i$.

According to some embodiments, transparent pipe internal diameter D150$i$ is equal or larger than external diameter of LED strip D200$^b$e. According to some embodiments, transparent pipe internal diameter D150$i$ is larger than external diameter of LED strip D200$^b$e.

According to some embodiments, external diameter of LED strip D200$^b$e is in the range of 10% to 99% compared to transparent pipe internal diameter D150$i$. According to some embodiments, external diameter of LED strip D200$^b$e is in the range of 20% to 97% compared to transparent pipe internal diameter D150$i$. According to some embodiments, external diameter of LED strip D200$^b$e is in the range of 30% to 95% compared to transparent pipe internal diameter D150$i$. According to some embodiments, e external diameter of LED strip D200$^b$e is in the range of 50% to 90% compared to transparent pipe internal diameter D150$i$.

According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, light source 170 is a LED lamp 170$^b$.

According to some embodiments, plurality of transparent pipes 150 are configured to accommodate a plurality of LED lamps 170$^b$ within transparent pipe lumens 160 thereof. According to some embodiments, each one of plurality of transparent pipes 150 is configured to accommodate at least one LED lamp 170$^b$ within transparent pipe lumen 160 thereof. According to some embodiments, each one of plurality of transparent pipes 150 is configured to accommodate a plurality of LED lamps 170$^b$ within transparent pipe lumen 160 thereof.

According to some embodiments, transparent pipe 150 is accommodating a light source 170 within transparent pipe lumen 160 thereof. According to some embodiments, transparent pipe 150 is accommodating LED lamp 170$^b$ within transparent pipe lumen 160 thereof. According to some embodiments, plurality of transparent pipes 150 are accommodating plurality of light sources 170 within transparent pipe lumens 160 thereof. According to some embodiments, plurality of transparent pipes 150 are accommodating plurality of LED lamps 170$^b$ within transparent pipe lumens 160 thereof.

According to some embodiments, each of plurality of light sources 170 is drawable from transparent pipe 150, which accommodates it. According to some embodiments, each of a plurality of LED lamps 170$^b$ is drawable from transparent pipe 150, which accommodates it.

According to some embodiments, upon the accommodation, a positive gap 172 between transparent pipe internal diameter D150$i$ and external diameter of hollow illuminating LED pipe D200$^a$e exists. According to some embodiments, upon the accommodation, a positive gap 172 between transparent pipe internal diameter D150$i$ and external diameter of LED strip D200$^b$e exists.

According to some embodiments, upon the accommodation, a positive gap 172 between transparent pipe internal diameter D150$i$ and the external dimensions of light source 170 exists. According to some embodiments, upon the accommodation, a positive gap 172 between transparent pipe internal diameter D150$i$ and the external dimensions of LED lamp 170$^b$ exists.

According to some embodiments, transparent pipe 150 is accommodating hollow illuminating LED pipe 200$^a$ within transparent pipe lumen 160 thereof. According to some embodiments, transparent pipe 150 is accommodating hollow illuminating LED pipe 200$^a$ within transparent pipe lumen 160 thereof. According to some embodiments, plurality of transparent pipes 150 are accommodating plurality of hollow illuminating LED pipes 200$^a$ within transparent pipe lumens 160 thereof. According to some embodiments, plurality of transparent pipes 150 are accommodating plurality of hollow illuminating LED pipes 200$^a$ within transparent pipe lumens 160 thereof.

According to some embodiments, transparent pipe 150 is accommodating LED strip 200$^b$ within transparent pipe lumen 160 thereof. According to some embodiments, transparent pipe 150 is accommodating LED strip 200$^b$ within transparent pipe lumen 160 thereof. According to some embodiments, plurality of transparent pipes 150 are accommodating plurality of LED strips 200$^b$ within transparent pipe lumens 160 thereof. According LED strips 200$^b$ within transparent pipe lumens 160 thereof.

According to some embodiments, LED lamp 170$^b$ has two flat planes. According to some embodiments, LED lamp 170$^b$ has a LED lamp illuminating plane 176 and a LED lamp heat emitting plane 178. According to some embodiments, each one of a plurality of LED lamps 170$^b$ has a LED lamp illuminating plane 176 and a LED lamp heat emitting plane 178.

According to some embodiments, LED lamp 170$^b$ is configured to emit light at wavelengths in the range of 400-700 nm.

Specifically, it is to be understood that LED lamps, such as LED lamp 170$^b$, create illumination and generate residual heat during the illumination process. Conventional that LED lamps, such as LED lamp $170^b$, are constructed such that one of the planes thereof is illuminating and the other is emitting the heat.

According to some embodiments, LED strip $200^b$ is a substantially two dimensional strip having two flat surfaces. According to some embodiments, at least one of the flat surfaces of LED strip $200^b$ comprises a plurality of LED lamps $170^b$. According to some embodiments, one of the flat surfaces of LED strip $200^b$ comprises a plurality of LED lamps $170^b$. According to some embodiments, LED strip $200^b$ is configured to emit light at wavelengths in the range of 400-700 nm.

According to some embodiments, one of the flat surfaces of LED strip $200^b$ comprises a plurality of LED lamps $170^b$, wherein LED lamp illuminating plane 176 of each of plurality of LED lamps $170^b$ is facing transparent pipe 150, when LED lamp $170^b$ is inserted into transparent pipe lumen 160. According to some embodiments, each of the flat surfaces of LED strip $200^b$ comprises a plurality of LED lamps $170^b$, wherein LED lamp illuminating plane 176 of each of plurality of LED lamps $170^b$ is facing transparent pipe 150, when LED lamp $170^b$ is inserted into transparent pipe lumen 160.

According to some embodiments, one of the flat surfaces of LED strip $200^b$ comprises a plurality of LED lamps $170^b$, wherein LED lamp illuminating plane 176 of each of plurality of LED lamps $170^b$ is facing outward. According to some embodiments, each of the flat surfaces of LED strip $200^b$ comprises a plurality of LED lamps $170^b$, wherein LED lamp illuminating plane 176 of each of plurality of LED lamps $170^b$ is facing outward.

According to some embodiments, LED strip $200^b$ comprises a plurality of LED lamps $170^b$, wherein LED lamp illuminating plane 176 is facing transparent pipe 150 from one of the two flat surfaces of LED lamp $170^b$, and wherein LED lamp heat emitting plane 178 is facing transparent pipe 150 from the other of the two flat surfaces of LED lamp $170^b$.

According to some embodiments, hollow illuminating LED pipe $200^a$ is a three dimensional structure. According to some embodiments, each one of plurality of hollow illuminating LED pipes $200^a$ is a three dimensional structure. Hollow illuminating LED pipe $200^a$ as depicted in FIGS. 5A, 5B and 5E has an external hexagonal prism shape and an internal cylindrical shape. However, the internal and external shapes of hollow illuminating LED pipe $200^a$ are not limited to hexagonal prism and cylinder. According to some embodiments, each one of hollow illuminating LED pipe $200^a$ may have any curvilinear shape or rectilinear shape, such as a circle, an ellipsoid, a square, a rectangle, a hexagon, an octagon, including three dimensional shapes thereof, such as prisms, cuboids and cylinder.

According to some embodiments, hollow illuminating LED pipe $200^a$ has a hollow illuminating LED pipe external surface 208 and a hollow illuminating LED pipe internal surface 206. According to some embodiments, each one of plurality of hollow illuminating LED pipes $200^a$ has a hollow illuminating LED pipe external surface 208 and a hollow illuminating LED pipe internal surface 206.

According to some embodiments, hollow illuminating LED pipe external surface 208 has a shape selected from the group consisting of circular, triangular, square, pentagonal, hexagonal, heptagonal and octagonal.

According to some embodiments, hollow illuminating LED pipe external surface 208 has a shape selected from the group consisting of circular, triangular, square, pentagonal, hexagonal, heptagonal and octagonal.

According to some embodiments, hollow illuminating LED pipe internal surface 206 is defining a hollow illuminating LED pipe internal lumen 210. According to some embodiments, hollow illuminating LED pipe internal surface 206 of each one of plurality of hollow illuminating LED pipes $200^a$ is defining a hollow illuminating LED pipe internal lumen 210.

According to some embodiments, hollow illuminating LED pipe internal surface 206 has a shape selected from the group consisting of circular, triangular, square, pentagonal, hexagonal, heptagonal and octagonal. According to some embodiments, hollow illuminating LED pipe internal lumen 210 has the shape of hollow illuminating LED pipe internal surface 206.

According to some embodiments, hollow illuminating LED pipe $200^a$ has a hollow illuminating LED pipe first open end 202 and a hollow illuminating LED pipe second end 204. According to some embodiments, each one of plurality of hollow illuminating LED pipes $200^a$ has a hollow illuminating LED pipe first open end 202 and a hollow illuminating LED pipe second end 204.

As detailed below, hollow illuminating LED pipe first open end 202 acts as an opening, which enables insertion of a light source cooling liquid 174 into hollow illuminating LED pipe internal lumen 210, according to some embodiments. For this end, hollow illuminating LED pipe first open end 202 is required to be open, according to some embodiments. Hollow illuminating LED pipe second end 204, on the other hand may be open or closed, according to some embodiments, as the insertion of light source cooling liquid 174 into hollow illuminating LED pipe internal lumen 210 may be performed through one or two openings.

According to some embodiments, hollow illuminating LED pipe $200^a$ comprises plurality of LED lamps $170^b$. According to some embodiments, hollow illuminating LED pipe $200^a$ is attached to plurality of LED lamps $170^b$. According to some embodiments, each one of plurality of hollow illuminating LED pipes $200^a$ comprises a plurality of LED lamps $170^b$. According to some embodiments each one of plurality of hollow illuminating LED pipes $200^a$ is attached to a plurality of LED lamps $170^b$.

According to some embodiments, LED lamp illuminating plane 176 of each of LED lamps $170^b$ of hollow illuminating LED pipe $200^a$ is located on hollow illuminating LED pipe external surface 208. According to some embodiments, LED lamp illuminating plane 176 of each of LED lamps $170^b$ of hollow illuminating LED pipe $200^a$ is facing transparent pipe 150, when hollow illuminating LED pipe $200^a$ is inserted into transparent pipe lumen 160. According to some embodiments, LED lamp illuminating plane 176 of each of LED lamps $170^b$ of each one of plurality of hollow illuminating LED pipes $200^a$ is located on hollow illuminating LED pipe external surface 208. According to some embodiments, LED lamp illuminating plane 176 of each of LED lamps $170^b$ of each one of plurality of hollow illuminating LED pipes $200^a$ is facing transparent pipe 150, when hollow illuminating LED pipes $200^a$ are inserted into transparent pipe lumens 160.

According to some embodiments, LED lamp heat emitting plane 178 of each of LED lamps $170^b$ of hollow illuminating LED pipe $200^a$ is located on hollow illuminating LED pipe internal surface 206. According to some embodiments, LED lamp heat emitting plane 178 of each of LED lamps $170^b$ of hollow illuminating LED pipe $200^a$ is facing hollow illuminating LED pipe internal lumen 210, when hollow illuminating LED pipe $200^a$ is inserted into transparent pipe lumen 160. According to some embodiments, LED lamp heat emitting plane 178 of each of LED lamps 170$^b$ of each one of plurality of hollow illuminating LED pipes 200$^a$ is located on hollow illuminating LED pipe internal surface 206. According to some embodiments, LED lamp heat emitting plane 178 of each of LED lamps 170$^b$ of each one of plurality of hollow illuminating LED pipes 200$^a$ is facing hollow illuminating LED pipe internal lumen 210, when hollow illuminating LED pipes 200$^a$ are inserted into transparent pipe lumens 160.

According to some embodiments, hollow illuminating LED pipe 200$^a$ comprises a plurality of LED lamps 170$^b$, wherein LED lamp illuminating plane 176 of each of plurality of LED lamps 170$^b$ is facing outward. According to some embodiments, hollow illuminating LED pipe 200$^a$ comprises a plurality of LED lamps 170$^b$, wherein LED lamp heat emitting plane 178 of each of plurality of LED lamp heat emitting plane 178 is facing inward.

The term "outward" as used with respect to hollow illuminating LED pipe 200$^a$ refers to the centrifugal direction out of hollow illuminating LED pipe 200$^a$. The term "in" as used with respect to hollow illuminating LED pipe 200$^a$ refers to the direction opposite to the outward direction—the centripetal direction toward hollow illuminating LED pipe internal lumen 210.

According to some embodiments, transparent pipe 150 contains a light source cooling liquid 174. According to some embodiments, each one of plurality of transparent pipes 150 contains a light source cooling liquid 174. According to some embodiments, light source cooling liquid 174 comprises water.

According to some embodiments, transparent pipe 150 contains a light source cooling liquid 174. According to some embodiments, transparent pipe 150 contains a light source cooling liquid 174 within transparent pipe lumen 160 thereof. According to some embodiments, each one of plurality of transparent pipes 150 contains a light source cooling liquid 174. According to some embodiments, each one of plurality of transparent pipes 150 contains a light source cooling liquid 174 within transparent pipe lumen 160 thereof.

According to some embodiments, light source cooling liquid 174 is in contact with light source 170. According to some embodiments, light source cooling liquid 174 is in contact with light source 170 within transparent pipe lumen 160. According to some embodiments, light source cooling liquid 174 is in contact with light source 170 within transparent pipe lumen 160 of each one of plurality of transparent pipes 150.

According to some embodiments, light source cooling liquid 174 is in contact with LED lamp 170$^b$. According to some embodiments, light source cooling liquid 174 is in contact with LED lamp 170$^b$ within transparent pipe lumen 160. According to some embodiments, light source cooling liquid 174 is in contact with LED lamp 170$^b$ within transparent pipe lumen 160 of each one of plurality of transparent pipes 150.

According to some embodiments, light source cooling liquid 174 is in contact with hollow illuminating LED pipe 200$^a$. According to some embodiments, light source cooling liquid 174 is in contact with hollow illuminating LED pipe 200$^a$ within transparent pipe lumen 160. According to some embodiments, light source cooling liquid 174 is in contact with hollow illuminating LED pipe 200$^a$ within transparent pipe lumen 160 of each one of plurality of transparent pipes 150.

According to some embodiments, light source cooling liquid 174 is in contact with LED strip 200$^b$. According to some embodiments, light source cooling liquid 174 is in contact with LED strip 200$^b$ within transparent pipe lumen 160. According to some embodiments, light source cooling liquid 174 is in contact with LED strip 200$^b$ within transparent pipe lumen 160 of each one of plurality of transparent pipes 150.

According to some embodiments, light source cooling liquid 174 is in contact with LED lamp illuminating plane 176. According to some embodiments, light source cooling liquid 174 is in contact with LED lamp illuminating plane 176 within transparent pipe lumen 160. According to some embodiments, light source cooling liquid 174 is in contact with LED lamp illuminating plane 176 within transparent pipe lumen 160 of each one of plurality of transparent pipes 150.

According to some embodiments, light source cooling liquid 174 is in contact with LED lamp heat emitting plane 178. According to some embodiments, light source cooling liquid 174 is in contact with LED lamp heat emitting plane 178 within transparent pipe lumen 160. According to some embodiments, light source cooling liquid 174 is in contact with LED lamp heat emitting plane 178 within transparent pipe lumen 160 of each one of plurality of transparent pipes 150.

Specifically, it is preferable that light source cooling liquid 174 comes in contact with at least LED lamp heat emitting plane 178, when both are inserted into transparent pipe 150 (typically during operation) thereby cooling LED lamp 170$^b$ to maintain its proper performance and durability.

Without wishing to be bound by any theory or mechanism of action, the temperature of aqueous medium 102 in internal cavity 104 of closed photobioreactor 100 is lower than the temperature inside transparent pipe lumen 160, since transparent pipe lumen 160 is receiving the emitted heat of light sources 170, according to some embodiments. Light source cooling liquid 174, when inside transparent pipe lumen 160 acts as a medium for the transferring of the heat, thereby cooling light sources 170 within plurality of transparent pipes 150. This mechanism enables maintaining proper temperature of plurality of light sources 170, while not using active cooling. According to some embodiments, closed photobioreactor 100 is devoid of an active cooling device configured to reduce the temperature inside transparent pipe 150. According to some embodiments, closed photobioreactor 100 is devoid of an active cooling device configured to reduce the temperature of plurality of light sources 170.

When hollow illuminating LED pipe 200$^a$ is used, light source cooling liquid 174 may flow into hollow illuminating LED pipe internal lumen 210 thereof through hollow illuminating LED pipe first open end 202. In this sense, hollow illuminating LED pipe first open end 202 acts as an opening, which enables insertion of light source cooling liquid 174 into hollow illuminating LED pipe internal lumen 210, according to some embodiments. As detailed above hollow illuminating LED pipe second end 204 may also be open, such that light source cooling liquid 174 may flow into hollow illuminating LED pipe internal lumen 210 through both hollow illuminating LED pipe first open end 202 and hollow illuminating LED pipe second end 204, according to some embodiments. It is to be understood that the insertion of light source cooling liquid 174 into hollow illuminating LED pipe internal lumen 210 leads to contact between light source cooling liquid 174 and hollow illuminating LED pipe internal surface 206 and thus to contact between light source cooling liquid 174 and LED lamp heat emitting planes 178 of LED lamps $170^b$ mounted to hollow illuminating LED pipe $200^a$, according to some embodiments.

According to some embodiments, at least part of light source cooling liquid 174 is contained within hollow illuminating LED pipe internal lumen 210. According to some embodiments, at least part of light source cooling liquid 174 is contained within hollow illuminating LED pipe internal lumen 210, such that light source cooling liquid 174 is in contact with hollow illuminating LED pipe internal surface 206. According to some embodiments, at least part of light source cooling liquid 174 is contained within hollow illuminating LED pipe internal lumen 210, wherein hollow illuminating LED pipe internal surface 206 is in contact with LED lamp heat emitting plane 178, such that light source cooling liquid 174 is in contact with LED lamp heat emitting plane 178.

Figure 6:
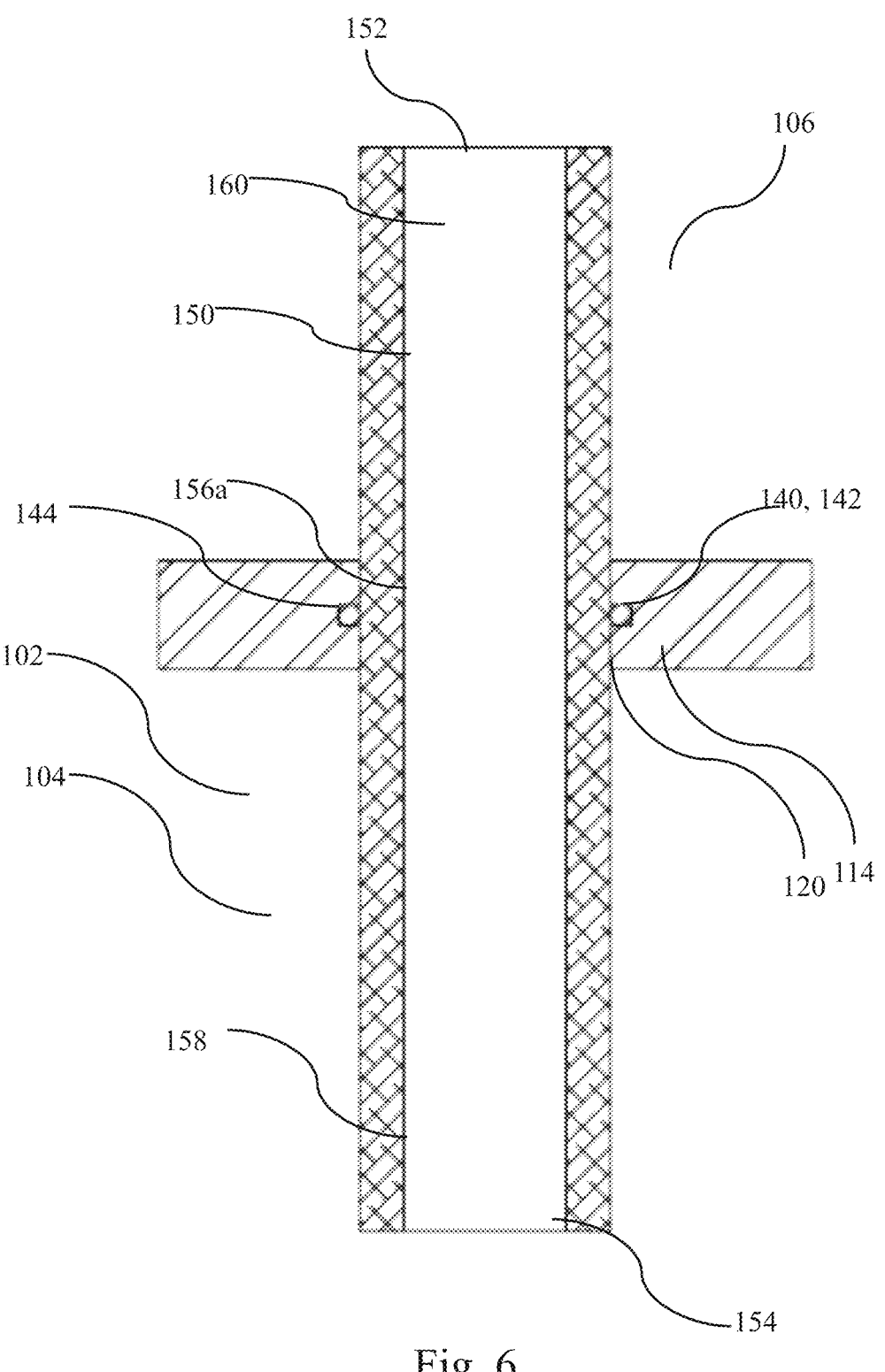
FIG. 6 constitutes a front cross section view of vessel cover 114, and one of transparent pipes 150 of closed photobioreactor 100, according to some embodiments.

Reference is made to FIG. 6. FIG. 6 constitutes a front cross section view of vessel cover 114, and one of transparent pipes 150 of closed photobioreactor 100, according to some embodiments.

Each one of vessel cover 114 and transparent pipe 150, separately, as shown in FIG. 6 may be used as vessel cover 114 and transparent pipe 150 of closed photobioreactor 100 of FIGS. 1A-B and/or as vessel cover 114 and transparent pipe 150 of closed photobioreactor 100 of FIGS. 3A-B. Specifically, the embodiments depicted in FIG. 6 relate to an optional means of connecting between transparent pipe 150 and vessel cover 114 a connection which is introduced when describing FIGS. 1A, 1B, 3A and 3B hereinabove and some embodiments thereof are further elaborated when describing FIGS. 4A and 4B. In addition, the embodiments depicted in FIG. 6 relate to an optional means of sealing transparent pipe 150 to vessel cover 114, a feature which is introduced when describing FIGS. 1A, 1B, 3A and 3B.

According to some embodiments, vessel cover 114 is connected to a plurality of transparent pipes 150. According to some embodiments, at least one of plurality of transparent pipes 150 is extending from internal cavity 104 of closed photobioreactor 100 through one of openings 120 upward. According to some embodiments, each one of plurality of transparent pipes 150 is extending from internal cavity 104 of closed photobioreactor 100 through one of openings 120 upward.

According to some embodiments, at least one of plurality of transparent pipes 150 is extending from internal cavity 104 of closed photobioreactor 100 through one of openings 120 upward towards surrounding environment 106 of closed photobioreactor 100. According to some embodiments, each one of plurality of transparent pipes 150 is extending from internal cavity 104 of closed photobioreactor 100 through one of openings 120 upward towards surrounding environment 106 of closed photobioreactor 100.

For example, transparent pipe 150 shown in FIG. 6 is portrayed as extending from internal cavity 104 upward through opening 120 towards surrounding environment 106 of closed photobioreactor 100.

According to some embodiments, at least one of plurality of transparent pipes 150 is extending from internal cavity 104, through one of openings 120 upward towards surrounding environment 106 of closed photobioreactor 100. According to some embodiments, each one of plurality of transparent pipes 150 is extending from internal cavity 104, through one of openings 120 upward towards surrounding environment 106 of closed photobioreactor 100.

According to some embodiments, at least one of plurality of transparent pipes 150 is extending downward from one of openings 120 towards internal cavity 104. According to some embodiments, each one of plurality of plurality of transparent pipes 150 is extending downward from one of openings 120 towards internal cavity 104. The up or down directions are elaborated herein above.

According to some embodiments, transparent pipe 150 is extending through opening 120. According to some embodiments, transparent pipe 150 is extending through vessel cover 114. According to some embodiments, each one of plurality of transparent pipes 150 is extending through one of plurality of openings 120.

According to some embodiments, transparent pipe 150 is retained by vessel cover 114. According to some embodiments, transparent pipe 150 is connected to vessel cover 114. According to some embodiments, transparent pipe 150 is sealed to vessel cover 114.

According to some embodiments, transparent pipe 150 comprises a transparent pipe first open end 152 and a transparent pipe second end 154. According to some embodiments, transparent pipe second end 154 is offset upward from vessel cover 114. According to some embodiments, transparent pipe second end 154 is offset downward from vessel cover 114. According to some embodiments, transparent pipe first open end 152 is at the level of opening 120, which retains it. According to some embodiments, transparent pipe first open end 152 of each one of plurality of transparent pipes 150 is at the level of vessel cover 114.

According to some embodiments, transparent pipe second end 154 is located longitudinally between vessel cover 114 and vessel floor 112.

Specifically, FIG. 6 provides a configuration of transparent pipe second end 154, which is located inside internal cavity 104 of vessel 110, and refers to embodiments in which transparent pipe 150 is extending downwards towards internal cavity 104 from vessel cover 114 or through vessel cover 114.

According to some embodiments, transparent pipe 150 comprises a transparent pipe first portion $156^a$. According to some embodiments, transparent pipe first portion $156^a$ is retaining transparent pipe 150. According to some embodiments transparent pipe first portion $156^a$ is attached to transparent pipe 150. According to some embodiments, transparent pipe first portion $156^a$ is sealed to transparent pipe 150.

According to some embodiments, transparent pipe first portion $156^a$ is located between transparent pipe first open end 152 and transparent pipe second end 154.

According to some embodiments, transparent pipe 150 has a transparent pipe first open end 152 at the longitudinal top edge thereof. It is to be understood that by defining that transparent pipe first open end 152 is located out of internal cavity 104, it is not limited to a configuration in which transparent pipe first open end 152 is necessarily above vessel cover 114, according to some embodiments. Specifically, while transparent pipe first open end 152 may be offset upward from vessel cover 114, transparent pipe first open end 152 and vessel cover 114 may be substantially at the same level, such that transparent pipe first open end 152 is located out of internal cavity 104, according to some embodiments. Transparent pipe first open end 152 is located out of internal cavity 104 when transparent pipe first open end 152 is at the level of vessel cover 114, since vessel cover 114 defines the top boundary of internal cavity 104.

Specifically, FIG. 6 represents embodiments of closed photobioreactor 100 in which transparent pipe first open end 152 is offset upward from vessel cover 114. However, closed photobioreactor 100 is not limited to transparent pipe first open ends 152, of this configuration.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodiments, transparent pipe 150 is substantially sealed to opening 120, such that aqueous medium 102, when inserted to vessel 110, is substantially isolated from surrounding environment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100.

According to some embodiments, transparent pipe 150 is substantially sealed to vessel cover 114. According to some embodiments, transparent pipe 150 is substantially sealed to vessel cover 114, such that internal cavity 104 of vessel 110 is substantially isolated from surrounding environment 106 of closed photobioreactor 100. According to some embodiments, transparent pipe 150 is substantially sealed to vessel cover 114, such that aqueous medium 102, when inserted to vessel 110, is substantially isolated from surrounding environment 106 of closed photobioreactor 100. According to some embodiments, transparent pipe 150 is substantially sealed to vessel cover 114, such that aqueous medium 102, within vessel 110, is substantially isolated from surrounding environment 106 of closed photobioreactor 100.

FIG. 6 depicts a portion of vessel cover 114 connected through opening 120 to transparent pipe 150. It is to be understood that opening 120, transparent pipe 150 and elements related thereto as depicted in FIG. 6 are optional for at least one of plurality of transparent pipes 150 of closed photobioreactor 100 (e.g. one of plurality of transparent pipes 150, some of plurality of transparent pipes 150, or each one of plurality of transparent pipes 150). Specifically, the sealing described herein may be implemented to different transparent pipes 150 described in the current disclosure.

The sealing described above may be achieved through a retention unit 140, which may comprises at least one retention member 142, according to some embodiments.

According to some embodiments, closed photobioreactor 100 further comprises a plurality of retention units 140. According to some embodiments, each of plurality of retention units 140 comprises at least one retention member 142.

According to some embodiments, each of plurality of retention units 140 comprises one retention member 142. According to some embodiments, each of plurality of retention units 140 comprises two retention members 142. According to some embodiments, each of plurality of retention units 140 comprises a plurality of retention members 142.

According to some embodiments, transparent pipe 150 is substantially sealed to opening 120. According to some embodiments, transparent pipe 150 is substantially sealed to opening 120 by at least one retention member 142. According to some embodiments, at least one retention member 142 is configured to seal transparent pipe 150 to opening 120. According to some embodiments, at least one retention member 142 is configured to fix transparent pipe 150 to opening 120. According to some embodiments, at least one retention member 142 is configured to secure transparent pipe 150 to opening 120.

According to some embodiments, transparent pipe 150 is substantially sealed to vessel cover 114. According to some embodiments, transparent pipe 150 is substantially sealed to vessel cover 114 by at least one retention member 142.

According to some embodiments, at least one retention member 142 is configured to seal transparent pipe 150 to vessel cover 114. According to some embodiments, at least one retention member 142 is configured to fix transparent pipe 150 to vessel cover 114. According to some embodiments, at least one retention member 142 is configured to secure transparent pipe 150 to vessel cover 114.

According to some embodiments, transparent pipe 150 is substantially sealed to hollow cover extension 130. According to some embodiments, transparent pipe 150 is substantially sealed to hollow cover extension 130 by at least one retention member 142. According to some embodiments, at least one retention member 142 is configured to seal transparent pipe 150 to hollow cover extension 130. According to some embodiments, at least one retention member 142 is configured to fix transparent pipe 150 to hollow cover extension 130. According to some embodiments, at least one retention member 142 is configured to secure transparent pipe 150 to hollow cover extension 130.

According to some embodiments, transparent pipe 150 is substantially sealed to hollow cover extension first portion 136. According to some embodiments, transparent pipe 150 is substantially sealed hollow cover extension first portion 136 by at least one retention member 142. According to some embodiments, at least one retention member 142 is configured to seal transparent pipe 150 to hollow cover extension first portion 136. According to some embodiments, at least one retention member 142 is configured to fix transparent pipe 150 to hollow cover extension first portion 136. According to some embodiments, at least one retention member 142 is configured to secure transparent pipe 150 to hollow cover extension first portion 136.

According to some embodiments, transparent pipe first portion 156$^a$ is substantially sealed to opening 120. According to some embodiments, transparent pipe first portion 156$^a$ is substantially sealed to opening 120 by at least one retention member 142. According to some embodiments, at least one retention member 142 is configured to seal transparent pipe first portion 156$^a$ to opening 120. According to some embodiments, at least one retention member 142 is configured to fix transparent pipe first portion 156$^a$ to opening 120. According to some embodiments, at least one retention member 142 is configured to secure transparent pipe first portion 156$^a$ to opening 120.

According to some embodiments, transparent pipe first portion 156$^a$ is substantially sealed to vessel cover 114. According to some embodiments, transparent pipe first portion 156$^a$ is substantially sealed to vessel cover 114 by at least one retention member 142. According to some embodiments, at least one retention member 142 is configured to seal transparent pipe first portion 156$^a$ to vessel cover 114. According to some embodiments, at least one retention member 142 is configured to fix transparent pipe first portion 156$^a$ to vessel cover 114. According to some embodiments, at least one retention member 142 is configured to secure transparent pipe first portion 156$^a$ to vessel cover 114.

According to some embodiments, transparent pipe first portion 156$^a$ is substantially sealed to hollow cover extension 130. According to some embodiments, transparent pipe first portion 156$^a$ is substantially sealed to hollow cover extension 130 by at least one retention member 142. According to some embodiments, at least one retention member 142 is configured to seal transparent pipe first portion 156$^a$ to hollow cover extension 130. According to some embodiments, at least one retention member 142 is configured to fix transparent pipe first portion 156$^a$ to hollow cover extension 130. According to some embodiments, at least one retention member 142 is configured to secure transparent pipe first portion 156$^a$ to hollow cover extension 130.

According to some embodiments, transparent pipe first portion 156$^a$ is substantially sealed to hollow cover extension first portion 136. According to some embodiments, transparent pipe first portion 156$^a$ is substantially sealed hollow cover extension first portion 136 by at least one retention member 142. According to some embodiments, at least one retention member 142 is configured to seal transparent pipe first portion 156$^a$ to hollow cover extension first portion 136. According to some embodiments, at least one retention member 142 is configured to fix transparent pipe first portion 156$^a$ to hollow cover extension first portion 136. According to some embodiments, at least one retention member 142 is configured to secure transparent pipe first portion 156$^a$ to hollow cover extension first portion 136.

According to some embodiments, at least one retention member 142 is disposed circumferentially between transparent pipe first portion 156$^a$ and opening 120. According to some embodiments, at least one retention member 142 is disposed circumferentially between transparent pipe first portion 156$^a$ and vessel cover 114. According to some embodiments, at least one retention member 142 is disposed circumferentially between transparent pipe 150 and opening 120. According to some embodiments, at least one retention member 142 is disposed circumferentially between transparent pipe 150 and vessel cover 114.

According to some embodiments, at least one retention member 142 is disposed longitudinally between transparent pipe second end 154 and transparent pipe first open end 152.

According to some embodiments, at least one retention member 142 is configured to limit spontaneous movement of transparent pipe 150 in the lateral and longitudinal directions.

According to some embodiments, at least one retention member 142 comprises at least one squeezable gasket. According to some embodiments, retention member 142 is a squeezable gasket. According to some embodiments, each one of retention members 142 is a squeezable gasket. According to some embodiments, at least one retention member 142 comprises at least one O-ring. According to some embodiments, retention member 142 is an O-ring. According to some embodiments, each one of retention members 142 is an O-ring. According to some embodiments, at least one retention member 142 is made of a polymeric material. According to some embodiments, at least one retention member 142 is made of rubber. According to some embodiments, at least one retention member 142 is flexible. According to some embodiments, at least one retention member 142 is expandable.

According to some embodiments, opening 120 comprises an opening internal recess 144$^a$. According to some embodiments, opening internal recess 144$^a$ is located along opening 120.

According to some embodiments, opening internal recess 144$^a$ is designed to house at least one retention member 142. According to some embodiments, at least one retention member 142 is housed within opening internal recess 144$^a$. According to some embodiments, at least one retention member 142 is accommodated within opening internal recess 144$^a$.

According to some embodiments, at least one retention member 142 is pressing transparent pipe 150 inward. According to some embodiments, at least one retention member 142 is pressing transparent pipe first portion 156 inward. It is to be understood that the term "inward" as used in this paragraph refers to the centripetal direction from the circumference of opening 120 toward transparent pipe first portion 156$^a$.

According to some embodiments, each one of transparent pipes 150 is substantially clear, such it is capable of transmitting light, such as visible light, to internal cavity 104 of vessel 110 when not disturbed by intervening objects. According to some embodiments, transparent pipe 150 is made of a transparent polymer or glass. According to some embodiments, transparent pipe 150 is made of glass.

FIG. 6 show vessel cover 114 retaining transparent pipe 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

It is to be understood that the shape of transparent pipe 150 is matching to the shape of openings 120, according to some embodiments. It is to further be understood that the shape of transparent pipe 150 is matching to the shape of hollow cover extension 130, when present, according to some embodiments.

According to some embodiments, transparent pipe 150 is externally tubular. According to some embodiments, opening 120 is circular. According to some embodiments, opening internal recess 144$^a$ is circular. According to some embodiments, opening internal recess 144$^a$ is toroidal. According to some embodiments, opening internal recess 144$^a$ is torus-shaped. According to some embodiments, opening internal recess 144$^a$ is ring-shaped.

Figure 7A:
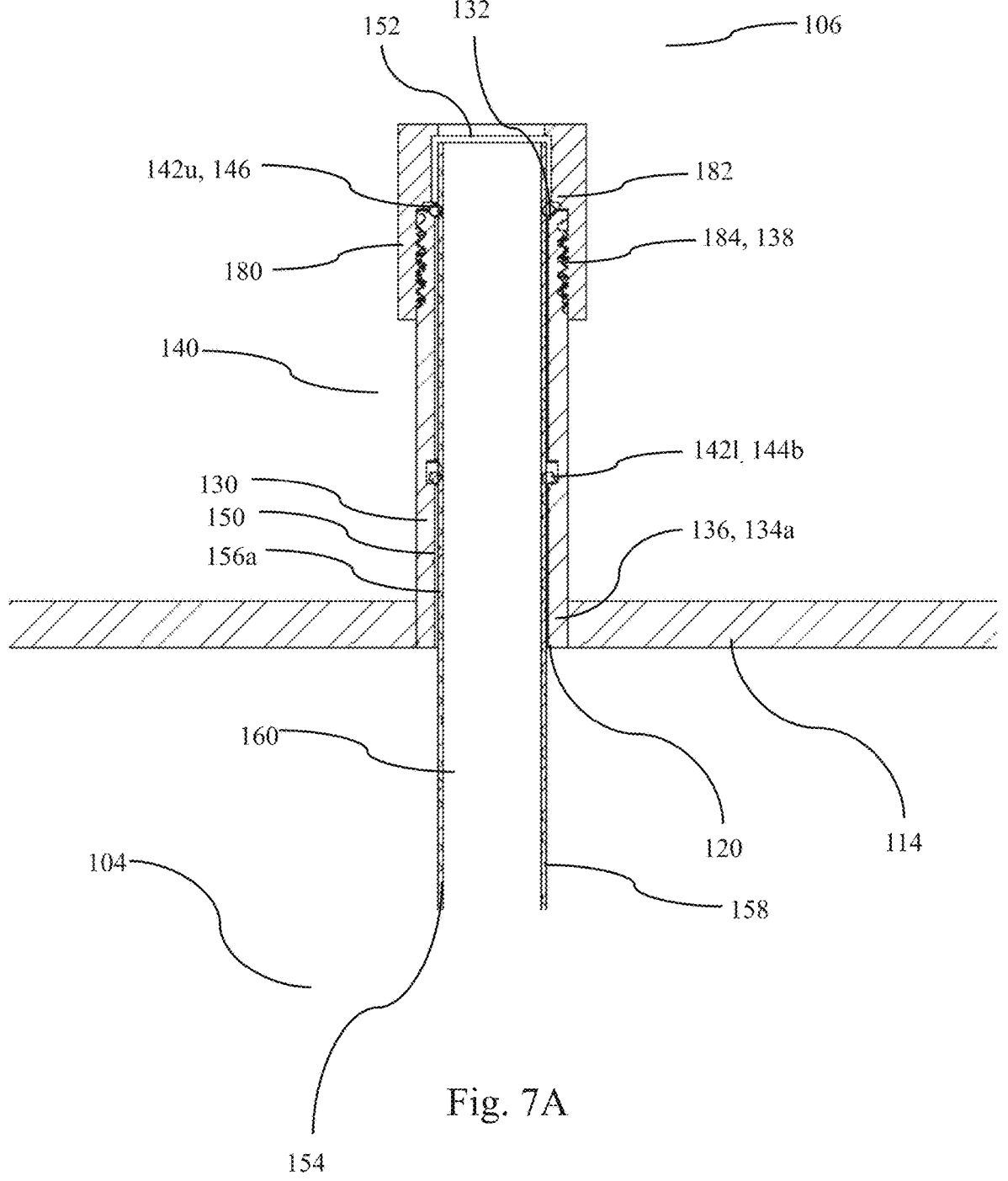
FIG. 7A constitutes a front cross section view of vessel cover 114, one of hollow cover extension 130, one of transparent pipes 150 and one of double-open caps 180 of closed photobioreactor 100, according to some embodiments.
Figure 7B:
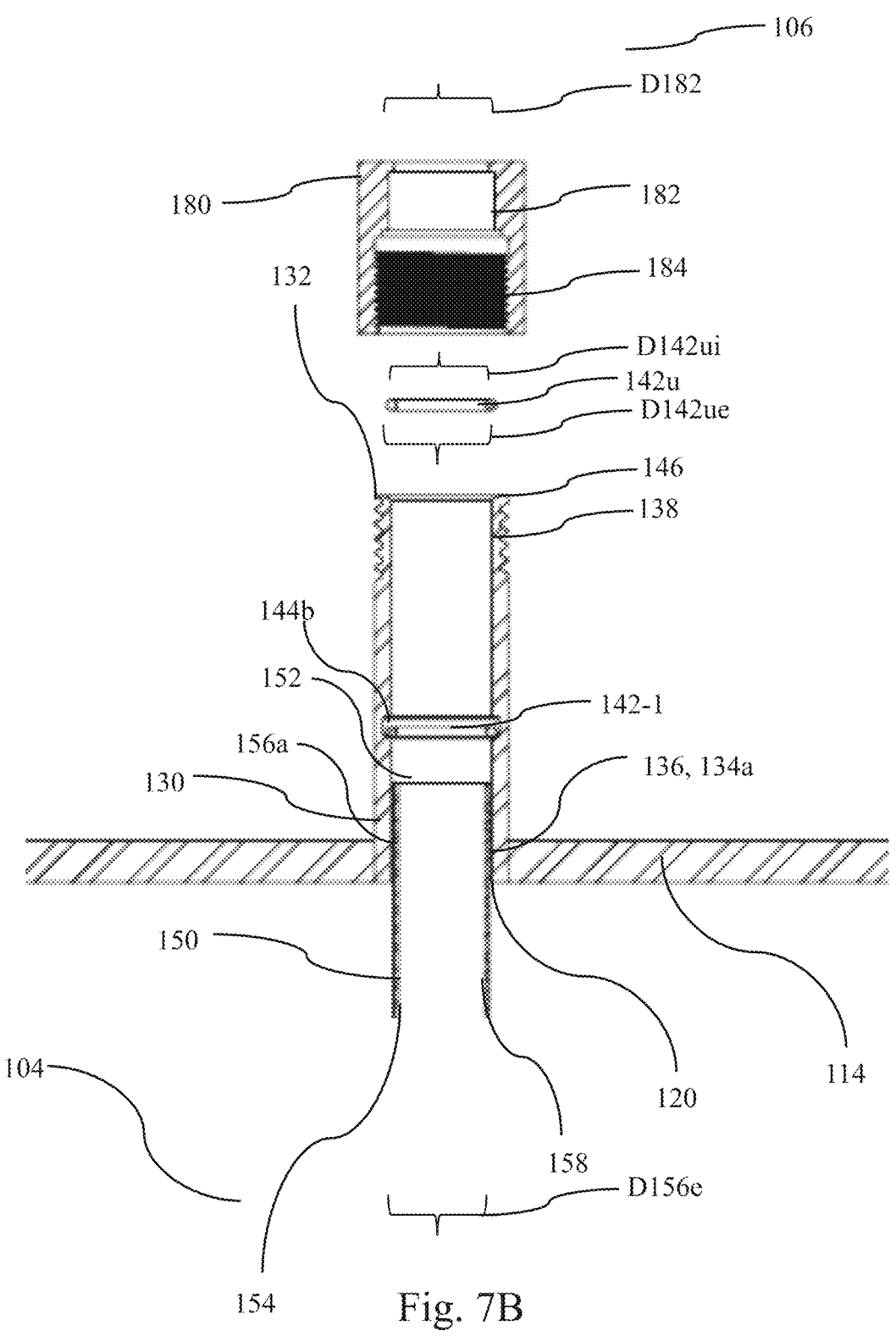
FIG. 7B constitutes an exploded view of FIG. 7A, according to some embodiments.

It is to be understood that when at least one retention member 142 is placed around transparent pipe 150, at least one retention member 142 has an internal diameter (D142$i$) equal to or larger than the external diameter (D150$e$) of transparent pipe 150, as detailed in FIGS. 7A-B. It is also to be understood that when at least one retention member 142 is placed within opening internal recess 144$^a$, at least one retention member 142 has an external diameter equal to or smaller than the diameter of opening internal recess 144$^a$.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, each one of plurality of transparent pipes 150 defines a transparent pipe lumen 160 there inside. According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, transparent pipe 150 has a transparent pipe second portion 158 located within internal cavity 104 of vessel 110.

As detailed herein, according to some embodiments, transparent pipe 150 has transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

According to some embodiments, transparent pipe lumen 160 is in fluid communication with surrounding environment 106 of closed photobioreactor 100, when not plugged. According to some embodiments, transparent pipe lumen 160 of each one of plurality of transparent pipes 150 is in fluid communication with surrounding environment 106 of closed photobioreactor 100, when not plugged. According to some embodiments, transparent pipe lumen 160 is in fluid communication with surrounding environment 106 of closed photobioreactor 100. According to some embodiments, transparent pipe lumen 160 of each one of plurality of transparent pipes 150 is in fluid communication with surrounding environment 106 of closed photobioreactor 100.

According to some embodiments, closed photobioreactor 100 further comprises a closed cap (not shown) configured to plug transparent pipe first open end 152. According to some embodiments, closed photobioreactor 100 further comprises a plurality of closed caps, each configured to plug transparent pipe first open end 152 of one of plurality of transparent pipes 150. Specifically, such closed caps are known in the art, and may include, but not limited to rubber plugs, plastic caps, glass caps, metal caps and wooden corks.

According to some embodiments, transparent pipe lumen 160 is isolated from internal cavity 104 of vessel 110. According to some embodiments, transparent pipe lumen 160 of each one of plurality of transparent pipes 150 is isolated from internal cavity 104 of vessel Reference is made to FIGS. 7A and 7B. FIG. 7A constitutes a front cross section view of vessel cover 114, one of hollow cover extension 130, one of transparent pipes 150 and one of double-open caps 180 of closed photobioreactor 100, according to some embodiments. FIG. 7B constitutes an exploded view of FIG. 7A.

Each one of vessel cover 114, double-open cap 180, hollow cover extension 130 and transparent pipe 150, separately, as shown in FIGS. 7A-B may be used as vessel cover 114 and transparent pipe 150 of closed photobioreactor 100 of FIGS. 1A-B and/or as vessel cover 114 and transparent pipe 150 of closed photobioreactor 100 of FIGS. 3A-B. Specifically, the embodiments depicted in FIGS. 7A-B relate to an optional means of connecting between transparent pipe 150 and vessel cover 114, a connection which is introduced when describing FIGS. 1A, 1B, 3A and 3B hereinabove. In addition, embodiments relating to this connection using hollow cover extension 130 are further elaborated when describing FIGS. 4A and 4B. Specifically, the embodiments depicted in FIGS. 7A-B relate to an optional means of sealing transparent pipe 150 to hollow cover extension 130 of vessel cover 114, a feature which is introduced when describing FIGS. 4A-B and 6.

More specifically, the embodiments shown in FIGS. 7A-B are similar to those described when referring to FIG. 6, with the major exception being that hollow cover extension 130 is presented in FIGS. 7A-B, and retention unit 140 comprises two retention members 142.

According to some embodiments, vessel cover 114 comprises a plurality of hollow cover extensions 130. According to some embodiments, at least one of plurality of hollow cover extensions 130 is extending from one of openings 120 upward. According to some embodiments, at least one of plurality of hollow cover extensions 130 is extending from one of openings 120 upward towards surrounding environment 106 of closed photobioreactor 100.

For example, three of plurality of hollow cover extensions 130 shown in FIGS. 7A and 7B are portrayed as extending from opening 120 upward. However, closed photobioreactor 100 is not limited to this configuration, and hollow cover extension 130 may extend from internal cavity 104, through one of openings 120 upward, or extend from internal cavity 104 upwards towards opening 120. According to some embodiments, at least one of plurality of hollow cover extensions 130 is extending from internal cavity 104, through one of openings 120 upward. According to some embodiments, at least one of plurality of hollow cover extensions 130 is extending from internal cavity 104, through one of openings 120 upward towards surrounding environment 106 of closed photobioreactor 100.

According to some embodiments, transparent pipe 150 is extending through hollow cover extension 130.

According to some embodiments, transparent pipe 150 is retained by hollow cover extension 130. According to some embodiments, transparent pipe 150 is connected to hollow cover extension 130. According to some embodiments, transparent pipe 150 is sealed to hollow cover extension 130.

According to some embodiments, hollow cover extension 130 comprises a hollow cover extension first open end 132. According to some embodiments, hollow cover extension first open end 132 is offset upward from vessel cover 114. The function of hollow cover extension first open end 132 is elaborated when referring to FIGS. 4A-B.

According to some embodiments, transparent pipe first open end 152 is offset upward from hollow cover extension first open end 132, which retains it. According to some embodiments, transparent pipe first open end 152 is offset upward from hollow cover extension first open end 132, which is attached thereto.

According to some embodiments, hollow cover extension 130 comprises a hollow to cover extension second end 134. According to some embodiments, hollow cover extension second end $134^a$ is at the at the level of vessel cover 114. According to some embodiments, hollow cover extension second end $134^a$ is at the level of openings 120.

Specifically, FIG. 7A and FIG. 7B provides hollow cover extension second end $134^a$, which is located at the level of vessel cover 114, and refers to embodiments in which hollow cover extension 130 is extending upwards from vessel cover 114. However, closed photobioreactor 100 is not limited to this configuration and may include hollow cover extension second end $134^b$, which is described in FIG. 4B.

According to some embodiments, one of hollow cover extension first open end 132 and hollow cover extension second end 134 is connected to vessel cover 114. According to some embodiments, one of hollow cover extension first open end 132 and hollow cover extension second end 134 is retained by one of openings 120 of vessel cover 114. According to some embodiments, one of hollow cover extension first open end 132 and hollow cover extension second end 134 is sealed to opening 120.

According to some embodiments, transparent pipe 150 is substantially sealed to hollow cover extension 130. According to some embodiments, transparent pipe 150 is substantially sealed to hollow cover extension 130, such that internal cavity 104 of vessel 110 is substantially isolated from surrounding environment 106 of closed photobioreactor 100. According to some embodiments, transparent pipe 150 is substantially sealed to hollow cover extension 130, such that aqueous medium 102, when inserted to vessel 110, is substantially isolated from surrounding environment 106 of closed photobioreactor 100. According to some embodiments, transparent pipe 150 is substantially sealed to hollow cover extension 130, such that aqueous medium 102, within vessel 110, is substantially isolated from surrounding environment 106 of closed photobioreactor 100.

According to some embodiments, hollow cover extension 130 comprises a hollow cover extension first portion 136. According to some embodiments, hollow cover extension first portion 136 is retaining transparent pipe 150. According to some embodiments, hollow cover extension first portion 136 is retaining one of plurality of transparent pipes 150. According to some embodiments, hollow cover extension first portion 136 is attached to transparent pipe 150. According to some embodiments, hollow cover extension first portion 136 is sealed to transparent pipe 150. According to some embodiments, hollow cover extension first portion 136 is sealed to one of plurality of transparent pipes 150.

According to some embodiments, hollow cover extension first portion 136 is retaining transparent pipe first portion 156$^a$ of transparent pipe 150. According to some embodiments, hollow cover extension first portion 136 is retaining transparent pipe first portion 156$^a$ of one of plurality of transparent pipes 150. According to some embodiments, hollow cover extension first portion 136 is attached to transparent pipe first portion 156$^a$ of transparent pipe 150. According to some embodiments, hollow cover extension first portion 136 is attached to transparent pipe first portion 156$^a$ of one of plurality of transparent pipes 150. According to some embodiments, hollow cover extension first portion 136 is sealed to transparent pipe first portion 156$^a$ of transparent pipe 150. According to some embodiments, hollow cover extension first portion 136 is sealed to transparent pipe first portion 156$^a$ of one of plurality of transparent pipes 150.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, at least one of plurality of hollow cover extensions 130 is made of a rigid material. According to some embodiments, at least one of plurality of hollow cover extensions 130 is made of a polymer, a metal alloy or a metal. According to some embodiments, at least one of plurality of hollow cover extensions 130 is made of a metal alloy. According to some embodiments, at least one of plurality of hollow cover extensions 130 is made of a metal. According to some embodiments, at least one of plurality of hollow cover extensions 130 is made of stainless steel. According to some embodiments, hollow cover extension 130 is made of a rigid material. According to some embodiments, hollow cover extension 130 made of a polymer, a metal alloy or a metal. According to some embodiments, hollow cover extension 130 is made of a metal alloy. According to some embodiments, hollow cover extension 130 is made of a metal. According to some embodiments, hollow cover extension 130 is made of stainless steel.

It is to be understood that hollow cover extension first portion 136 is made of the same material of hollow cover extension 130, according to some embodiments. Specifically, according to some embodiments, hollow cover extension first portion 136 is made of a rigid material. According to some embodiments, hollow cover extension first portion 136 is made of a polymer, a metal alloy or a metal. According to some embodiments, hollow cover extension first portion 136 is made of a metal alloy. According to some embodiments, hollow cover extension first portion 136 is made of a metal. According to some embodiments, hollow cover extension first portion 136 is made of stainless steel.

According to some embodiments, hollow cover extension 130 is welded to vessel cover 114. According to some embodiments, hollow cover extension first portion 136 is welded to vessel cover 114.

According to some embodiments, hollow cover extension first portion 136 is located between hollow cover extension second end 134 and hollow cover extension first open end 132. According to some embodiments, hollow cover extension first portion 136 is located at hollow cover extension first open end 132. According to some embodiments, hollow cover extension first portion 136 is located in proximity to hollow cover extension first open end 132. According to some embodiments, hollow cover extension first portion 136 is located in proximity to hollow cover extension second end 134$^a$.

According to some embodiments, hollow cover extension 130 comprises a hollow cover extension threaded external portion 138. According to some embodiments, hollow cover extension threaded external portion 138 is located at hollow cover extension first open end 132. According to some embodiments, hollow cover extension threaded external portion 138 is located in proximity to hollow cover extension first open end 132. According to some embodiments, hollow cover extension threaded external portion 138 is offset upward from vessel cover 114.

According to some embodiments, double-open cap threaded internal portion 184 is tubular. According to some embodiments, hollow cover extension threaded external portion 138 is tubular.

According to some embodiments, each one of transparent pipes 150 is substantially clear, such it is capable of transmitting light, such as visible light, to internal cavity 104 of vessel 110 when not disturbed by intervening objects. According to some embodiments, transparent pipe 150 is made of a transparent polymer or glass. According to some embodiments, transparent pipe 150 is made of glass.

According to some embodiments, each one of transparent pipes 150 pipes extends through one of openings 120.

FIGS. 7A and 7B show vessel cover 114 retaining transparent pipes 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

It is to be understood that the shape of transparent pipe 150 is matching to the shape of hollow cover extension 130, according to some embodiments. It is to further be understood that the shape of transparent pipe 150 is matching to the shape of openings 120, according to some embodiments.

Specifically, FIGS. 7A and 7B show vessel cover 114 connected or welded to plurality of hollow cover extensions 130 having a cylindrical shape. However, closed photobioreactor 100 is not limited to circular shaped hollow cover extensions 130. According to some embodiments, each one of plurality of hollow cover extensions 130 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of plurality of hollow cover extensions 130 is cylindrical. According to some embodiments, each one of plurality of hollow cover extensions 130 is cylindrical.

According to some embodiments, transparent pipe 150 has transparent pipe first open end 152 and transparent pipe second end 154. According to some embodiments, transparent pipe 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 defines a transparent pipe lumen 160 there inside. According to some embodiments, transparent pipe 150 is configured to accommodate light source 170 within transparent pipe lumen 160 thereof. FIGS. 7A and 7B show transparent pipe 150 with light source 170 removed, however, the relation between the elements is elaborated when referring to FIGS. 5A-E.

According to some embodiments, transparent pipe 150 has a transparent pipe second portion 158 located within internal cavity 104 of vessel 110.

As detailed herein, according to some embodiments, transparent pipe 150 has transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100, as elaborated above.

According to some embodiments, transparent pipe lumen 160 is in fluid communication with surrounding environment 106 of closed photobioreactor 100, when not plugged. According to some embodiments, closed photobioreactor 100 further comprises a closed cap (not shown) configured to plug transparent pipe first open end 152.

According to some embodiments, transparent pipe lumen 160 is isolated from internal cavity 104 of vessel 110. According to some embodiments, transparent pipe lumen 160 of each one of plurality of transparent pipes 150 is isolated from internal cavity 104 of vessel 110.

According to some embodiments, transparent pipe 150 is substantially sealed to hollow cover extension 130. According to some embodiments, transparent pipe 150 is substantially sealed to hollow cover extension 130, such that internal cavity 104 of vessel 110 is substantially isolated from surrounding environment 106 of closed photobioreactor 100. According to some embodiments, transparent pipe 150 is substantially sealed to hollow cover extension 130, such that aqueous medium 102, when inserted to vessel 110, is substantially isolated from surrounding environment 106 of closed photobioreactor 100. According to some embodiments, transparent pipe 150 is substantially sealed to hollow cover extension 130, such that aqueous medium 102, within vessel 110, is substantially isolated from surrounding environment 106 of closed photobioreactor 100.

The sealing described above may be achieved through a retention unit 140, which may comprises at least one retention member 142, according to some embodiments.

According to some embodiments, closed photobioreactor 100 further comprises a plurality of retention units 140. According to some embodiments, each of plurality of retention units 140 comprises at least one retention member 142.

According to some embodiments, each of plurality of retention units 140 comprises one retention member 142. According to some embodiments, each of plurality of retention units 140 comprises two retention members 142. According to some embodiments, each of plurality of retention units 140 comprises a plurality of retention members 142.

Specifically, FIGS. 7A-B represent an embodiment of closed photobioreactor 100, in which the sealing of transparent pipe 150 to hollow cover extension 130 is made by two retention members 142.

According to some embodiments, retention unit 140 comprises an upper retention member $142^u$ and a lower retention member $142^l$.

According to some embodiments, transparent pipe 150 is substantially sealed to hollow cover extension 130. According to some embodiments, transparent pipe 150 is substantially sealed to hollow cover extension 130 by lower retention member $142^l$ and upper retention member $142^u$. According to some embodiments, each one of lower retention member $142^l$ and upper retention member $142^u$ is configured to seal transparent pipe 150 to hollow cover extension 130. According to some embodiments, each one of lower retention member $142^l$ and upper retention member $142^u$ is configured to fix transparent pipe 150 to hollow cover extension 130. According to some embodiments, each one of lower retention member $142^l$ and upper retention member $142^u$ is configured to secure transparent pipe 150 to hollow cover extension 130.

According to some embodiments, transparent pipe 150 is substantially sealed to hollow cover extension first portion 136. According to some embodiments, transparent pipe 150 is substantially sealed to hollow cover extension first portion 136 by lower retention member $142^l$ and upper retention member $142^u$. According to some embodiments, each one of lower retention member $142^l$ and upper retention member $142^u$ is configured to seal transparent pipe 150 to hollow cover extension first portion 136. According to some embodiments, each one of lower retention member $142^l$ and upper retention member $142^u$ is configured to fix transparent pipe 150 to hollow cover extension first portion 136. According to some embodiments, each one of lower retention member $142^l$ and upper retention member $142^u$ is configured to secure transparent pipe 150 to hollow cover extension first portion 136.

According to some embodiments, transparent pipe first portion $156^a$ is substantially sealed to hollow cover extension 130. According to some embodiments, transparent pipe first portion $156^a$ is substantially sealed to hollow cover extension 130 by lower retention member $142^l$ and upper retention member $142^u$. According to some embodiments, each one of lower retention member $142^l$ and upper retention member $142^u$ is configured to seal transparent pipe first portion $156^a$ to hollow cover extension 130. According to some embodiments, each one of lower retention member $142^l$ and upper retention member $142^u$ is configured to fix transparent pipe first portion $156^a$ to hollow cover extension 130. According to some embodiments, each one of lower retention member $142^l$ and upper retention member $142^u$ is configured to secure transparent pipe first portion $156^a$ to hollow cover extension 130.

According to some embodiments, transparent pipe first portion $156^a$ is substantially sealed to hollow cover extension first portion 136. According to some embodiments, transparent pipe first portion $156^a$ is substantially sealed to hollow cover extension first portion 136 by lower retention member $142^l$ and upper retention member $142^u$. According to some embodiments, each one of lower retention member $142^l$ and upper retention member $142^u$ is configured to seal transparent pipe first portion $156^a$ to hollow cover extension first portion 136. According to some embodiments, each one of lower retention member $142^l$ and upper retention member $142^u$ is configured to fix transparent pipe first portion $156^a$ to hollow cover extension first portion 136. According to some embodiments, each one of lower retention member $142^l$ and upper retention member $142^u$ is configured to secure transparent pipe first portion $156^a$ to hollow cover extension first portion 136.

FIGS. 7A-B depict a portion of vessel cover 114 connected through hollow cover extension 130 to transparent pipe 150. It is to be understood that hollow cover extension 130, transparent pipe 150 and elements related thereto as depicted in FIGS. 7A-B are optional for at least one of plurality of transparent pipes 150 of closed photobioreactor 100 (e.g. one of plurality of transparent pipes 150, some of plurality of transparent pipes 150, or each one of plurality of transparent pipes 150). Specifically, the sealing described herein may be implemented to different transparent pipes 150 described in the current disclosure.

According to some embodiments, each one of lower retention member $142^l$ and upper retention member $142^u$ is disposed circumferentially between transparent pipe first portion $156^b$ and opening 120. According to some embodiments, each one of lower retention member $142^l$ and upper retention member $142^u$ is disposed circumferentially between transparent pipe first portion $156^b$ and vessel cover 114. According to some embodiments, each one of lower retention member $142^l$ and upper retention member $142^u$ is disposed circumferentially between transparent pipe 150 and opening 120. According to some embodiments, each one of lower retention member $142^l$ and upper retention member $142^u$ is disposed circumferentially between transparent pipe 150 and vessel cover 114.

According to some embodiments, each one of lower retention member $142^l$ and upper retention member $142^u$ is disposed longitudinally between transparent pipe second end 154 and transparent pipe first open end 152. According to some embodiments, each one of lower retention member $142^l$ and upper retention member $142^u$ is disposed longitudinally between transparent pipe second end 154 and hollow cover extension first open end 132.

According to some embodiments, each one of lower retention member $142^l$ and upper retention member $142^u$ is configured to limit spontaneous movement of transparent pipe 150 in the lateral and/or longitudinal directions.

According to some embodiments, upper retention member $142^u$ comprises at least one squeezable gasket. According to some embodiments, upper retention member $142^u$ is a squeezable gasket. According to some embodiments, each one of upper retention members $142^u$ is a squeezable gasket. According to some embodiments, at least one upper retention member $142^u$ comprises at least one O-ring. According to some embodiments, upper retention member $142^u$ is an O-ring. According to some embodiments, each one of upper retention members $142^u$ is an O-ring. According to some embodiments, at least one upper retention member $142^u$ is made of a polymeric material. According to some embodiments, upper retention member $142^u$ is made of rubber. According to some embodiments, upper retention member $142^u$ is flexible. According to some embodiments, upper retention member $142^u$ is expandable.

According to some embodiments, lower retention member $142^l$ comprises at least one squeezable gasket. According to some embodiments, lower retention member $142^l$ is a squeezable gasket. According to some embodiments, each one of lower retention members $142^l$ is a squeezable gasket. According to some embodiments, at least one lower retention member $142^l$ comprises at least one O-ring. According to some embodiments, lower retention member $142^l$ is an O-ring. According to some embodiments, each one of lower retention members $142^l$ is an O-ring. According to some embodiments, at least one lower retention member $142^l$ is made of a polymeric material. According to some embodiments, lower retention member $142^l$ is made of rubber. According to some embodiments, lower retention member $142^l$ is flexible. According to some embodiments, lower retention member $142^l$ is expandable.

According to some embodiments, hollow cover extension 130 comprises a hollow cover extension internal recess $144^b$. According to some embodiments, hollow cover extension internal recess $144^b$ is at an interior surface of hollow cover extension 130. According to some embodiments, hollow cover extension internal recess $144^b$ is positioned longitudinally between hollow cover extension second end $134^a$ and hollow cover extension first open end 132. According to some embodiments, hollow cover extension internal recess $144^b$ is positioned longitudinally between hollow cover extension second end 134 and hollow cover extension first open end 132. According to some embodiments, hollow cover extension internal recess $144^b$ is positioned longitudinally between hollow cover extension second end $134^b$ and hollow cover extension first open end 132. According to some embodiments, hollow cover extension internal recess $144^b$ is positioned longitudinally at the level of vessel cover 114.

FIGS. 7A-B represent embodiments of closed photobioreactor 100 in which hollow cover extension internal recess $144^b$ is positioned above vessel cover 114, however, embodiments, in which extension internal recess $144^b$ is positioned at the level of vessel cover 114 or below the level of vessel cover 114, are also contemplated. Specifically, hollow cover extension internal recess $144^b$ may be at the level of internal recess 144, when hollow cover extension 130 is extending between internal cavity 104 of surrounding environment 106 or extending from vessel cover 114 upwards, according to some embodiments. In addition, hollow cover extension internal recess $144^b$ may be below the level of internal recess 144, when hollow cover extension 130 is extending between internal cavity 104 of surrounding environment 106, according to some embodiments.

According to some embodiments, hollow cover extension internal recess 144$^b$ is designed to house lower retention member 142$^l$. According to some embodiments, lower retention member 142$^l$ is housed within hollow cover extension internal recess 144$^b$. According to some embodiments, lower retention member 142$^l$ is accommodated within hollow cover extension internal recess 144$^b$.

According to some embodiments, lower retention member 142$^l$ is pressing transparent pipe 150 inward. According to some embodiments, lower retention member 142$^l$ is pressing transparent pipe first portion 156 inward. It is to be understood that the term "inward" as used in this paragraph refers to the centripetal direction from the circumference of opening 120 toward transparent pipe first portion 156$^a$.

FIGS. 7A-B show vessel cover 114 retaining transparent pipe 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

It is to be understood that the shape of transparent pipe 150 is matching to the shape of openings 120, according to some embodiments. It is to further be understood that the shape of transparent pipe 150 is matching to the shape of hollow cover extension 130, when present, according to some embodiments.

According to some embodiments, hollow cover extension internal recess 144$^b$ is designed to house lower retention member 142$^l$. According to some embodiments, lower retention member 142$^l$ is housed within hollow cover extension internal recess 144$^b$. According to some embodiments, lower retention member 142$^l$ is accommodated within hollow cover extension internal recess 144$^b$.

According to some embodiments, transparent pipe 150 is externally tubular. According to some embodiments, hollow cover extension 130 is internally tubular. According to some embodiments, hollow cover extension internal recess 144$^b$ is circular. According to some embodiments, hollow cover extension internal recess 144$^b$ is toroidal. According to some embodiments, hollow cover extension internal recess 144$^b$ is torus-shaped. According to some embodiments, hollow cover extension internal recess 144$^b$ is ring-shaped.

It is to be understood that when lower retention member 142$^l$ is placed around transparent pipe 150, lower retention member 142$^l$ has an internal diameter (D142$^l$i) equal to or larger than the external diameter (D150e) of transparent pipe 150, as detailed below. It is also to be understood that when lower retention member 142$^l$ is placed within hollow cover extension internal recess 144$^b$, lower retention member 142$^l$ has an external diameter equal to or smaller than the diameter of hollow cover extension internal recess 144$^b$.

According to some embodiments lower retention member 142$^l$ is expandable. According to some embodiments, wherein lower retention member 142$^l$ is placed around transparent pipe 150, it is in an expanded state. According to some embodiments, wherein lower retention member 142$^l$ is in an expanded state, it has a lower retention member internal diameter D142$^l$i.

According to some embodiments, transparent pipe first portion 156 has an external diameter D156e. According to some embodiments, transparent pipe 150 has an external diameter D150e.

According to some embodiments, lower retention member internal diameter D142$^l$i is equal to or larger than transparent pipe first portion external diameter D156e. According to some embodiments, lower retention member internal diameter D142$^l$i is equal to or larger than transparent pipe external diameter D150e.

According to some embodiments, hollow cover extension 130 comprises a hollow cover extension slanted portion 146. According to some embodiments, hollow cover extension slanted portion 146 is at an interior surface of hollow cover extension 130. According to some embodiments hollow cover extension slanted portion 146 is positioned longitudinally at hollow cover extension first open end 132.

According to some embodiments, hollow cover extension slanted portion 146 is designed to house upper retention member 142$^u$. According to some embodiments, upper retention member 142$^u$ is housed within hollow cover extension slanted portion 146. According to some embodiments, upper retention member 142$^u$ is accommodated within hollow cover extension slanted portion 146.

According to some embodiments, upper retention member 142$^u$ is pressing transparent pipe 150 inward. According to some embodiments, upper retention member 142$^u$ is pressing transparent pipe first open end 152 inward. According to some embodiments, upper retention member 142$^u$ is pressing transparent pipe first portion 156 inward. It is to be understood that the term "inward" as used in this paragraph refers to the centripetal direction from the circumference of opening 120 toward transparent pipe 150.

FIGS. 7A-B show vessel cover 114 retaining a transparent pipe 150 having a cylindrical shape. However, closed photobioreactor 100 is not limited to circular shaped transparent pipe 150. Specifically, according to some embodiments, transparent pipe 150 may have any curvilinear shape or rectilinear shape, such as a circle, an ellipsoid, a square, a rectangle, a hexagon, an octagon, including three dimensional shapes thereof, such as cuboid and cylinder. According to some embodiments, transparent pipes 150 is cylindrical.

It is to be understood that the shape of transparent pipe 150 is matching to the shape of hollow cover extension 130.

According to some embodiments, hollow cover extension slanted portion 146 is designed to house upper retention member 142$^u$. According to some embodiments, upper retention member 142$^u$ is housed within hollow cover extension slanted portion 146. According to some embodiments, upper retention member 142$^u$ is in contact with hollow cover extension slanted portion 146.

According to some embodiments, transparent pipe 150 is externally tubular. According to some embodiments, hollow cover extension 130 is internally tubular. According to some embodiments, hollow cover extension slanted portion 146 is circular. According to some embodiments, hollow cover extension slanted portion 146 has a tapered cone shape.

It is to be understood that when upper retention member 142$^u$ is placed around transparent pipe 150, upper retention member 142$^u$ has an internal diameter (D142$^u$i) larger than the external diameter (D150e) of transparent pipe 150, as detailed below.

According to some embodiments, upper retention member 142$^u$ is expandable. According to some embodiments, wherein upper retention member 142$^u$ is placed around transparent pipe 150, it is in an expanded state. According to some embodiments, wherein upper retention member $142^u$ is in an expanded state, it has a upper retention member internal diameter $D142^u$i.

According to some embodiments, upper retention member internal diameter $D142^u$i is equal to or larger than transparent pipe first portion external diameter $D156e$. According to some embodiments, upper retention member internal diameter $D142^u$i is equal to or larger than transparent pipe external diameter $D150e$.

According to some embodiments, closed photobioreactor 100 further comprises a plurality of double-open caps 180. According to some embodiments, plurality of double-open caps 180 is at an amount equal to the number of plurality of hollow cover extensions 130. According to some embodiments, plurality of double-open caps 180 is at an amount equal to the number of plurality of transparent pipes 150.

According to some embodiments, double-open cap 180 has two open ends. According to some embodiments, double-open cap 180 is attachable to hollow cover extension first open end 132 of hollow cover extension 130. According to some embodiments, double-open cap 180 is reversibly attachable to hollow cover extension first open end 132 of hollow cover extension 130. According to some embodiments, double-open cap 180 is configured to enhance to retention of hollow cover extension 130 to transparent pipe 150. According to some embodiments, double-open cap 180 is configured to enhance to the sealing of hollow cover extension 130 to transparent pipe 150, which retains it.

According to some embodiments, double-open cap 180 has a double-open cap threaded internal portion 184. According to some embodiments, double-open cap 180 has double-open cap threaded internal portion 184, wherein double-open cap 180 is screwable to hollow cover extension threaded external portion 138 through double-open cap threaded internal portion 184.

According to some embodiments, double-open cap 180 has a double-open cap first plane 182 having a double-open cap first plane diameter D182. According to some embodiments, upper retention member $142^u$ has an upper retention member external diameter $D142^u$e. According to some embodiments, double-open cap first plane diameter double-open cap first plane diameter D182 is larger than upper retention member external diameter $D142^u$e.

According to some embodiments, when hollow cover extension 130 is capped with double-open cap 180, double-open cap first plane 182 presses against upper retention member $142^u$ downward. According to some embodiments, when hollow cover extension 130 is capped with double-open cap 180, double-open cap first plane 182 presses upper retention member $142^u$ downward against transparent pipe first open end 152. According to some embodiments, when hollow cover extension 130 is capped with double-open cap 180, double-open cap first plane 182 presses upper retention member $142^u$ downward against transparent pipe transparent pipe 150. According to some embodiments, the pressing of upper retention member $142^u$ by double-open cap first plane 18, is press fitting double-open cap 180 inward against transparent pipe first open end 152. According to some embodiments, the pressing of upper retention member $142^u$ by double-open cap first plane 182 is press fitting double-open cap 180 inward against transparent pipe 150.

It is further to be understood that the press fitting of double-open cap 180 and upper retention member $142^u$ is preventing transparent pipe 150 from longitudinally moving upwards and/or downwards.

According to some embodiments, upon screwing double-open cap threaded internal portion 184 to hollow cover extension threaded external portion 138, double-open cap first plane 182 is further press fitted between double-open cap first plane 182 and transparent pipe first open end 152.

According to some embodiments, vessel cover 114 is made of a rigid material. According to some embodiments, vessel cover 114 is made of a polymer, a metal alloy or a metal. According to some embodiments, vessel cover 114 is made of a metal alloy. According to some embodiments, vessel cover 114 is made of a metal. According to some embodiments, vessel cover 114 is made of stainless steel.

According to some embodiments, each one of plurality of transparent pipes 150 defines a transparent pipe lumen 160 there inside. According to some embodiments, plurality of transparent pipes 150 are configured to accommodate a plurality of light sources 170 within transparent pipe lumens 160 thereof. According to some embodiments, each one of plurality of transparent pipes 150 is configured to accommodate at least one light source 170 within transparent pipe lumen 160 thereof. According to some embodiments, each one of plurality of transparent pipes 150 is configured to accommodate a plurality of light sources 170 within transparent pipe lumen 160 thereof.

According to some embodiments, transparent pipe 150 has a transparent pipe second portion 158 located within internal cavity 104 of vessel 110.

As detailed herein, according to some embodiments, transparent pipe 150 has transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversibly cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

According to some embodiments, transparent pipe lumen 160 is in fluid communication with surrounding environment 106 of closed photobioreactor 100, when not plugged. According to some embodiments, transparent pipe lumen 160 of each one of plurality of transparent pipes 150 is in fluid communication with surrounding environment 106 of closed photobioreactor 100, when not plugged. According to some embodiments, transparent pipe lumen 160 is in fluid communication with surrounding environment 106 of closed photobioreactor 100. According to some embodiments, transparent pipe lumen 160 of each one of plurality of transparent pipes 150 is in fluid communication with surrounding environment 106 of closed photobioreactor 100.

According to some embodiments, closed photobioreactor 100 further comprises a closed cap (not shown) configured to plug transparent pipe first open end 152. According to some embodiments, closed photobioreactor 100 further comprises a plurality of closed caps, each configured to plug transparent pipe first open end 152 of one of plurality of transparent pipes 150. Specifically, such closed caps are known in the art, and may include, but not limited to rubber plugs, plastic caps, glass caps, metal caps and wooden corks.

According to some embodiments, transparent pipe lumen 160 is isolated from internal cavity 104 of vessel 110. According to some embodiments, transparent pipe lumen

160 of each one of plurality of transparent pipes 150 is isolated from internal cavity 104 of vessel According to some embodiments, each one of transparent pipes 150 is substantially clear, such it is capable of transmitting light, such as visible light, to internal cavity 104 of vessel 110 when not disturbed by intervening objects. According to some embodiments, transparent pipe 150 is made of a transparent polymer or glass. According to some embodiments, transparent pipe 150 is made of glass.

Figures 8A, 8B:
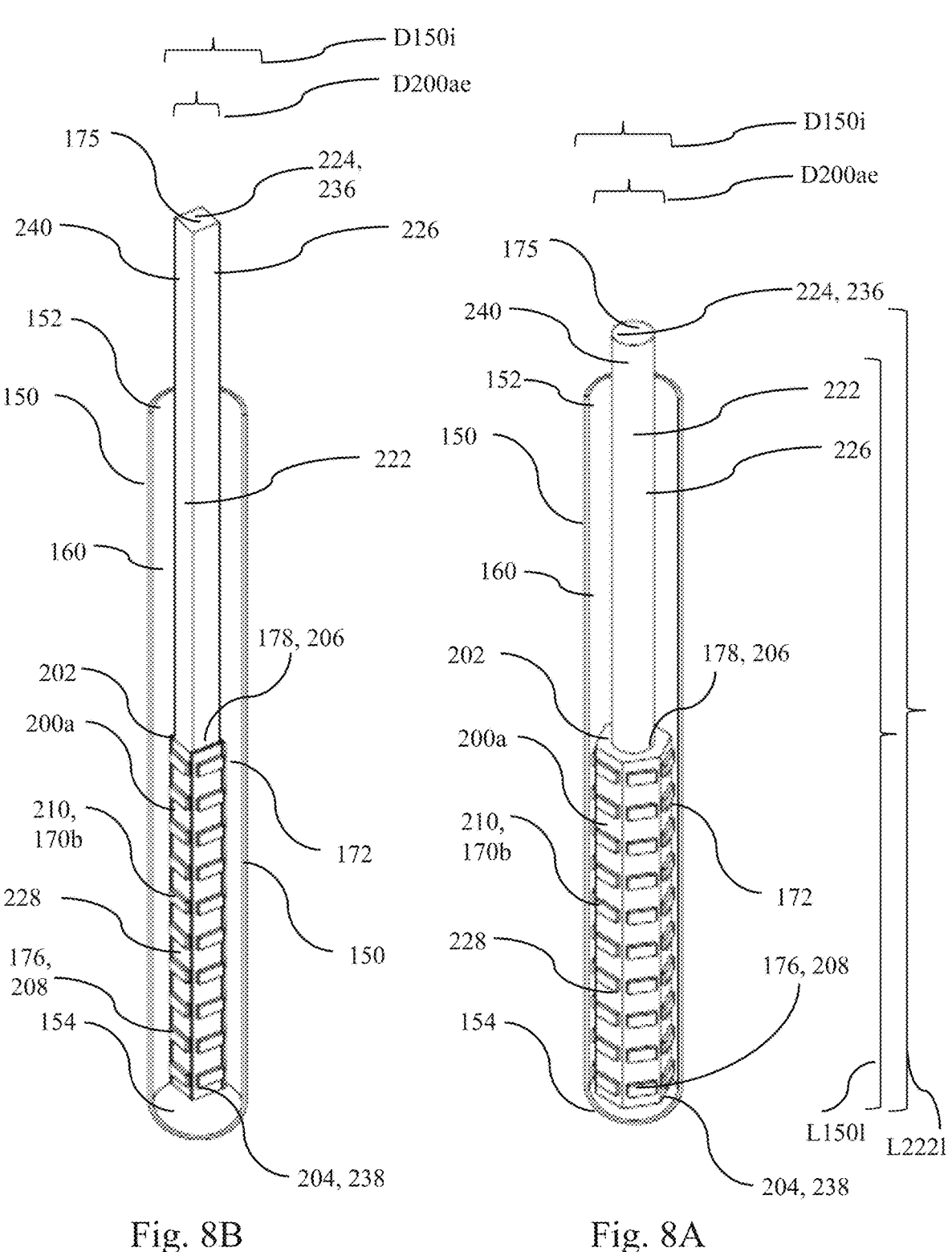
FIG. 8A constitutes a front cross section view of transparent pipe 150 having a heat pipe 222, assembled to hollow illuminating LED pipe 200$^a$ within transparent pipe lumen 160 thereof, according to some embodiments.
FIG. 8B constitutes a front cross section view of transparent pipe 150 having a heat pipe 222, assembled to hollow illuminating LED pipe 200$^a$, within transparent pipe lumen 160 thereof, according to some embodiments.
Figure 9:
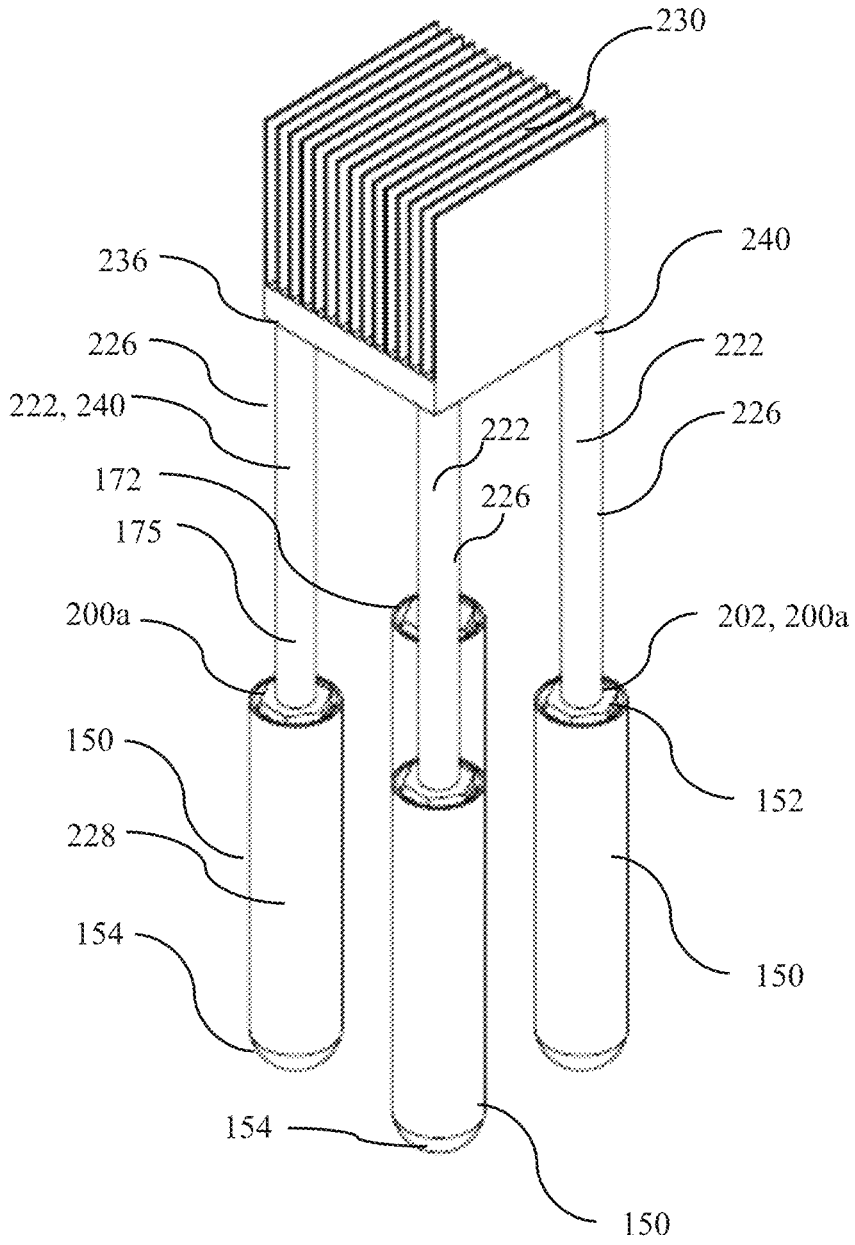
FIG. 9 constitutes a front view of four transparent pipes 150 assembled with four hollow illuminating LED pipes 200$^a$, four heat pipes 222 and at least one cooling unit 230, according to some embodiments.

Reference is made to FIGS. 8A, 8B and 9. FIG. 8A constitutes a front cross section view of transparent pipe 150 having a heat pipe 222, assembled to hollow illuminating LED pipe 200$^a$ within transparent pipe lumen 160 thereof. FIG. 8B constitutes a front cross section view of transparent pipe 150 having a heat pipe 222, assembled to hollow illuminating LED pipe 200$^a$, within transparent pipe lumen 160 thereof. FIG. 9 constitutes a front view of four transparent pipes 150 assembled with four hollow illuminating LED pipes 200$^a$, four heat pipes 222 and at least one cooling unit 230.

Each one of the transparent pipes 150 as shown in FIGS. 8A-B may be used as transparent pipe 150 of closed photobioreactor 100 of FIGS. 1A-B and/or as transparent pipe 150 of closed photobioreactor 100 of FIGS. 3A-B, all of which may further incorporate having a heat pipe 222, assembled to hollow illuminating LED pipe 200$^a$ within transparent pipe lumen 160, according to some embodiments. Specifically, the embodiments depicted in FIGS. 8A-B relate to an optional means of cooling light sources 170 (such as LED lamps 170$^b$), when inserted within transparent pipe lumen 160, a feature which is introduced when describing FIGS. 5A-E, which in their turn describe optional elements of closed photobioreactor 100 of FIGS. 1A-B and/or photobioreactor 100 of FIGS. 3A-B.

According to some embodiments, each one of transparent pipes 150 is substantially clear, such it is capable of transmitting light, such as visible light, to internal cavity 104 of vessel 110 when not disturbed by intervening objects.

According to some embodiments, transparent pipe 150 is made of a transparent polymer or glass. Transparent polymers (plastics) include, but not limited to, Poly(methyl methacrylate), polycarbonates, ethylene-vinyl acetate polymer, polystyrene sulfonate, polystyrene, polypropylene and polyethylene. According to some embodiments, transparent pipe 150 is made of glass.

According to some embodiments, each one of transparent pipes 150 pipes extends through one of openings 120 of vessel cover 114 of closed photobioreactor 100.

FIGS. 8A-B and 9 illustrate transparent pipes 150 having a cylindrical shape. However, closed photobioreactor 100 is not limited to circular shaped transparent pipe 150. Specifically, according to some embodiments, each one of transparent pipes 150 may have any curvilinear shape or rectilinear shape, such as a circle, an ellipsoid, a square, a rectangle, a hexagon, an octagon, including three dimensional shapes thereof, such as cuboid and cylinder. According to some embodiments, at least one of transparent pipes 150 is cylindrical. According to some embodiments, each one of transparent pipes 150 is cylindrical.

According to some embodiments, each one of transparent pipes 150 is connected to vessel cover 114. According to some embodiments, each one of transparent pipes 150 is attached to vessel cover 114. According to some embodiments, each one of transparent pipes 150 is connected to one of openings 120.

According to some embodiments, each one of plurality of transparent pipes 150 has a transparent pipe first open end 152 and a transparent pipe second end 154. According to some embodiments, each one of plurality of transparent pipes 150 extends along the longitudinal axis through one of openings 120, wherein transparent pipe second end 154 is located lower than transparent pipe first open end 152. According to some embodiments, transparent pipe second end 154 is located closer to vessel floor 112 than transparent pipe first open end 152. According to some embodiments, transparent pipe second end 154 is located farther than vessel cover 114 than transparent pipe first open end 152.

According to some embodiments, transparent pipe second end 154 is located within internal cavity 104. According to some embodiments, transparent pipe first open end 152 is located out of internal cavity 104.

According to some embodiments, transparent pipe 150 has a transparent pipe first open end 152 at the longitudinal top edge thereof.

According to some embodiments, transparent pipe first open end 152 is at the level of vessel cover 114. According to some embodiments, transparent pipe first open end 152 is offset upward from vessel cover 114.

According to some embodiments, each one of plurality of transparent pipes 150 defines a transparent pipe lumen 160 there inside.

According to some embodiments, transparent pipe 150 is connected to at least one of vessel cover 114 and vessel floor 112.

According to some embodiments, transparent pipe 150 has a transparent pipe first portion 156 connected to at least one of vessel cover 114 and vessel floor 112. According to some embodiments, transparent pipe first portion 156 is connected to one of vessel cover 114 and vessel floor 112. According to some embodiments, transparent pipe first portion 156$^a$ is connected to vessel cover 114.

According to some embodiments, transparent pipe 150 has a transparent pipe second portion 158 located within internal cavity 104 of vessel 110.

According to some embodiments, transparent pipe 150 is substantially sealed to opening 120. According to some embodiments, transparent pipe 150 is substantially sealed to opening 120, such that internal cavity 104 of vessel 110 is substantially isolated from surrounding environment 106 of closed photobioreactor 100. According to some embodiments, transparent pipe 150 is substantially sealed to opening 120, such that aqueous medium 102, when inserted to vessel 110, is substantially isolated from surrounding environment 106 of closed photobioreactor 100. According to some embodiments, transparent pipe 150 is substantially sealed to opening 120, such that aqueous medium 102, within vessel 110, is substantially isolated from surrounding environment 106 of closed photobioreactor 100. According to some embodiments, each one of plurality of transparent pipes 150 is substantially sealed to one of openings 120. According to some embodiments, each one of plurality of transparent pipes 150 is substantially sealed to one of openings 120, such that internal cavity 104 of vessel 110 is substantially isolated from surrounding environment 106 of closed photobioreactor 100. According to some embodiments, each one of plurality of transparent pipes 150 is substantially sealed to one of openings 120, such that aqueous medium 102, when inserted to vessel 110, is substantially isolated from surrounding environment 106 of closed photobioreactor 100. According to some embodiments, each one of plurality of transparent pipes 150 is substantially sealed to one of openings 120, such that aqueous medium 102, within vessel 110, is substantially isolated from surrounding environment 106 of closed photobioreactor 100.

As detailed herein, transparent pipe lumens 160 are exposable to surrounding environment 106 of closed photobioreactor 100, according to some embodiments. Specifically, each one of plurality of transparent pipes 150 has a transparent pipe first open end 152, said open end enables exposure of the respective transparent pipe lumen 160 to surrounding environment 106 when uncapped, according to some embodiments.

As can be seen in FIGS. 8A-B and 9, transparent pipe lumen 160 is exposed to surrounding environment 106 through transparent pipe first open end 152, according to some embodiments. It is an improvement of the currently presented closed photobioreactors 100 compared to known closed photobioreactors that uncomplicated insertion and withdrawal of light source 170, and assemblies comprising the same (e.g. plurality of heat pipes 222 and plurality of hollow illuminating LED pipes 200$^a$) into or from transparent pipe 150 is possible. Specifically, as can be seen in FIGS. 8A-E and 9, any one of heat pipes 222 and plurality of hollow illuminating LED pipes 200$^a$ is easily withdrawable from transparent pipe 150, which accommodates it.

It is noted that operation and maintenance of closed photobioreactors typically include (a) growing a microorganism culture which requires illumination (e.g. algae) inside the closed photobioreactor, with exposure to light (b) removing the microorganism culture from the closed photobioreactor; and (c) cleaning and sterilization of the closed photobioreactor interior. Typically, step (c) requires employment of high temperatures, whereas step (a) requires illumination. Illumination of step (a) is achieved by using a light source (such as LED lamps 170$^b$) located inside the closed photobioreactor. Such light sources are sensitive to high temperatures and may malfunction upon exposure to the heating conditions of step (c). The current closed photobioreactor 100 is a photobioreactor, which provides easy access and uncomplicated withdrawal of the light source from its interior. Thus, it is an improvement provided by the current disclosure that a transparent pipe 150 has a transparent pipe first open end 152, which is open and allows insertion or withdrawal of light source 170 from transparent pipe lumen 160 thereof.

According to some embodiments, transparent pipe 150 has a transparent pipe first open end 152, which is open and allows fluid communication, such as gas or liquid flow between surrounding environment 106 of closed photobioreactor 100 and transparent pipe lumen 160. However, according to some embodiments, it is an option of closed photobioreactor 100 to reversible cap or plug transparent pipe 150 at its transparent pipe first open end 152, such that transparent pipe lumen 160 is temporarily sealed from surrounding environment 106 of closed photobioreactor 100. This should not harm the function of closed photobioreactor 100, as long as the capping is reversible and fluid communication between transparent pipe lumen 160 and surrounding environment 106 of closed photobioreactor 100 is at least occasionally enabled, according to some embodiments. This importance of this type of fluid communication is elaborated herein.

As detailed herein, it is an intention of the present disclosure to provide a closed photobioreactor 100, which (a) has an internal cavity 104 substantially separated from surrounding environment 106 of closed photobioreactor 100; (b) is capable of providing sufficient illumination to aqueous medium 102 inside vessel 110; and (c) enables uncomplicated and efficient withdrawal and insertion of light sources 170, such as LED lamp 170$^b$ of each one of plurality of hollow illuminating LED pipes 200$^a$, according to some embodiments. In order to fulfill requirement (c), transparent pipe 150 is provided with transparent pipe first open end 152, and hollow cover extension 130 is provided with hollow cover extension first open end 132, according to some embodiments. Through these open ends uncomplicated and efficient withdrawal and insertion of LED lamp 170$^b$ into or from transparent pipe 150 is enabled.

According to some embodiments, transparent pipe lumen 160 is in fluid communication with surrounding environment 106 of closed photobioreactor 100, when not plugged.

According to some embodiments, closed photobioreactor 100 further comprises a closed cap (not shown) configured to plug transparent pipe first open end 152.

It is to be understood that since transparent pipe lumen 160 may come in contact with surrounding environment 106, and since aqueous medium 102 and internal cavity 104 are to be separated from surrounding environment 106, transparent pipe lumen 160 should also be separated from aqueous medium 102 and internal cavity 104 of vessel 110.

According to some embodiments, closed photobioreactor 100 further comprises a plurality of hollow illuminating LED pipes 200$^a$. According to some embodiments, closed photobioreactor 100 further comprises a plurality of heat pipes 222. According to some embodiments, closed photobioreactor 100 further comprises a plurality of hollow illuminating LED pipes 200$^a$ and a corresponding plurality of heat pipes 222.

According to some embodiments, each hollow illuminating LED pipe 200$^a$ comprises a plurality of LED lamps 170$^b$. According to some embodiments, each hollow illuminating LED pipe 200$^a$ comprises a hollow illuminating LED pipe first open end 202 and a hollow illuminating LED pipe second end 204. According to some embodiments, each hollow illuminating LED pipe 200$^a$ further comprises a hollow illuminating LED pipe internal surface 206 and a hollow illuminating LED pipe external surface 208. According to some embodiments, each hollow illuminating LED pipe 200$^a$ further comprises a hollow illuminating LED pipe lumen 210 within internal surface 206 of hollow illuminating LED pipe 200$^a$.

According to some embodiments, LED lamp 170$^b$ comprises heat a emitting plane 178. According to some embodiments, LED lamp 170$^b$ comprises heat an illuminating plane 176. According to some embodiments, each one of plurality of LED lamps 170$^b$ comprises a heat emitting plane 178 and an illuminating plane 176. As detailed above, LED lamps having separate surfaces, one of which is emitting light and the other emitting heat, is known in the art. It is to be understood that an illuminating plane 176 may also emit heat.

According to some embodiments, hollow illuminating LED pipe first open end 202 is facing vessel cover 114. According to some embodiments, hollow illuminating LED pipe first open end 202 is facing transparent pipe first open end 152. According to some embodiments, hollow illuminating LED pipe first open end 202 is facing vessel cover 114, when hollow illuminating LED pipe 200$^a$ is inserted within transparent pipe lumen 160. According to some embodiments, hollow illuminating LED pipe first open end 202 is facing transparent pipe first open end 152, when hollow illuminating LED pipe 200$^a$ is inserted within transparent pipe lumen 160.

According to some embodiments, hollow illuminating LED pipe second end 204 is facing vessel floor 112. According to some embodiments, hollow illuminating LED pipe second end 204 is facing transparent pipe second end 154. According to some embodiments, hollow illuminating LED pipe second end 204 is facing vessel floor 112, when hollow illuminating LED pipe 200$^a$ is inserted within transparent pipe lumen 160. According to some embodiments, hollow illuminating LED pipe second end 204 is facing transparent pipe second end 154, when hollow illuminating LED pipe 200$^a$ is inserted within transparent pipe lumen 160.

According to some embodiments, hollow illuminating LED pipe internal surface 206 is connected to heat emitting plane 178 of each one of plurality of LED lamps 170$^b$. According to some embodiments, hollow illuminating LED pipe internal surface 206 is formed by plurality of heat emitting planes 178 of plurality of LED lamps 170$^b$.

According to some embodiments, hollow illuminating LED pipe external surface 208 is connected to illuminating plane 176 of each one of the plurality of LED lamps 170$^b$. According to some embodiments, hollow illuminating LED pipe external surface 208 is formed by plurality of LED lamp illuminating plane 176 of plurality of LED lamps 170$^b$.

According to some embodiments, each one of the plurality of hollow illuminating LED pipes 200$^a$ in accommodated within transparent pipe lumen 160 of each one of the plurality of transparent pipes 150. According to some embodiments, each of the plurality of hollow illuminating LED pipes 200$^a$ in accommodated within each one of the plurality of transparent pipes 150.

According to some embodiments, each heat pipe 222 comprises a heat pipe internal surface 224 and a heat pipe external surface 226. According to some embodiments, each heat pipe 222 further comprises a heat pipe first closed end 236, and a heat pipe second closed end 238. According to some embodiments, each heat pipe 222 further a comprises a heat pipe heat transferring portion 228 extending between heat pipe first closed end 236 and heat pipe second closed end 238. According to some embodiments, each heat pipe 222 is closed at both ends, i.e. heat pipe first closed end 236 and heat pipe second closed end 238, thereby forming a sealed pipe, configured to accommodate a fluid therewithin. According to some embodiments, heat pipe 222 is a sealed pipe, which does not enable fluid communication between the lumen thereof, and transparent pipe lumen 160, wherein the lumen of heat pipe 222 is defined within heat pipe internal surface 224 and between heat pipe first closed end 236, and heat pipe second closed end 238.

As used herein, the term "heat pipe" refers to a thermal energy transfer vessel that combines the principles of both thermal conductivity and phase transition to effectively transfer heat or thermal energy at a hot interface between two solid surfaces, such as between heat emitting plane 178 of hollow illuminating LED pipe 200$^a$ and heat pipe heat transferring portion 228. Typically, heat pipes are partially filled with a working or cooling fluid and then sealed. At the hot interface between the two solid surfaces, the cooling fluid is in contact with a thermally conductive solid surface of the heat pipe, and as a result turns into a vapor by absorbing heat from the hot interface. The vapors then travels along the heat pipe to a cold surface and condenses back into a fluid by releasing the latent heat through said cold surface. The fluid then returns to the hot interface through either capillary action, centrifugal force, or gravity, and the cycle repeats.

According to some embodiments, heat pipe external surface 226 comprises heat pipe heat transferring portion 228 and a heat pipe cooling portion 240. According to some embodiments, heat pipe first closed end 236 is located at the end of heat pipe cooling portion 240. According to some embodiments, heat pipe second closed end 238 is located at the end of heat pipe heat transferring portion 228. According to some embodiments, heat pipe heat transferring portion 228 is located between heat pipe first closed end 236 and heat pipe second closed end 238.

According to some embodiments, heat pipe second closed end 238 is facing transparent pipe second end 154. According to some embodiments, heat pipe second closed end 238 is facing vessel floor 112. According to some embodiments, each one of heat pipe second closed ends 238 is facing transparent pipe second end 154 of transparent pipe 150, which accommodates it. According to some embodiments, each one of heat pipe second closed end 238 is facing vessel floor 112.

According to some embodiments, first closed end 236 is extending through opening 120. According to some embodiments, first closed end 236 is extending through vessel cover 114. According to some embodiments, first closed end 236 is extending through transparent pipe first open end 152. According to some embodiments, each one of first closed ends 236 is extending through on of plurality of opening 120. According to some embodiments, each one of first closed ends 236 is extending through vessel cover 114. According to some embodiments, each one of first closed end 236 is extending through one of transparent pipe first open end 152.

According to some embodiments, heat pipe 222 is accommodated within hollow illuminating LED pipe lumen 210. According to some embodiments, heat pipe 222 is accommodated within hollow illuminating LED pipe internal surface 206. According to some embodiments, heat pipe 222 is accommodated within hollow illuminating LED pipe lumen 210, such that heat pipe external surface 226 contacts internal surface 206 of hollow illuminating LED pipes 200$^a$. According to some embodiments, each of heat pipes 222 is accommodated within hollow illuminating LED pipe lumen 210 of one of the hollow illuminating LED pipes 200$^a$. According to some embodiments, each of heat pipes 222 is accommodated within hollow illuminating LED pipe internal surface 206 of one of hollow illuminating LED pipes 200$^a$. According to some embodiments, each of heat pipes 222 is accommodated within hollow illuminating LED pipe lumen 210 of one of the hollow illuminating LED pipes 200$^a$, such that each one of heat pipe external surfaces 226 contacts internal surface 206 of one of hollow illuminating LED pipes 200$^a$.

According to some embodiments, heat pipe heat transferring portion 228 is accommodated within hollow illuminating LED pipe lumen 210 and/or hollow illuminating LED pipe internal surface 206 of one of the hollow illuminating LED pipes 200$^a$. According to some embodiments, heat pipe heat transferring portion 228 is inserted into hollow illuminating LED pipe lumen 210. According to some embodiments heat pipe heat transferring portion 228 is accommodated within hollow illuminating LED pipe lumen 210. According to some embodiments, heat pipe heat transferring portion 228 is accommodated within hollow illuminating LED pipe internal surface 206. According to some embodiments, heat pipe heat transferring portion 228 is accommodated within hollow illuminating LED pipe lumen 210, such that heat pipe external surface 226 contacts internal surface 206 of hollow illuminating LED pipes 200$^a$. According to some embodiments, each of heat pipe heat transferring portions 228 is accommodated within hollow illuminating LED pipe lumen 210 of one of the hollow illuminating LED pipes 200$^a$. According to some embodiments, each of heat pipe heat transferring portions 228 is accommodated within hollow illuminating LED pipe internal surface 206 of one of hollow illuminating LED pipes 200$^a$. According to some embodiments, each of heat pipe heat transferring portions 228 is accommodated within hollow illuminating LED pipe lumen 210 of one of the hollow illuminating LED pipes 200$^a$, such that each one of heat pipe external surfaces 226 at heat pipe heat transferring portion 228 contacts internal surface 206 of one of hollow illuminating LED pipes 200$^a$.

According to some embodiments, heat pipe external surface 226 is in contact with hollow illuminating LED pipe internal surface 206. According to some embodiments, heat pipe external surface 226 is in contact with heat emitting plane 178 of each one of plurality of LED lamps 170$^b$. According to some embodiments, heat pipe heat transferring portion 228 is in contact with hollow illuminating LED pipe internal surface 206. According to some embodiments, heat pipe heat transferring portion 228 is in contact with heat emitting plane 178 of each one of plurality of LED lamps 170$^b$. According to some embodiments, hollow illuminating LED pipe internal surface 206 is integral with heat emitting plane 178 of each one of plurality of LED lamps 170$^b$ and hollow illuminating LED pipe internal lumen 210.

According to some embodiments, heat pipe first closed end 236 is extending through transparent pipe first open end 152, which accommodates it. According to some embodiments, heat pipe first closed end 236 is offset upward from transparent pipe first open end 152. According to some embodiments, heat pipe first closed end 236 is located out of transparent pipe first open end 152, as illustrated at FIGS. 8A-8B and FIG. 9. According to some embodiments, heat pipe cooling portion 240 is located out of transparent pipe first open end 152. According to some embodiments, heat pipe cooling portion 240 is extending through transparent pipe first open end 152. Without wishing to be bound by any theory or mechanism of action, heat pipe heat transferring portion 228 contacts LED lamp heat emitting plane 178 of plurality of hollow illuminating LED pipes 200$^a$, and, as a result is heated thereby. As explained, heat pipes, such as heat pipe 222, are configured to transfer heat from a cold position to a hot position, and vice versa. As a result of the configuration of heat pipe 222 and hollow illuminating LED pipe 200$^a$ shown in FIGS. 8A-B and 9, heat is initially transferred to heat pipe heat transferring portion 228, and as a result, the temperature of heat pipe heat transferring portion 228 is higher than that of heat pipe cooling portion 240. Of the positions of heat pipe 222, which are out of hollow illuminating LED pipe 200$^a$, positions closer to hollow illuminating LED pipe 200$^a$ (for example, positions in proximity with hollow illuminating LED pipe first open end 202) are generally hotter that positions away from hollow illuminating LED pipe 200$^a$. Therefore, the positions which are out of hollow illuminating LED pipe 200$^a$ may be considered as part of heat pipe cooling portion 240, wherein the positions away from hollow illuminating LED pipe 200$^a$ being more cooling. It also may be regarded that positions away from hollow illuminating LED pipe 200$^a$ (e.g. positions in proximity with evaporation pipe first open end 236) constitute heat pipe cooling portion 240.

According to some embodiments, each heat pipe 222 has a longitudinal length L222*l*, as illustrated at FIG. 8A. According to some embodiments, longitudinal length L222*l* of each heat pipe 222 is longer than longitudinal length L150*l* of transparent pipe 150, which accommodates it. According to some embodiments, longitudinal length L222*l* of each heat pipe 222 is longer than longitudinal length L150*l* of transparent pipe 150, which accommodates it, by at least 1%, or by at least 10%, or by at least 20%, or by at least 30%, or by at least 40%, or by at least 50%. Each possibility represents a separate embodiment. According to some embodiments, longitudinal length L222*l* of each heat pipe 222 is longer than longitudinal length L150*l* of each transparent pipe 150, by 5% to 25%.

According to some embodiments, each hollow illuminating LED pipe 200$^a$ comprises at least one LED strip 200$^b$, wherein each LED strip 200$^b$ comprises a plurality of LED lamps 170$^b$. According to some embodiments, each hollow illuminating LED pipe 200$^a$ comprises a plurality of LED lamps 170$^b$ mounted to a circuit board (not shown). According to some embodiments, the circuit board is attached to heat pipe heat transferring portion 228. According to some embodiments, the circuit board is integral with LED lamp heat emitting plane 178 of plurality of hollow illuminating LED pipes 200$^a$. According to some embodiments, the circuit board is a printed circuit board (PCB). The circuit board can be a flexible circuit board or a rigid circuit board.

As used herein, the terms "printed circuit board" and "PCB" are used interchangeably and broadly mean any structure comprising at least one conductive trace. A printed circuit board (PCB) can comprise multiple layers, such as a conductive layer covered with an insulating layer. A PCB can also comprise a third layer on top of the insulating layer, creating a conductor-insulator-conductor sandwich structure. A PCB doesn't necessarily have to be manufactured by an imprinting process. For example, a PCB can be manufactured by an etching process and can still be a PCB. The term "printed circuit board" is used in its broadest sense and refers to a structure, which is preferably planar, that comprises one or more conductive structures. The PCB can be a flexible PCB or a rigid PCB.

According to some embodiments, each hollow illuminating LED pipe 200$^a$ is formed from the plurality of LED lamps 170$^b$ and heat pipe external surface 226. According to some embodiments, hollow illuminating LED pipe internal surface 206 is connected or attached to heat pipe external surface 226. According to some embodiments, hollow illuminating LED pipe internal surface 206 is heat pipe external surface 226, wherein the plurality of LED lamps 170$^b$ is attached to heat pipe external surface 226. According to some embodiments, hollow illuminating LED pipe 200$^a$ is formed by permanently attaching the plurality of LED lamps 170$^b$ to heat pipe external surface 226, thereby attaching LED lamp heat emitting plane 178 of plurality of hollow illuminating LED pipes 200$^a$ to heat pipe external surface 226.

According to some embodiments, each hollow illuminating LED pipe 200$^a$ is formed from the plurality of LED lamps 170$^b$ and heat pipe heat transferring portion 228. According to some embodiments, hollow illuminating LED pipe internal surface 206 is connected or attached to heat pipe heat transferring portion 228. According to some embodiments, hollow illuminating LED pipe internal surface 206 is heat pipe heat transferring portion 228, wherein the plurality of LED lamps 170$^b$ is attached to heat pipe heat transferring portion 228. According to some embodiments, heat emitting plane 178 of each one of plurality of LED lamps 170$^b$ is attached to heat pipe heat transferring portion 228. According to some embodiments, hollow illuminating LED pipe 200$^a$ is formed by permanently attaching the plurality of LED lamps 170$^b$ to heat pipe heat transferring portion 228, thereby attaching LED lamp heat emitting plane 178 to heat pipe heat transferring portion 228. Without wishing to be bound by any theory or mechanism of action, LED lamp heat emitting plane 178 is attached to heat pipe heat transferring portion 228, and, as a result heat is transferred therebetween. According to some embodiments, heat pipe 222 is configured to reduce the temperature of LED lamp heat emitting plane 178 attached to heat pipe heat transferring portion 228, as explained herein in accordance with some embodiments.

According to some embodiments, each one of plurality of hollow illuminating LED pipes 200$^a$ and/or plurality of heat pipes 222, separately, has a curvilinear shape or a rectilinear shape, such as a circle, an ellipsoid, a square, a rectangle, a hexagon, an octagon, including three dimensional shapes thereof, such as cuboid and cylinder. Each possibility represents a separate embodiment of the present invention. The shape of heat pipe 222 and hollow illuminating LED pipe 200$^a$ may be similar, as shown in FIG. 8B (both cuboids), or different, as shown in FIG. 8A (heat pipe 222 is shown as cylindrical and hollow illuminating LED pipe 200$^a$ is shown as a hexagonal prism). According to some embodiments, the shape of heat pipe heat transferring portion 228 is similar to the shape of hollow illuminating LED pipe internal surface 206. According to some embodiments, the shape of heat pipe external surface 226 is similar to the shape of hollow illuminating LED pipe internal surface 206.

According to some embodiments, hollow illuminating LED pipe internal surface 206 and/or hollow illuminating LED pipe lumen 210 has a shape selected from the group consisting of circular, triangular, square, pentagonal, hexagonal, heptagonal, octagonal, or any other suitable three dimensional shapes and polygons thereof. Each possibility represents a separate embodiment of the present invention. According to some embodiments, hollow illuminating LED pipe internal lumen 210 has the shape of hollow illuminating LED pipe internal surface 206. According to some embodiments, heat pipe external surface 226 and/or heat pipe heat transferring portion 228 have a shape adapted to be in contact with and/or be accommodated within, hollow illuminating LED pipe lumen 210 and/or hollow illuminating LED pipe internal surface 206.

According to some embodiments, each hollow illuminating LED pipe 200$^a$ comprises three LED strips 200$^b$, so that hollow illuminating LED pipe internal surface 206 has a triangular shape (not shown). According to some embodiments, heat pipe external surface 226 and/or heat pipe heat transferring portion 228 has a triangular shape, adapted to be accommodated within hollow illuminating LED pipe lumen 210 and/or hollow illuminating LED pipe internal surface 206. According to some embodiments, heat pipe external surface 226 and/or heat pipe heat transferring portion 228 has a triangular shape, adapted to be in contact with hollow illuminating LED pipe lumen 210 and/or hollow illuminating LED pipe internal surface 206.

According to some embodiments, each hollow illuminating LED pipe 200$^a$ comprises four LED strips 200$^b$, so that hollow illuminating LED pipe internal surface 206 has a square shape, as illustrated at FIG. 8B. According to some embodiments, heat pipe external surface 226 and/or heat pipe heat transferring portion 228 has a square shape, adapted to be accommodated within hollow illuminating LED pipe lumen 210 and/or hollow illuminating LED pipe internal surface 206. According to some embodiments, heat pipe external surface 226 and/or heat pipe heat transferring portion 228 has a square shape, adapted to be in contact with hollow illuminating LED pipe lumen 210 and/or hollow illuminating LED pipe internal surface 206.

According to some embodiments, each hollow illuminating LED pipe 200$^a$ comprises five LED strips 200$^b$, so that hollow illuminating LED pipe internal surface 206 has a pentagonal shape (not shown). According to some embodiments, heat pipe external surface 226 and/or heat pipe heat transferring portion 228 has a pentagonal shape, adapted to be accommodated within hollow illuminating LED pipe lumen 210 and/or hollow illuminating LED pipe internal surface 206. According to some embodiments, heat pipe external surface 226 and/or heat pipe heat transferring portion 228 has a pentagonal shape, adapted to be in contact with hollow illuminating LED pipe lumen 210 and/or hollow illuminating LED pipe internal surface 206.

According to some embodiments, each hollow illuminating LED pipe 200$^a$ comprises six LED strips 200$^b$, so that hollow illuminating LED pipe internal surface 206 has a hexagonal shape (not shown). According to some embodiments, heat pipe external surface 226 and/or heat pipe heat transferring portion 228 has a hexagonal shape, adapted to be accommodated within hollow illuminating LED pipe lumen 210 and/or hollow illuminating LED pipe internal surface 206. According to some embodiments, heat pipe external surface 226 and/or heat pipe heat transferring portion 228 has a hexagonal shape, adapted to be in contact with hollow illuminating LED pipe lumen 210 and/or hollow illuminating LED pipe internal surface 206.

According to some embodiments, each hollow illuminating LED pipe 200$^a$ comprises a plurality of LED strips 200$^b$, so that hollow illuminating LED pipe internal surface 206 has a circular shape. According to some embodiments, heat pipe external surface 226 and/or heat pipe heat transferring portion 228 has a circular shape, adapted to be accommodated within hollow illuminating LED pipe lumen 210 and/or hollow illuminating LED pipe internal surface 206. According to still some embodiments, heat pipe external surface 226 and/or heat pipe heat transferring portion 228 has a circular shape, adapted to be in contact with hollow illuminating LED pipe lumen 210 and/or hollow illuminating LED pipe internal surface 206.

According to some embodiments, each heat pipe 222 is made from a thermal conducting material. According to some embodiments, heat pipe 222 is made of a metal or a metal alloy. According to some embodiments, heat pipe 222 is made of a metal. According to some embodiments, heat pipe 222 is made of a metal alloy. According to some embodiments, heat pipe 222 is made of stainless steel. According to some embodiments, said thermal conducting material is selected from: steel, silver, copper, gold, aluminum, aluminum nitride, silicone, silicon carbide, tungsten, graphite, zinc, and combinations and alloys thereof. Each possibility represents a separate embodiment of the present invention.

According to some embodiments, each heat pipe heat transferring portion 228 is made from a thermal conducting material. According to some embodiments, heat pipe heat transferring portion 228 is made of a metal or a metal alloy. According to some embodiments, heat pipe heat transferring portion 228 is made of a metal. According to some embodiments, heat pipe heat transferring portion 228 is made of a metal alloy. According to some embodiments, heat pipe heat transferring portion 228 is made of stainless steel. According to some embodiments, said thermal conducting material is selected from: steel, silver, copper, gold, aluminum, aluminum nitride, silicone, silicon carbide, tungsten, graphite, zinc, and combinations and alloys thereof. Each possibility represents a separate embodiment of the present invention.

According to some embodiments, each heat pipe 222 contains LED cooling fluid 175. According to some embodiments, each heat pipe 222 contains LED cooling fluid 175 enclosed within heat pipe internal surface 224, heat pipe first closed end 236 and heat pipe second closed end 238. According to some embodiments, each heat pipe 222 is at least partially filled with LED cooling fluid 175. According to some embodiments, a portion of heat pipe 222 is filled with LED cooling fluid 175. According to some embodiments, each heat pipe is partially filled with LED cooling fluid 175 under vacuum. According to some embodiments, heat pipe internal surface 224 is partially filled with LED cooling fluid 175 under vacuum. According to further embodiments, each heat pipe 222 comprises LED cooling fluid 175 in the liquid state and in the gas state, in equilibrium.

Without wishing to be bound by any theory or mechanism of action, since heat pipe 222 is made from a thermal conducting material, heat pipe 222 is configured to enable heat transfer between heat pipe external surface 226 and heat pipe internal surface 224. According to some embodiments, LED cooling fluid 175 is in contact with heat pipe internal surface 224, therefore enabling heat or thermal energy transfer between LED cooling fluid 175 and the heat emitting plane 178 of each one of plurality of LED lamps 170ᵇ. According to further embodiments, LED cooling fluid 175 is in contact with heat pipe heat transferring portion 228, therefore enabling heat or thermal energy transfer between LED cooling fluid 175 and heat emitting plane 178 of each one of plurality of LED lamps 170ᵇ.

According to some embodiments, upon the partially filling of LED cooling fluid 175 within heat pipe internal surface 224, heat transfer between LED cooling fluid 175 and heat pipe heat transferring portion 228 is enabled. It is to be understood that LED cooling fluid 175 may be in an equilibrium between a gas and liquid state inside heat pipe 222, and that, in light of this, the term "partially filling" refers to the liquid material, whereas gas molecules of LED cooling fluid 175 are present in the unfilled space.

According to some embodiments, LED cooling fluid 175 comprises at least one substance selected from water, organic compounds, corrosion inhibitors, antifreeze compounds, and combinations thereof. Each possibility represents a separate embodiment of the present invention. The organic compounds can be selected from glycol compounds (such as but not limited to, ethylene glycol, diethylene glycol, propylene glycol, or polyalkylene glycol (PAG)) or oils (such as but not limited to, vegetable oils, silicone oils, or fluorocarbon oils). Each possibility represents a separate embodiment of the present invention.

According to some embodiments, LED cooling fluid 175 comprises lubricating oils, such as but not limited to, vacuum pump lubricants. According to some embodiments, said lubricating oils are lubricating oils coolers, adapted to transfer heat from metallic components resulting in the cooling thereof. Said lubricants can be selected from synthetic oils or mineral oils. The lubricants can be selected from polyalphaolefins (PAOs), diesters, polyolesters (POEs), petroleum oils, combinations and derivatives thereof. Each possibility represents a separate embodiment of the present invention.

According to some embodiments, heat pipe heat transferring portion 228 is in contact with heat emitting plane 178 of each one of plurality of LED lamps 170ᵇ. According to some embodiments, heat pipe heat transferring portion 228 is in contact with heat emitting plane 178 of each one of plurality of LED lamps 170ᵇ, thereby enabling the transformation of thermal energy therebetween, resulting in heating the lubricating oils residing in the vicinity of an internal surface of heat pipe heat transferring portion 228, so that the viscosity and/or density of the lubricating oils is decreased.

According to some embodiments, following the decrease in viscosity and/or density of the lubricating oils, the heated lubricating oils diffuse from heat pipe heat transferring portion 228 towards heat pipe cooling portion 240 (due to the change in viscosity and/or density gradient), where the heated lubricating oils releases its latent thermal energy and warms heat pipe cooling portion 240. Following the release of its latent thermal energy, the heated lubricating oils cools and regain their initial state (e.g. the initial viscosity and/or density), and due to gravity force flows/diffuses back to heat pipe heat transferring portion 228, to repeat the heat transfer cycle.

According to some embodiments, LED cooling fluid 175 has a boiling point in the range of 10° C. to 90° C. According to further embodiments, the boiling point of LED cooling fluid 175 is in the range of 15° C. to 50° C. According to some embodiments, LED cooling fluid 175 is an oil, having a boiling point higher than 150° C. to about 90° C.

According to some embodiments, hollow illuminating LED pipe 200ᵃ has hollow illuminating LED pipe external diameter D200ᵃe. According to some embodiments, transparent pipe 150 has transparent pipe internal diameter Transparent pipe internal diameter D150i (as shown in FIG. 5B). According to some embodiments, upon the accommodation, a positive gap 172 exists between hollow illuminating LED pipe external diameter D208e and transparent pipe internal diameter D150i. As detailed with respect to FIGS. 5A-E, one of the advantages of the various configurations of closed photobioreactor 100, is that light source 170, including any assembly connected thereto (e.g. hollow illuminating LED pipe 200ᵃ, heat pipe 222, etc.) may be easily withdrawn from transparent pipe 150 to enable convenient and simple maintenance of closed photobioreactor 100. According to some embodiments, any one of hollow illuminating LED pipe 200ᵃ is withdrawable from transparent pipe 150.

As shown in FIGS. 8A-8B and 9, according to some embodiments, one of the functions of plurality of hollow illuminating LED pipes 200ᵃ is to illuminate internal cavity 104 of vessel 110 through transparent pipe 150—a function, which is achieved by plurality of light sources 170, such as plurality of LED lamps 170ᵇ. In addition, as detailed when referring to FIGS. 5A-E, one of the advantages of closed photobioreactor 100 is the ability to keep plurality of light sources 170 from overheating, thereby simplifying the maintenance and reducing the maintenance actions required to keep closed photobioreactor 100 in acceptable working condition. This advantage may be achieved by using the plurality of heat pipes 222, according to some embodiments.

According to some embodiments, heat pipe heat transferring portion 228 is in contact with heat emitting plane 178 of each one of plurality of LED lamps 170ᵇ. According to some embodiments, heat pipe heat transferring portion 228 is in contact with heat emitting plane 178 of each one of plurality of LED lamps 170ᵇ, thereby enabling the transformation of thermal energy therebetween. According to some embodiments, the transformation of thermal energy between heat pipe heat transferring portion 228 and heat emitting plane 178 results in heating LED cooling fluid 175, as LED cooling fluid 175 contacts hollow illuminating LED pipe internal surface 206 at heat pipe heat transferring portion 228. According to some embodiments, the heating LED cooling fluid 175 results in the formation of vapors of LED cooling fluid 175. According to some embodiments, heat pipe heat transferring portion 228 is in contact with heat emitting plane 178 of each one of plurality of LED lamps 170ᵇ, thereby enabling the transformation of thermal energy therebetween, resulting in heating LED cooling fluid 175 residing in the vicinity of an internal surface of heat pipe heat transferring portion 228, so that vapors of heated LED cooling fluid 175 are formed.

Without wishing to be bound by any theory or mechanism of action, when LED cooling fluid 175 is volatile (e.g. it has a boiling point below 110° C.), and once the vapors of heated LED cooling fluid 175 are formed at heat pipe heat transferring portion 228, the vapor pressure is this portion is increased. The vapor pressure of LED cooling fluid 175 at heat pipe heat transferring portion 228 is initially higher than the equilibrium vapor pressure over LED cooling fluid 175 at heat pipe cooling portion 240, and this pressure gradient drives the vapors of heated LED cooling fluid 175 upwards from heat pipe heat transferring portion 228 towards heat pipe cooling portion 240, where the excess vapors condenses, releases its latent thermal energy, and warms heat pipe cooling portion 240. Following condensation, the vapors of heated LED cooling fluid 175 are transformed back into the liquid state of LED cooling fluid 175, and due to gravity force flows back to heat pipe heat transferring portion 228, to repeat the heat transfer cycle.

According to some embodiments, closed photobioreactor 100 further comprises at least one cooling unit 230 configured to reduce the temperature of LED cooling fluid 175. According to some embodiments, at least one cooling unit 230 is configured to reduce the temperature of vapors of heated LED cooling fluid 175, and condense them into liquid LED cooling fluid 175. According to some embodiments, at least one cooling unit 230 is configured to reduce the temperature of liquid LED cooling fluid 175. It is to be understood that cooling unit 230 may condense LED cooling fluid 175 when it is volatile and forms gas in response to being heated by LED lamp heat emitting plane 178. Alternatively, when LED cooling fluid 175 is non-volatile (e.g. an oil) cooling unit 230 may contribute in reducing its liquid temperature, such that it may be transformed colder to heat pipe heat transferring portion 228 (e.g. by diffusion).

As was detailed herein above when referring to FIGS. 5A-E, one of the advantages of closed photobioreactor 100 is the ability to keep plurality of light sources 170 from overheating. This advantage may be achieved by using at least one cooling unit 230, according to some embodiments as presented herein above.

According to some embodiments, each heat pipe 222 is in contact with one of at least one cooling unit 230. According to some embodiments, heat pipe cooling portion 240 is in contact with one of at least one cooling unit 230. According to some embodiments, heat pipe first closed end 236 is in contact with one of at least one cooling unit 230, as illustrated at FIG. 9. This enables cooling heated LED cooling fluid 175 (e.g. condensation of vapors thereof or cooling its liquid state) in the vicinity of heat pipe first closed end 236, according to some embodiments.

According to some embodiments, at least one cooling unit 230 may be located remote to closed photobioreactor 100. For example, at least one cooling unit 230 may be an air conditioner, a chiller and the like, positioned in the same room of closed photobioreactor 100, but not in contact therewith. The term "remote" as used in this paragraph refers to two or more elements, assemblies or devices, which do not come in contact one with the other. The two or more elements, assemblies or devices may be located in vicinity and there distance there between may be constant or variable, as long as they do not contact.

According to some embodiments, cooling unit 230 comprises at least one of a heat sink, a condenser, an air conditioner, a refrigerator, or any other cooling device known in the art, as well as combinations thereof. According to some embodiments, cooling unit 230 is a heat sink, as illustrated at FIG. 9.

The term "heat sink" as used herein, refers to a passive heat exchanger that transfers thermal energy generated by vapors of heated LED cooling fluid 175 to an external environment (typically the air surrounding the passive heat exchanger) where it is dissipated away from the passive heat exchanger, thereby allowing the condensation of LED cooling fluid 175. The heat sink is typically made from a highly conductive thermal material, and is designed to maximize the its surface area in contact with the external environment surrounding it, such as the air.

According to some embodiments, the heat sink is configured to transfer thermal energy from heat pipe cooling portion 240 and/or heat pipe first closed end 236 to a lower temperature fluid medium. The lower temperature fluid medium is typically the surrounding air, but can also be selected from water, refrigerants or oil.

According to some embodiments, at least one cooling unit 230 comprises a plurality of cooling units 230. According to further embodiments, plurality of cooling units 230 is corresponding to the plurality of heat pipes 222, wherein each one of the plurality of heat pipes 222 contacting one of the plurality of cooling units 230, at each heat pipe first closed end 236 and/or heat pipe cooling portion 240.

According to some embodiments, plurality of cooling units 230 does not correspond to the plurality of heat pipes 222, wherein each one of plurality of cooling units 230 is in contact with a group of heat pipes 222. According to some embodiments, each one of plurality of cooling units 230 is in contact with at least two heat pipes 222. According to some embodiments, each one of plurality of cooling units 230 is in contact with at least three heat pipes 222. According to some embodiments, each one of plurality of cooling units 230 is in contact with at least four heat pipes 222. According to some embodiments, each one of plurality of cooling units 230 is in contact with at least five heat pipes 222. According to some embodiments, at least one of plurality of cooling units 230 is in contact with at least two heat pipes 222. According to some embodiments, at least one of plurality of cooling units 230 is in contact with at least three heat pipes 222. According to some embodiments, at least one of plurality of cooling units 230 is in contact with at least four heat pipes 222. According to some embodiments, at least one of plurality of cooling units 230 is in contact with at least five heat pipes 222.

According to some embodiments, at least one cooling unit 230 comprises a single cooling unit 230. According to some embodiments, single cooling unit 230 is in contact with at least three of plurality of heat pipes 222. According to some embodiments, single cooling unit 230 is in contact with at least three of plurality of heat pipes 222. According to some embodiments, single cooling unit 230 is in contact with at least five of plurality of heat pipes 222. According to some embodiments, single cooling unit 230 is in contact with at least 10 of plurality of heat pipes 222. According to some embodiments, single cooling unit 230 is in contact with at least 20 of plurality of heat pipes 222. According to some embodiments, single cooling unit 230 is in contact with each one of plurality of heat pipes 222. It is to be understood that when cooling unit 230 is an air conditioner located in the vicinity of closed photobioreactor 100, the air conditioner may be considered as cooling each one of plurality of heat pipes 222. It is to be further understood that several air conditioning devices in the same room may be considered as a unitary cooling unit.

According to some embodiments, there is provided a process for growing a microorganism culture in an aqueous medium, wherein the process comprises growing at least one cell population in closed photobioreactor 100.

According to some embodiments, there is provided process for growing a microorganism culture in an aqueous medium, the process comprising (a) providing closed photobioreactor 100; (b) placing an aqueous biological medium comprising at least one cell population within internal cavity 104 and, optionally, inserting a plurality of light sources 170 in transparent pipe lumen 160 of at least some of the plurality of transparent pipes 150; (c) operating the plurality of light sources 170 to irradiate light into internal cavity 104 through said at least some of the plurality of transparent pipes 150, thereby growing the at least one cell population.

It is to be understood that the insertion of plurality of light sources 170 into transparent pipe lumens 160 is optional and depends on whether closed photobioreactor 100 is provided with plurality of light sources 170 already inserted into transparent pipe lumens 160; or closed photobioreactor 100 is provided with transparent pipe lumens 160 empty and requires insertion of light sources 170 there into.

According to some embodiments, there is provided process for growing a microorganism culture in an aqueous medium, the process comprising (a) providing a closed photobioreactor 100 for growing a microorganism culture in an aqueous medium, wherein closed photobioreactor 100 comprises: a vessel 110 comprising a vessel floor 112, vessel cover 114 positioned substantially parallel thereto, and at least one vessel wall 116 positioned perpendicular to vessel floor 112 and vessel cover 114, defining an internal cavity 104 for containing the microorganism culture in the aqueous medium, wherein vessel cover 114 comprises a plurality of openings 120; and plurality of transparent pipes 150 attached to vessel cover 114 accommodating a plurality of light sources 170 within transparent pipe lumens 160 thereof, wherein each of plurality of transparent pipes 150 extends through one of openings 120, wherein each one of plurality of transparent pipes 150 has a transparent pipe first open end 152 located out of internal cavity 104, and a transparent pipe second end 154, wherein transparent pipe first portion 156 of one of plurality of transparent pipes 150 is connected to vessel cover 114 or vessel 112, and a transparent pipe second portion 158 of each one of plurality of transparent pipes 150 is located within internal cavity 104, wherein each one of plurality of transparent pipes 150 is substantially sealed to one of openings 120, so that internal cavity 114 is isolated from surrounding environment 106 of the vessel 110; (b) placing an aqueous biological medium comprising at least one cell population within internal cavity 104; (c) optionally inserting a plurality of light sources 170 in transparent pipe lumen 160 of at least some of the plurality of transparent pipes 150; (d) operating the plurality of light sources 170 to irradiate light into internal cavity 104 through said at least some of the plurality of transparent pipes 150, thereby growing the at least one cell population.

According to some embodiments, the process of the present invention is a fed-batch process.

According to some embodiments, the step of growing the at least one cell population is performed at a temperature in the range of 5° C. to 40° C. According to some embodiments, the step of growing the at least one cell population is performed at a temperature in the range of 10° C. to 40° C. According to some embodiments, the step of growing the at least one cell population is performed at a temperature in the range of 10° C. to 37° C. According to some embodiments, the step of growing the at least one cell population is performed at a temperature in the range of 20° C. to 37° C.

According to some embodiments, step (c) comprises operating the plurality of light sources to irradiate light into the internal cavity at a wavelength in a range of 400-700 nanometers. According to some embodiments, step (c) comprises operating the plurality of light sources to irradiate light into the internal cavity at a wavelength in a range of 250-1100 nanometers.

According to some embodiments, growing the at least one cell population is performed a rate in the range of 0.-6 grams per liter per day.

According to some embodiments, the process further comprises a step of removing plurality of light sources 170 from the plurality of transparent pipes 150. According to some embodiments, the process further comprises a step of removing the plurality of light sources 170 from the respective transparent pipe lumens 160.

It is to be understood that the step of removing the plurality of light sources 170 from the respective transparent pipe lumens 160 of transparent pipes 150 is performed after the step of operating the plurality of light sources 170 to irradiate light into internal cavity 104. However, as can be appreciated by the skilled in the art, after the removal of light sources 170 from transparent pipe lumens 160 and, optionally cleaning bioreactor 100, light sources 170 (whether the original light sources or replacements) may be reinstated into transparent pipe lumens 160 and a new aqueous biological medium may be inserted into internal cavity 104 for a new sequence of operation and growth of the relevant organism.

According to some embodiments, the step of removing the plurality of light sources 170 from the respective transparent pipe lumens 160 of transparent pipes 150 is performed after the step of operating the plurality of light sources 170 to irradiate light into internal cavity 104.

According to some embodiments, the process further comprises a step of removing the proliferated cell population from closed photobioreactor 100. According to some embodiments, the step of removing the proliferated cell population entails extracting the aqueous biological medium from internal cavity 104 through a dedicated outlet (not shown in the figures). Dedicated outlets for the extraction of products from bioreactors are mediating between the internal cavity and the outside environment of the bioreactor. Such outlets typically include a valve for monitoring the exit flow of products. According to some embodiments, the step of removing the proliferated cell population entails removing vessel cover 114 and extracting the aqueous biological medium from internal cavity 104.

According to some embodiments, the step of removing the proliferated cell population from closed photobioreactor 100 is performed after the step of removing the plurality of light sources 170 from the respective transparent pipe lumens 160 of transparent pipes 150.

According to some embodiments, the process further comprises a step of inserting a cleansing composition into the internal cavity and heating the cleansing composition to a predetermined temperature.

According to some embodiments, the cleansing composition is liquid. According to some embodiments, the cleansing composition is an aqueous cleansing composition. According to some embodiments, the cleansing composition is selected from an acidic aqueous composition, a basic aqueous composition and a detergent composition. According to some embodiments, the cleansing composition comprises detergents. According to some embodiments, the cleansing composition is an aqueous composition comprising detergents. According to some embodiments, the cleansing composition an acidic aqueous composition. According to some embodiments, the cleansing composition a basic aqueous composition. According to some embodiments, the predetermined temperature is at least 50° C. According to some embodiments, the predetermined temperature is at least 55° C. According to some embodiments, the predetermined temperature is at least 60° C. According to some embodiments, the predetermined temperature is at least 65° C. According to some embodiments, the predetermined temperature is at least 70° C. According to some embodiments, the predetermined temperature is at least 75° C. According to some embodiments, the predetermined temperature is at least 80° C. According to some embodiments, the predetermined temperature is at least 85° C. According to some embodiments, the predetermined temperature is at least 90° C. According to some embodiments, the predetermined temperature is at least 95° C. According to some embodiments, the predetermined temperature is at least 100° C. According to some embodiments, the predetermined temperature is at least 105° C. According to some embodiments, the predetermined temperature is at least 115° C. According to some embodiments, the predetermined temperature is at least 120° C. According to some embodiments, the predetermined temperature is at least 125° C. Typically, clearing of bioreactor used in the proliferation of algae is performed in temperatures in the range of 130° C.-140° C. According to some embodiments, the predetermined temperature is in the range of 120° C. to 140° C.

According to some embodiments, the step of inserting and heating the cleansing composition is performed after the step of removing the proliferated cell population from closed photobioreactor 100. According to some embodiments, the step of inserting and heating the cleansing composition is performed after the step of removing the plurality of light sources 170 from the respective transparent pipe lumens 160 of transparent pipes 150.

According to some embodiments, the step of inserting the cleansing composition into internal cavity 104 entails contacting the cleansing composition with an internal portion 117 of the vessel wall vessel wall 116. According to some embodiments, the step of inserting the cleansing composition into internal cavity 104 entails contacting the cleansing composition with vessel floor 112. According to some embodiments, the step of inserting the cleansing composition into internal cavity 104 entails contacting the cleansing composition with transparent pipe second portion 158. According to some embodiments, the step of inserting the cleansing composition into internal cavity 104 entails contacting the cleansing composition with transparent pipes 150.

According to some embodiments, the process further comprises a step of removing the cleansing composition from the internal cavity, thereby cleaning closed photobioreactor 100. According to some embodiments, the process further comprises a step of removing the cleansing composition from the internal cavity, thereby cleaning internal cavity 104 of closed photobioreactor 100.

According to some embodiments, the process further comprises the step of inserting an aqueous composition comprising acids, bases or both into the internal cavity 104 after removing the proliferated cell population from the closed photobioreactor; removing the aqueous composition from the internal cavity 104; and performing a Sterilization in Place (SIP) within the internal cavity, thereby cleaning the closed photobioreactor 100. According to some embodiments, the SIP comprises steam sterilizing the internal cavity 104, treating the internal cavity 104 with water at a temperature above 100° C. or both.

According to some embodiments, the process further comprising repeating steps (a) to (c) at least once more after completion of said cleaning, thereby growing additional cell populations.

According to some embodiments, step (b) further comprises placing nutrients for the proliferation of the cell population within the internal cavity. Specifically, it is to be understood that nutrients may be inserted through vessel cover 114 or through a designated opening as known in the art. It is further to be understood by the skilled in the art the specific nutrients required for growing various species including, but not limited to phototropic species, such as phototropic algae. According to some embodiments, the nutrient comprises sugars.

According to some embodiments, the aqueous biological medium comprises a single cell population. According to some embodiments, the aqueous biological medium comprises a single species. According to some embodiments, the aqueous biological medium comprises a plurality of cell populations. According to some embodiments, the aqueous biological medium comprises a plurality of cell species.

As detailed herein, the sequence of step required to grow microorganisms under sealing and illumination requires (i) fermentation of the relevant culture at conditions, which enable sealing, while still enabling internal illumination; (ii) removal of the fermented culture from the bioreactor vessel and (iii) sterilization of the vessel internal cavity. While step (i) (comparable with step (c) of the process disclosed herein) requires the presence of light sources, step (iii) is performed under heating conditions. Such elevated temperatures are detrimental to the light sources. Therefore, in order to properly sterilize the vessel internal cavity, it is required to frequently remove the light sources from the bioreactor system—an operation which is highly difficult with known bioreactors.

The present closed photobioreactor 100 and the present process of operation thereof enables a solution to the problem existing in known photobioreactors, when growing organisms, which require both illumination and sealed environment. The is a critical requirement to the growth of various microorganism, in particular phototrophs, heterotrophs and/or mixotrophs, such as algae phototrophs, heterotrophs and/or mixotrophs. Such species require effective exploitation of an organic carbon source (e.g. sugars) with minimum contaminations, which in it turn requires proper sealing.

As the transparent pipes penetrate through openings in the bioreactor cover, according to some embodiments, there is a risk of a non-sealed environment. Such environment may enable passage of fluids (e.g. air) and other contaminants from the external environment into the vessel internal cavity. However, the present photobioreactor 100 solves these problems as detailed above.

According to some embodiments, the cell population comprises a phototrophic bio-organism species. According to some embodiments, the cell population comprises a mixtrophic bio-organism species. According to some embodiments, the cell population comprises a heterotrophic bio-organism species.

As detailed herein, the microorganism culture may be of any microorganism species, which requires light for its cultivation, according to some embodiments. According to some embodiments, the microorganism culture is a phototroph culture. According to some embodiments, the microorganism culture is a mixotroph culture. According to some embodiments, the microorganism culture is a heterotroph culture. According to some embodiments, the microorganism culture is of a single cell species. According to some embodiments, the microorganism culture is of an algae or a bacteria. According to some embodiments, the microorganism culture is of an algae or a cyanobacteria. According to some embodiments, the microorganism culture is of a single cell algae or a single cell bacteria. According to some embodiments, the microorganism culture is of a single cell algae or a single cell cyanobacteria. According to some embodiments, the microorganism culture is an algae culture.

According to some embodiments, the cell population is selected from the group consisting of bacteria and algae. According to some embodiments, the cell population comprises an algae species. According to some embodiments, the cell population comprises a bacteria species.

According to some embodiments, the cell population comprises a phototrophic algae. According to some embodiments, the cell population comprises a phototrophic bacteria. According to some embodiments, the cell population comprises a mixotrophic algae. According to some embodiments, the cell population comprises a mixotrophic bacteria. According to some embodiments, the cell population comprises a heterotrophic algae. According to some embodiments, the cell population comprises a heterotrophic bacteria.

According to some embodiments, the process further comprises a step of extracting at least one material from the proliferated cell population is performed after step (c).

It is to be understood that step of extracting may be performed before, after or in parallel of any one or more of the bioreactor cleaning steps detailed above. Specifically, the extraction is performed independently out of the reactor.

According to some embodiments, the material extracted by the process of the present invention is selected from the group consisting of: a carotenoid, a protein, a lipid, a sugar, a fatty acid, a pigment, a peptide and a combination thereof. Each possibility represents a separate embodiment.

According to some embodiments, there is provided a composition comprising the microorganism culture grown by the process disclosed herein, the at least one material extracted by the process disclosed herein, or a combination thereof. According to some embodiments, there is provided a composition comprising the microorganism culture grown by the process disclosed herein. According to some embodiments, there is provided a composition comprising the at least one material extracted by the process disclosed herein. According to some embodiments, there is provided a composition consisting of the microorganism culture grown by the process disclosed herein, the at least one material extracted by the process disclosed herein, or a combination thereof. According to some embodiments, there is provided a composition consisting of the microorganism culture grown by the process disclosed herein. According to some embodiments, there is provided a composition consisting of the at least one material extracted by the process disclosed herein.

The composition may include any solvent, carrier and the like, as known in the art.

The term "plurality", as used herein, means more than one.

It is appreciated that certain features of the disclosed technology, which are, for clarity, described in the context of separate embodiments, may also be provided in combination in a single embodiment. Conversely, various features of the disclosed technology, which are, for brevity, described in the context of a single embodiment, may also be provided separately or in any suitable sub-combination or as suitable in any other described embodiment of the disclosed technology. No feature described in the context of an embodiment is to be considered an essential feature of that embodiment, unless explicitly specified as such.

Although steps of methods according to some embodiments may be described in a specific sequence, disclosed methods may comprise some or all of the described steps carried out in a different order. A disclosed method may comprise all of the steps described or only a few of the described steps. No particular step in a disclosed method is to be considered an essential step of that method, unless explicitly specified as such.

Although the disclosed technology is described in conjunction with specific embodiments thereof, it is evident that numerous alternatives, modifications and variations that are apparent to those skilled in the art may exist. Accordingly, the disclosed technology embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways. Accordingly, the invention embraces all such alternatives, modifications and variations that fall within the scope of the appended claims.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A closed photobioreactor for growing a microorganism culture in an aqueous medium, the photobioreactor comprising:

a vessel comprising a vessel floor, a vessel cover positioned substantially-parallel thereto, and at least one vessel wall positioned perpendicular to the vessel floor and vessel cover, defining an internal cavity for containing the microorganism culture in the aqueous medium, wherein the vessel cover comprises a plurality of openings; and a plurality of transparent pipes attached to the vessel cover configured to accommodate a plurality of light sources within lumens thereof, wherein each of the transparent pipes extends through one of the openings, wherein each transparent pipe has a first open end located out of the internal cavity of the vessel, and a second end, wherein a first portion of each transparent pipe is connected to the vessel cover or the vessel, and a second portion of each transparent pipe is located within the internal cavity, wherein each of the transparent pipes is substantially sealed to one of the openings, so that the internal cavity is isolated from the surrounding environment of the vessel, and wherein the first portion of each transparent pipe is connected to the vessel cover, and wherein the vessel cover comprises a plurality of hollow cover extensions, wherein each hollow cover extension extends from one of the openings upward, and has a first open end offset upward from the vessel cover and a second open end at the level of the vessel cover, wherein the first portion of each transparent pipe extends through one of the hollow cover extensions and is retained thereby.

2. The closed photobioreactor of claim 1, further comprising a plurality of retention units, wherein each of the retention units comprises at least one retention member, each retention member is configured to fix one of the transparent pipes to one of the hollow cover extensions, wherein each of the retention units comprises at least one retention member disposed circumferentially between the first portion of one of the transparent pipes and one of the hollow cover extensions, and longitudinally between the second end of one of the hollow cover extensions and the first end of one of the transparent pipes, and configured to limit spontaneous movement of the transparent pipe in the lateral and longitudinal directions.

3. The closed photobioreactor of claim 2, wherein each of the retention units comprises a plurality of lower retention members and a plurality of upper retention members, each of which is disposed circumferentially between one of the transparent pipes and one of the hollow cover extensions, and longitudinally between the second end of one of the hollow cover extensions and the first end of one of the transparent pipes, and configured to limit spontaneous movement of the transparent pipe in the lateral and longitudinal directions.

4. The closed photobioreactor of claim 3, wherein each of the lower retention members comprises a lower squeezable gasket, and each of the upper retention members comprises an upper squeezable gasket.

5. The closed photobioreactor of claim 4, wherein each hollow cover extension comprises an internal recess, located between the first end and the second end thereof, wherein each lower squeezable gasket is housed within one of the internal recesses and pressing the transparent pipe inward, wherein each hollow cover extension comprises a slanted portion at the first end thereof tapering upwards, wherein each upper squeezable gasket is housed within one of the slanted portions and is pressed against the transparent pipe inward.

6. The closed photobioreactor of claim 4, wherein each of the transparent pipes is externally tubular and each of the hollow cover extensions is internally tubular, wherein each of the lower squeezable gaskets comprises a lower rubber O-ring, and each of the upper squeezable gaskets comprises a upper rubber O-ring, wherein each of the lower rubber O-rings and the upper rubber O-rings, when expanded, has an internal diameter larger than the external diameter of the first portion of each corresponding transparent pipe.

7. The closed photobioreactor of claim 6, further comprising a plurality of double-open caps reversibly attachable to the first end of each hollow cover extension, wherein each double-open cap has a plane having a diameter smaller than the external diameter of the upper O-ring, wherein upon capping the double-open cap to the hollow cover extension, the plane presses against the upper O-ring and the slanted portion of the hollow cover extension, to press fit the upper O-ring inward against the transparent pipe, and prevents the transparent pipe from longitudinally moving upwards.

8. The closed photobioreactor of claim 7, wherein each double-open cap comprises a threaded internal tubular portion and each hollow cover extension comprises a threaded external portion, wherein the double-open cap is screwable to the hollow cover extension, wherein upon screwing the cap presses the hollow cover extension inwards, further press fitting the hollow cover extension and upper O-ring inward against the transparent pipe.

9. The closed photobioreactor of claim 1, wherein the lumen of each transparent pipe is in fluid communication with the surrounding environment of the vessel and isolated from the internal cavity of the vessel.

10. The closed photobioreactor of claim 1, wherein each of the vessel cover and hollow cover extensions is made of metal, wherein each of the hollow cover extensions is welded to the vessel cover.

11. The closed photobioreactor of claim 1, wherein the first open end of each transparent pipe is offset upward from the first open end of the hollow extension, which retains it.

12. The closed photobioreactor of claim 1, wherein the at least one vessel wall is a double walled cooling jacket comprising at least one internal wall, at least one external wall and a cooling liquid there between, wherein the internal wall is bounding the internal cavity of the vessel.

13. The closed photobioreactor of claim 1, wherein the plurality of transparent pipes are accommodating a plurality of light sources within the lumens thereof, wherein upon the accommodation, a positive gap between the internal diameter of the transparent pipe and the external dimensions of the light source exists, wherein each of the light sources is drawable from the transparent pipe, which accommodates it, wherein each transparent pipe is accommodating one or more of the light sources and a cooling liquid, wherein each light source comprises at least one illuminating plane and at least one heat emitting plane, wherein the cooling liquid is in contact with at least the heat emitting plane.

14. The closed photobioreactor of claim 13, wherein each of the plurality of light sources is an LED lamp and the closed photobioreactor comprises a plurality of hollow illuminating LED pipes, wherein each hollow illuminating LED pipe comprises one or more of the LED lamps, each hollow illuminating LED pipe comprising:

a first open end facing the vessel cover;

a second end facing the vessel floor;

an internal surface connected to the heat emitting plane of one or more of the LED lamps;

an external surface connected to the illuminating plane of one or more of the LED lamps;

and a lumen within the internal surface of the hollow illuminating LED pipe;

wherein the cooling liquid is in contact with at least the heat emitting plane, enabling heat transfer between the cooling liquid and the heat emitting plane of one or more of the LED lamps.

15. The closed photobioreactor of claim 1, further comprising a plurality of hollow illuminating LED pipes, and a plurality of heat pipes wherein each hollow illuminating LED pipe comprises:

a plurality of LED lamps, each comprising a heat emitting plane and an illuminating plane;

a first open end facing the vessel cover;

a second end facing the vessel floor;

an internal surface connected to the heat emitting plane of each one of the plurality of LED lamps;

an external surface connected to the illuminating plane of each one of the plurality of LED lamps;

and a lumen within the internal surface of the hollow illuminating LED pipe;

wherein each heat pipe is made from a heat conducting material, and is containing a LED cooling fluid, wherein each heat pipe comprises an internal surface and an external surface, wherein each of the plurality of hollow illuminating LED pipes is accommodated within the lumen of one of the plurality of transparent pipes, wherein each of the heat pipes is accommodated within the lumen of one of the hollow illuminating LED pipes, so that the external surface of the heat pipe is in contact with the internal surface of the hollow illuminating LED pipe, wherein the LED cooling fluid is in contact with the internal surface of the heat pipe, enabling heat transfer between the cooling fluid and the heat emitting plane of the plurality of LED lamps.

16. The closed photobioreactor of claim 15, wherein each heat pipe comprises:

a first closed end extending through a transparent pipe first open end, which accommodates it;

a second closed end facing the vessel floor; and a heat transferring portion between the first end and the second end;

wherein the heat transferring portion is in contact with the internal surface of the hollow illuminating LED pipe.

17. A process for growing a microorganism culture in an aqueous medium, the process comprising:

(a) providing the closed photobioreactor of claim 1, wherein the plurality of transparent pipes are accommodating a plurality of light sources within the lumens thereof;

(b) placing an aqueous biological medium comprising at least one cell population within the internal cavity; and (c) operating the plurality of light sources to irradiate light into the internal cavity through said at least some of the plurality of transparent pipes, thereby growing the at least one cell population.

18. The process of claim 17, further comprising removing the plurality of light sources from the transparent pipes.

* * * * *